United States Patent
Lee et al.

(10) Patent No.: US 10,131,888 B2
(45) Date of Patent: Nov. 20, 2018

(54) INTRACELLULAR PROTEIN DELIVERY

(71) Applicant: IPROGEN BIOTECH INC., Richmond (CA)

(72) Inventors: Keun Ho Lee, Surrey (CA); Leo Yen-Cheng Lin, Vancouver (CA); Aikun Wang, Vancouver (CA)

(73) Assignee: IPROGEN BIOTECH INC., Richmond, CA (US)

( * ) Notice: Subject to any disclaimer, the term of this patent is extended or adjusted under 35 U.S.C. 154(b) by 0 days.

(21) Appl. No.: 15/970,603

(22) Filed: May 3, 2018

(65) Prior Publication Data

US 2018/0298359 A1    Oct. 18, 2018

Related U.S. Application Data

(62) Division of application No. 14/409,633, filed as application No. PCT/CA2013/000614 on Jul. 2, 2013, now Pat. No. 9,994,829.

(60) Provisional application No. 61/667,049, filed on Jul. 2, 2012.

(51) Int. Cl.
| | |
|---|---|
| *C12N 9/16* | (2006.01) |
| *C07K 16/10* | (2006.01) |
| *C07K 14/43* | (2006.01) |
| *C07K 16/18* | (2006.01) |
| *C12N 15/85* | (2006.01) |
| *C07K 14/435* | (2006.01) |

(52) U.S. Cl.
CPC .......... *C12N 9/16* (2013.01); *C07K 14/43504* (2013.01); *C07K 16/1072* (2013.01); *C07K 16/18* (2013.01); *C12N 15/85* (2013.01); *C07K 2319/00* (2013.01); *C07K 2319/02* (2013.01); *C07K 2319/10* (2013.01); *C07K 2319/30* (2013.01); *C07K 2319/60* (2013.01); *C12Y 301/03001* (2013.01)

(58) Field of Classification Search
None
See application file for complete search history.

(56) References Cited

PUBLICATIONS

Flinterman et al., "Deliver of Therapeutic Proteins as Secretable TAT Fusion Products", Molecular Therarpy, 2009, 17(2):334-342.*

* cited by examiner

*Primary Examiner* — Suzanne M Noakes
(74) *Attorney, Agent, or Firm* — Snell & Wilmer LLP

(57) ABSTRACT

A secretion signal peptide sequence (SP) in combination with a cleavage inhibition sequence (CIS) fused to a structural gene sequence in a recombinant expression system can be used to express a full length protein with an SP in a cell. Such a fusion protein may be purified to homogeneity from a membrane fraction of the cell. The SP in combination with the CIS is a protein transduction domain that exhibits superior intracellular protein transduction efficiency when the SP precedes the CIS in a N to C-terminus direction.

16 Claims, 16 Drawing Sheets

Specification includes a Sequence Listing.

Fig. 3A

| SEQ ID # | Sequence | Fusion attachment | Reference |
|---|---|---|---|
| PTM1: 09, 10 | AAVALLPAVLLALLAP | N-terminal | Lin and Hawiger (1998) US Patent No. 5,807,746 |
| PTM2: 11, 12 | KETWWETWWTEWSQPKKKRKV | N-terminal | Divita et al. (2005) US Patent No. 6,841,535 B2 |
| PTM3: 13, 14 | KKAAAVLLPVLLAAP | N-terminal | O'Mahony (2004) US Patent No. 6,780,846 B1 |
| PTM4: 15, 16 | VLLAVTP | N-terminal | Jo et al. (2010) US Patent No. 2010/0197598 |
| PTM5: 17, 18 | AVVVALAP | N-terminal | Jo et al. (2010) US Patent No. 2010/0197598 |
| PTM6: 19, 20 | LVLAAPAALP | N-terminal | Jo et al. (2010) US Patent No. 2010/0197598 |
| PTM7: 21, 22 | SGRQIKIWFQNRRMKWKK | N-terminal | Derossi et al. (1996) J. Biol. Chem. 271: 18188-93 |
| TAT: 03, 04 | RKKRRQRRR | N-terminal | Frankel et al. (1998) US Patent No. 5,804,604 |

Fig. 3B

| SEQ ID # | Sequence | Fusion attachment | Reference |
|---|---|---|---|
| SP1: 23, 24 | LGPCMLLLLLLLGLRLPGVWA | C-terminal | Millan (1986) J. Biol. Chem. 261: 3112-5 |
| 1PS: 25, 26 | AWVGPLRLGLLLLLLLMCPGL | C-terminal | Millan (1986) J. Biol. Chem. 261: 3112-5 |

Fig. 4

| ID | Oligonucleotide Primers | SEQ ID # |
|---|---|---|
| CD33 signal peptide | (5'→3') GGTACCATGGTGCTGCTGCTGCTGCTGCCCCTGCTGTGGGCCGGCGCCCTCGAG <br> CTCGAGGGCGCCGGCCCACAGCAGGGGCAGCAGCAGCAGCAGCACCATGGTACC (3'←5') <br> KpnI ... NarI XhoI | FWD: 77 <br> REV: 78 |
| PTM 1 | (5'→3') GGCGCCCTGGCCGCCGCCGTGGCCCTGCTGCCCGCCGTGCTGCTGGCCCTGCTGGCCCCCGAGCTC <br> CCGCGGGACCGGCGGCGGCACCGGGACGACGGGCGGCACGACGACCGGGACGACCGGGGGCTCGAG (3'←5') <br> NarI ... SacI | FWD: 79 <br> REV: 80 |
| PTM 2 | (5'→3') GGCGCCCTGGCCAAGGAGACCTGGTGGGAGACCTGGTGGACCGAGTGGAGCCAGCCCAAGAAGAAGCGGAAGGTGGAGCTC <br> CCGCGGGACCGGTTCCTCTGGACCACCCTCTGGACCACCTGGCTCACCTCGGTCGGGTTCTTCTTCGCCTTCCACCTCGAG (3'←5') <br> NarI ... SacI | FWD: 81 <br> REV: 82 |
| PTM 3 | (5'→3') GGCGCCCTGGCCAAGAAGGCCGCCGCCGTGCTGCTGCCCGTGCTGCTGGCCGCCCCCGAGCTC <br> CCGCGGGACCGGTTCTTCCGGCGGCGGCACGACGACGGGCACGACGACCGGCGGGGGCTCGAG (3'←5') <br> NarI ... SacI | FWD: 83 <br> REV: 84 |
| PTM 4 | (5'→3') GGCGCCCTGGCCGTGCTGCTGGCCGTGACCCCCGAGCTC <br> CCGCGGGACCGGCACGACGACCGGCACTGGGGGCTCGAG (3'←5') <br> NarI ... SacI | FWD: 85 <br> REV: 86 |
| PTM 5 | (5'→3') GGCGCCCTGGCCGCCGCCGTGGTGGTGGCCCTGGCCCCCGAGCTC <br> CCGCGGGACCGGCGGCGGCACCACCACCGGGACCGGGGGCTCGAG (3'←5') <br> NarI ... SacI | FWD: 87 <br> REV: 88 |
| PTM 6 | (5'→3') GGCGCCCTGGCCCTGGTGCTGGCCGCCCCCGCCGCCCCTGCCCGAGCTC <br> CCGCGGGACCGGGACCACGACCGGCGGGGCGGCGGGACGGGCTCGAG (3'←5') <br> NarI ... SacI | FWD: 89 <br> REV: 90 |
| PTM 7 | (5'→3') GGCGCCCTGGCCAGCGGCCGGCAGATCAAGATCTGGTTCCAGAACCGGCGGATGAAGTGGAAGAAGGAGCTC <br> GAGCTCCTTCTTCCACTTCATCCGCCGGTTCTGGAACCAGATCTTGATCTGCCGGCCGCTGGCCAGGGCGCC (3'←5') <br> NarI ... SacI | FWD: 91 <br> REV: 92 |

Fig. 5

| Structural Gene Design | Protein Transduction Efficiency* |
|---|---|
| Cell alone | — |
| SP1-TAT-GFP-Fc | +++++ |
| PTM1-GFP-Fc | — |
| PTM4-GFP-Fc | — |
| PTM5-GFP-Fc | — |
| PTM6-GFP-Fc | — |
| TAT-GFP-Fc | + |
| GFP-Fc-TAT | + |
| GFP-Fc-SP | — |
| GFP-Fc-PS | — |
| NLS-TD-SUMO-GFP-His | — |
| GFP-Fc + Synvolux SAINT-PhD lipid amphiphile in Serum Free Media | + |
| GFP-Fc + Synvolux SAINT-PhD lipid amphiphile in DMEM + 10% FBS media | — |

\* The transduction efficiency of SP1-TAT-GFP-Fc is set as a reference (e.g., 100%) for comparison. The cutoff for background noise is set at 0-5%, and is indicated by "-".
+: 5-10%; ++: 10-25%; +++: 25-50%; ++++: 50-75%; +++++: 75-100%.

Fig. 7

| Cell Type | SP1-TAT-GFP-Fc Transduction Efficiency* |
| --- | --- |
| B Cell Lymphoma | +++++ |
| Lung Cancer (Calu6) | +++++ |
| Cervical Cancer (HeLa) | +++++ |
| Bronchial Cancer (HBE) | ++ |
| Skin Cancer (MMAN) | +++++ |
| Prostate Cancer (PC3) | ++ |

\* The transduction efficiency of SP1-TAT-GFP-Fc in HeLa cell is set as a reference (e.g., 100%) for comparison. The cutoff for background noise is set at 0-5%, and is indicated by "-".
+: 5-10%; ++: 10-25%; +++: 25-50%; ++++: 50-75%; +++++: 75-100%.

Fig. 8
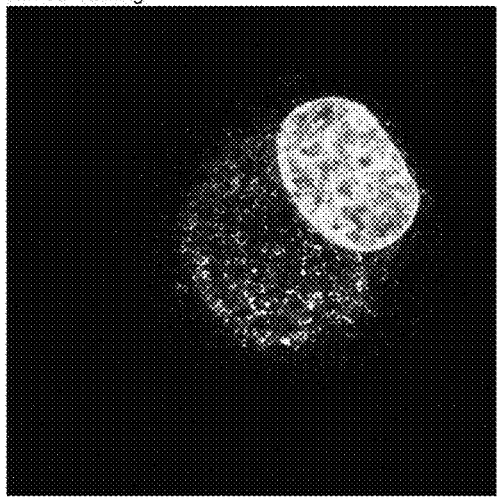
Nuclear staining
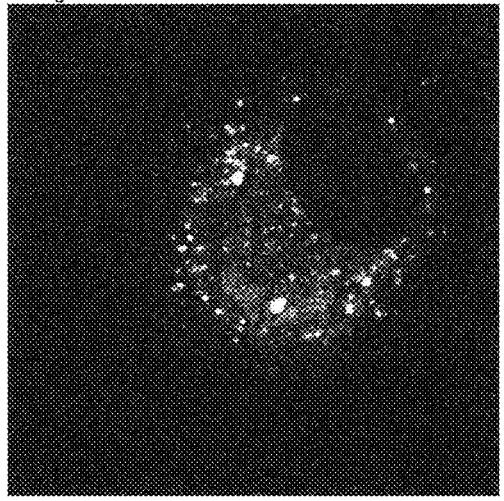
GFP green fluorescence emission
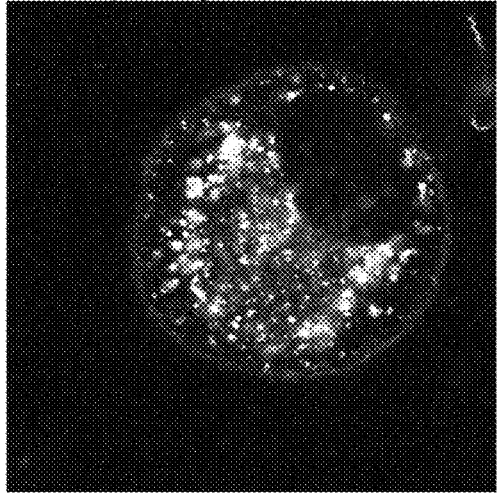
Membrane lipid staining
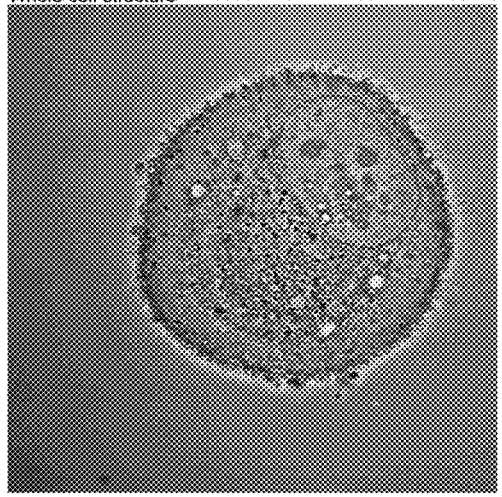
Whole cell structure

* The transduction efficiency of SP1-TAT-GFP-Fc is set as a reference (e.g., 100%) for comparison. The cutoff for background noise is set at 0-5%, and is indicated by "-".
+: 5-10%; ++: 10-25%; +++: 25-50%; ++++: 50-75%; +++++: 75-100%.

Fig. 9B

| SEQ ID # | Structural Gene Design | Transduction Efficiency in HeLa* |
|---|---|---|
| PAP-P4G: 39, 40<br>GFP-Fc: 55, 56 | N-[PAP]-[P4G]-[GFP]-[Fc]-C | — |
| SP1-3P: 41, 42<br>GFP-Fc: 55, 56 | N-[SP1]-[3P]-[GFP]-[Fc]-C | — |
| SP*-9R: 43, 44<br>GFP-Fc: 55, 56 | N-[SP*]-[9R]-[GFP]-[Fc]-C<br>(SP*: Deletion of PGVWA in SP1:<br>MLGPC MLLLL LLLGL RL) | +++ |
| PGVWA-9R: 45, 46<br>GFP-Fc: 55, 56 | N-[PGVWA]-[9R]-[GFP]-[Fc]-C<br>(PGVWA: Deletion of LGPC MLLLL LLLGL RL in SP1) | — |
| SP3R: 47, 48<br>GFP-Fc: 55, 56 | N-[SP3R]-[GFP]-[Fc]-C<br>(SP3R: Replacement of VWA to RRR in SP1:<br>MLGPC MLLLL LLLGL RLPGR RR) | — |

\* The transduction efficiency of SP1-TAT-GFP-Fc is set as a reference (e.g., 100%) for comparison.
The cutoff for background noise is set at 0-5%, and is indicated by "—".
+: 5-10%; ++: 10-25%; +++: 25-50%; ++++: 50-75%; +++++: 75-100%.

Effect of Anionic Heparin on Protein Transduction*

Effect of Eliminating the Cell Surface Proteins on Protein Transduction*

\* The transduction efficiency of SP1-TAT-GFP-Fc in HeLa cell is set as a reference (e.g., 100%) for comparison. The cutoff for background noise is set at 0-5%, and is indicated by "-".
+: 5-10%; ++: 10-25%; +++: 25-50%; ++++: 50-75%; +++++: 75-100%.

Effect of SP1-TAT Analog Peptide on Protein Transduction*

Effect of Temperature on Protein Transduction*

* The transduction efficiency of SP1-TAT-GFP-Fc in HeLa cell is set as a reference (e.g., 100%) for comparison. The cutoff for background noise is set at 0-5%, and is indicated by "-".
+: 5-10%; ++: 10-25%; +++: 25-50%; ++++: 50-75%; +++++: 75-100%.

INTRACELLULAR PROTEIN DELIVERY

CROSS-REFERENCE TO RELATED APPLICATIONS

This application is a divisional of U.S. patent application Ser. No. 14/409,633 filed on Dec. 19, 2014, which is a U.S. national stage application from PCT/CA2013/000614 filed on Jul. 2, 2013, which claims priority to U.S. provisional application Ser. No. 61/667,049 filed Jul. 2, 2012, the disclosures of which are incorporated herein by reference.

TECHNICAL FIELD

The field of the invention is intracellular delivery using protein transduction domain, including protein delivery.

BACKGROUND ART

Conventional technologies for delivering exogenous proteins from an extracellular environment across a membrane lipid bilayer into cells are limited by inefficient membrane penetration of proteins, especially large proteins.

Synthetic peptides based on structure and sequence of secretion signal peptides have been exploited as protein delivery carriers (see, U.S. Pat. No. 5,807,746; U.S. Pat. No. 6,841,535; U.S. Patent No. 2010/0197598). Similarly, synthetic lipid amphiphiles have been demonstrated as intracellular delivery vehicles for a variety of bio-active molecules (see, U.S. Pat. No. 6,726,894). However, transfection technologies based on such carriers require that peptides (see, U.S. Pat. No. 6,841,535; U.S. Pat. No. 6,780,846) as well as amphiphiles (see, U.S. Pat. No. 6,726,894) be maintained at high concentration for complex formation between a cargo substance and the carrier and for intracellular delivery of the complex. This poses a serious limitation in therapeutic applications because unbound carrier can associate non-specifically with extracellular substances. Although covalent linkage between a transfection vector and its cargo can be established through chemical modification, lack of reaction specificity poses the risk of rendering the cargo inactive. The covalent reaction may occur at a catalytic center of a cargo enzyme, or on a functional surface of the cargo protein leading to inhibition or inactivation of the cargo protein function. Also, lack of specificity in covalent linkage formation between a cargo molecule and a protein transduction domain may lead to a heterogenous distribution of cargo molecules linked to the transduction domain at different positions.

Use of proteins fused to a secretion signal peptide produced as a recombinant single polypeptide chain has not been exploited. This is because during maturation of such a protein in a cell, the secretion signal sequence is typically cleaved.

SUMMARY OF THE INVENTION

The present invention is based at least in part, on the recognition that a cleavage inhibition sequence (CIS) placed next to a secretion signal (SP) in a recombinant protein can efficiently block cleavage of the secretion signal. It can also halt secretion of the protein from a cell in which it is expressed, allowing for its recovery by such means as sedimentation fractionation, detergent extraction, and/or chromatography purification. This invention is also based on the discovery that a combination of a CIS and an SP also exhibits enhanced efficiency as a protein transduction agent. The latter aspect is dependent on a specific arrangement of the SP and the CIS, with SP preceding the CIS in an N-terminus to C-terminus direction.

Transduction efficiency of some embodiments of this invention can greatly surpass that of methodologies that employ just a secretion signal peptide or a polycation-based transduction domain (e.g., HIV-1 TAT, poly Arg/Lys peptides). Without being bound to a particular theory, it appears that the superior transduction efficiency that can be achieved with particular embodiments of this invention result from intracellular delivery being mediated through receptors on a recipient cell surface. This indicates a mechanism that is different from direct phospholipid association and other membrane penetration modes known to occur in some conventional intracellular delivery technologies.

Various embodiments of this invention provide a transduction domain comprising, in a N to a C-terminus direction, a secretion signal peptide, an optional linker and a cleavage inhibition peptide which domain exhibits superior efficiency in intracellular transduction of proteins. Also provided is use of such a domain as a transduction agent to deliver a linked cargo component into a target cell.

Various embodiments of this invention provide nucleic acids encoding a transduction domain of this invention, vectors comprising such a nucleic acid and host cells comprising such nucleic acids and vectors. An expression vector encoding a transduction domain of this invention may further comprise a sequence encoding a cargo peptide or polypeptide that will be fused with the transduction domain. To produce a recombinant fusion protein, a cargo sequence is fused with the transduction domain sequence and expressed as a polypeptide chain. A cargo polypeptide may be heterologous to either or both of the SP and CIS. The transduction domain sequence can be engineered by inserting a CIS into an SP-containing protein sequence (e.g., of naturally secreted protein) through gene manipulation (e.g., DNA cloning) whereby the secretion signal is homologous to the cargo polypeptide and the CIS is heterologous. Alternatively, such an expression vector may be one that is adapted for subsequent insertion of a sequence encoding such a cargo peptide or polypeptide such that expression of the resulting vector will result in production of a fusion protein containing both the transduction domain and the cargo peptide or polypeptide.

Various embodiments of this invention provide a fusion protein for use in transduction into a target cell, the fusion protein comprising a cargo peptide portion intended for delivery into a cell, the cargo portion optionally being adapted to be complexed with another cargo component; the fusion protein further comprising, in a direction toward its N-terminus from the cargo portion: a cleavage inhibition peptide, an optional linker and a secretion signal peptide; or the fusion protein comprises in a direction towards its C-terminus from said cargo portion: said secretion signal peptide, the optional linker and the cleavage inhibition peptide. Superior transduction efficiency is achieved when the sequence of the secretion signal peptide precedes the sequence of the cleavage inhibition peptide, in the N to C-terminus direction.

Various embodiments of this invention provide nucleic acids encoding a fusion protein of this invention, vectors comprising such a nucleic acid and host cells comprising such nucleic acids and vectors.

Various embodiments of this invention provide a method of preparing a transduction agent comprising joining a transduction domain of this invention to a cargo molecule to be delivered into a target cell. The method may comprise such joining by chemical means or by expressing a fusion protein of this invention. When such a fusion protein of this invention is expressed in a cell, the method may further comprise recovering the expressed protein from the cell. Recovery from the cell may involve recovery from a membrane fraction of the cell. The method may further comprise joining an additional cargo component to such a fusion protein after said recovery.

Various embodiments of this invention provide a method of introducing a cargo molecule into a cell using a transduction agent of this invention. All or part of the cargo molecule may be a peptide or polypeptide. The method comprises contacting the target cell with a transduction agent of this invention, including a fusion protein of this invention optionally joined to another cargo component. The target cell may be a mammalian cell.

In various embodiments of this invention, a secretion signal peptide referred to has the sequence of a "complete secretion signal", as described herein.

Various embodiments of this invention provide methods for selecting target cells or tissue as a recipient of a transduction agent according to this invention, as well as methods for selecting an appropriate signal peptide sequence for use with a particular target cell, wherein a transduction domain or fusion protein of this invention is contacted with a cell and a determination made as to whether transduction occurs. Such a determination may be carried out by detecting or measuring the presence of a compound delivered to the inside of the cell as a result of transduction mediated by a transduction domain or fusion protein of this invention.

DESCRIPTION OF THE FIGURES

FIGS. 3A-C are charts showing design of fusion protein structural genes using different transduction domain sequences that were described in the prior art. The fusion proteins (amino acid sequences listed) were expressed and purified for comparing the relative efficiency of intracellular protein delivery.

FIG. 4 is a chart showing sequences of the oligonucleotide primers used in construction of the PTM-GFP-Fc fusions.

FIG. 5 is a chart showing intracellular uptake of GFP-Fc protein fused to different transduction domains based on relative intensity under green fluorescence microscopy of cell cultures.

FIG. 6A) iPTD-GFP-Fc can quickly disperse and enter a population of cells. This rapid rate of internalization of fusion proteins is estimated by counting the number of cells with green fluorescence at defined time interval for incubation and followed by trypsinization of the recipient cell surface. FIG. 6B) Rate of reaching the equilibrium or completion of intracellular protein transduction is estimated by measuring the level of green fluorescence intensity of individual single cells as a function of incubation time interval followed by trypsinization of the recipient cell surface. FIG. 6C) The level of the iPTD-GFP-Fc fusion protein delivery into cells is in correlation with concentration of the fusion protein in the cell culture media. FIG. 6D) At approximately 10-20 ug/ml concentration, the iPTD-GFP-Fc fusion protein efficiently disperses and enters every single cell.

FIG. 7 is a chart showing intracellular delivery of the iPTD-GFP-Fc fusion protein into a variety of human cell types, detected by direct visualization of green fluorescence under fluorescence microscope.

FIG. 8 contains photographic representations showing intracellular protein transduction using iPTD-GFP-Fc with trypsinization of the recipient cell surface. Intracellular distribution and subcellular localization of the iPTD-GFP-Fc fusion protein is directly visualized using confocal 3-dimensional LASER scanning microscopy.

DETAILED DESCRIPTION AND EXEMPLARY EMBODIMENTS

Figure 1:
FIG. 1 is a chart showing design of a fusion protein structural gene, and identity of the purified recombinant fusion protein produced in cells. SP1: secretion signal peptide sequence; GFP: green fluorescence protein; Fc: IgG1 fragment crystallizable; TAT: the cationic cluster region of HIV-1 transactivator of transcription. The arrow that points right after the SP domain indicates the signal peptidase cleavage site.

This invention provides for specificity in the covalent linkage between a transduction domain and a cargo molecule. This is established through gene design and protein engineering using recombinant fusion protein technology. A transduction domain which functions as a fusion tag is recombinantly expressed together with a cargo polypeptide as a single polypeptide chain. This invention can allow for efficient delivery of large proteins (such as a glyco-protein complex of about 120 kD) which have been traditionally difficult to administer into cells using conventional protein transduction techniques.

Secretion Signal Peptide

During protein synthesis in a ribosome, an emerging secretion signal peptide sequence specifically forms a complex with a signal recognition particle, which recognizes a signal receptor particle receptor and then targets the entire complex (the ribosome-nascent chain complex) to a translocon in the endoplasmic reticulum membrane. The signal recognition particle is then released, allowing the nascent peptide chain to enter translocon and into endoplasmic reticulum. Inside the endoplasmic reticulum, the signal sequence is typically cleaved off by a membrane-bound signal peptidase.

Signal peptidases are enzymes that convert secretory and some membrane proteins to their mature form by cleaving off their N-terminal targeting signal sequence (see, Paetzel et al., (2002), Chem. Rev., 102, 4549). Signal peptidase and complex subunits can be found in prokaryotes and as well as in the protein import machinery of mitochondria, chloroplast, and endoplasmic reticulum in eukaryotes. Secretory signal peptidases are primarily serine proteases that cleave signal peptides from translocated precursor proteins at the extracytoplasmic site of membrane (see, Paetzel et al., (2002), Chem. Rev., 102, 4549). The mammalian signal peptidase is an integral membrane protein complex, and is composed of multiple subunits (see, Evans et al., (1986), Proc. Natl. Acad. Sci. U.S.A., 83, 581; Bohni et al., (1988), J. Cell. Biol., 106, 1035). Purified peptidase complex from dog pancreas microsomes contain 5 polypeptides, which vary in molecular weight from 12000 to 25000. The subunits of a mammalian signal peptidase complex are termed according to their molecular weight, such as SPC12, SPC18, SPC21, SPC22/23, and SPC25 (see, Evans et al., (1986), Proc. Natl. Acad. Sci. U.S.A., 83, 581.) In chicken, homologs of these 5 signal peptidase complex (SPC) subunits have also been identified (see, Paetzel et al., (2002), Chem. Rev., 102, 4549). In yeast the signal peptidase complex is also composed of protein homologs with sequence identity to those found in mammalian cells (see, YaDeau et al, (1991), Proc. Natl. Acad. Sci. U.S.A., 88, 517; Meyer and Hartmann, (1997), J. Biol. Chem., 272, 13159). The essential catalytic subunit responsible for cleaving the N-terminal signal sequence of nascent protein to their mature form is the 21 kD protein (SPC18 or SPC21 in mammals, and SEC11 in yeast) (see, Bohni et al., (1988), J. Cell. Biol., 106, 1035.) While other subunits of signal peptidase complex are not essential for signal sequence cleavage, they are involved in the stabilization of the catalytic subunit and formation of complex to the translocation complexes and downstream pathways in cellular membrane. In addition to the signal peptidases in endoplasmic reticulum, a diverse group of signal peptidase can also be found in mitochondria, chloroplasts, and bacteria. In eukaryotes, subcellular organelles also have specific signal peptidases that process the signal peptides off proteins destined to the intermembrane space in mitochondria or chloroplast. These ubiquitous peptidases play a vital role in the cleavage of signal peptides that target the protein to the correct subcellular destination.

Secretion signal peptides do not have sequence homology, but are highly conserved in function. It is remarkable that native cellular machineries can specifically and correctly recognize signal sequences that have no conservation of sequence (see, Matoba S and Ogrydziak DM, (1998), J. Biol. Chem., 273, 18841; Rothe C and Lehle L, (1998), Eur. J. Biochem., 252, 16).

Surprisingly, signal sequences that show no conservation of sequence, are specifically and correctly recognized with fidelity for essential functions in cells. Alignment of known sequences of signal sequence does reveal a general structural topology. Naturally occurring secretion signal peptides generally begin within about 10 residues from the N-terminus and may be from about 10 to 80 and typically from about 13 to 30-36 amino acids in length. They typically have three conserved domains, an amino terminal domain that includes hydrophobic residues and optionally one or more basic residues (such as Arg and Lys (see: Von Heijne, G. and Abrahmsen, L., FEBS Lett. 244:439); a central hydrophobic domain that typically comprises from 6 to about 15 residues (with preference for leucine and/or alanine), and a carboxy-terminal domain that contains a signal peptidase processing determinant and a peptidase cleavage site and typically contains polar and uncharged amino acids. Typically, the residues −3 and −1 to the cleavage site are small and neutral (e.g. Ser, Ala, Gly or Val).

The N-terminal positively charged (basic) residues of a signal peptide sequence establish electrostatic interaction with negatively charged phospholipid headgroups. The central hydrophobic core spans membrane lipid bilayers and many form an alpha-helix. The carboxy-terminal residues immediately before the cleavage site are typically conserved features in naturally occurring signal peptides for recognition and processing by a signal peptidase and/or a complex on a membrane surface. Signal sequences are remarkably tolerant of amino acid substitutions (see, Von Heijne G, (1985), FEES Lett., 190, 1; Valent et al., (1995) EMBO J., 14, 5494; Zheng N and Gierasch LM, (1996), Cell, 86, 849).

Synthetic signal peptides are also known, including truncated secretion signal sequences which retain the central hydrophobic region but are void of a peptidase cleavage site (for example, see US 2010/0197598).

This invention makes use of all secretion signal peptides that are capable of penetrating cellular membranes, including those described as "importation competent signal peptide" in U.S. Pat. No. 5,807,746 and those that are chemically synthesized (for example, see U.S. Pat. Nos. 6,043,339 and 6,841,535; published US application US2010/0197598; Lin et al. (1995), J. Biol. Chem., 270, 14255; and Chaloin et al. (1998), Biochem. Biophys. Res. Commun., 243, 601). For example, all the secretion signal sequences employed in the Examples below (including those used for comparison purposes) are contemplated for use in this invention.

Secretion signal peptides for use in this invention may that include sufficient C-terminal domain such that the secretion signal will be functional in a signal peptide mediated pathway in a cell (referred to herein as a "complete secretion signal"). The secretion signal peptide sequence used in some embodiments herein are full length amino acid sequences (including those from the N-terminal portion of secreted endoplasmic reticulum proteins, lysosomal proteins, and transmembrane proteins) which are capable of being recognized by the trafficking system that delivers such proteins to the cell's extracellular environment.

The examples below show that truncation mutation of the signal peptide sequences before the peptidase cleavage site can decrease intracellular protein transduction efficiency but may still provide enhanced efficiency over conventional methods provided that it is immediately followed by cleavage inhibition sequence. This indicates that the native biological function of a signal sequence in directing peptide biosynthesis and/or process through different sub-cellular locations in a cell may be more important than the structural or sequence characteristics of the secretion signal peptide identified in the prior art (for example, see published US application 2010/0197598; and U.S. Pat. No. 6,841,535.) Thus, use of native, full length secretion signal sequence that can execute a native biological function of a signal peptide in a cell can provide further advantages. Nevertheless, variants of native sequences containing modifications (such as mutations, deletions/truncations, and/or additions/insertions) that retain transduction competency, including those which retain such biological function of the signal peptide are suitable for use as a secretion signal sequence component in this invention.

Hydrophobicity alone is not sufficient enough to access a signal peptide-mediated secretion pathway (see, Matoba S and Ogrydziak DM, (1998), J. Biol. Chem., 273, 18841; Rothe C and Lehle L, (1998), Eur. J. Biochem., 252, 16) and the results presented in Example 2 below also show that hydrophobicity itself alone is not sufficient enough to fully enhance intracellular protein delivery. Thus, mutations that increase the overall hydrophobicity in a signal sequence but which adversely weaken access to the signal peptide-mediated secretion pathway, are not preferred (see, Matoba S and Ogrydziak DM, (1998), J. Biol. Chem., 273, 18841).

Various sequences of secretion signal peptides are available from databases such as SIGPEP (see: vonHeijne [1987] Protein Sequence Data analysis 1:41-42 and [1989] FEBS Letters 224:439-446) and on the Internet, such as at: http://www.signalpeptide.de or http://proline.bic.nus.edu.sg/spdbl. Secretion signal peptide sequences including the cleavage site can be predicted from the sequence of such proteins by a number of computational methods known in the art, including those on the SignalP World Wide Web server (http://www.cbs.dtu.dk/services/SignalP).

Cleavage Inhibition Sequence

It is widely accepted that a secretion signal peptide sequence will be cleaved and removed by post-translational modification processes in a cell during biosynthesis and maturation of the protein. As a result, use of a secretion signal peptide as an N-terminal tag in recombinant proteins has been considered impractical and use of a functional secretion signal peptide as a fusion tag on a recombinantly expressed protein in a cell has been unrecognized. We generated a reporter protein containing the essential basic domain of the HIV-1 TAT (SEQ ID#03; also see: U.S. Pat. No. 5,804,604). Almost all of the expressed fusion protein resided inside the cell. This observation was previously reported by others (see for example: Shaw et al. (2008), Biochemistry, 47, 1157; Flinterman et al. (2009), Mol. Ther., 17, 334; Koutsokeras and Kabouridis (2009), Biochim. Biophys. Acta., 1790, 147; and Shen et al. (2011), Mol. Ther., 19, 903). However, none of the latter documents described purification or verification of the expressed protein. Furthermore, it was reported that such a fusion combination (termed "SP1-TAT" herein) is furin-sensitive, leading to cleavage of the HIV-1 TAT domain in Golgi apparatus during secretion, explaining entrapment of the expressed protein inside the expression host (see, e.g., Flinterman et al. (2009), Mol. Ther., 17, 334).

We undertook an investigation of the expressed protein and developed purification methods to isolate it to homogeneity. The identity of the protein was revealed by sequencing, as described in the following examples. Surprisingly, the purified protein (which was expressed from a gene construct having combined a secretion signal sequence (SEQ ID#1) and a HIV-1 TAT basic domain (SEQ ID#3) as a fusion protein (SEQ ID#7)), contained an intact secretion signal peptide sequence. The HIV-1 TAT sequence was found fused to the reporter protein as a single polypeptide chain. In solution, this construct is a protein complex with an estimated molecular weight of approximately 120 kD.

The following examples show that a secretion signal sequence (SEQ ID#1) in combination with a HIV-1 TAT (SEQ ID#3) fused to a protein exhibit surprisingly better intracellular delivery efficiency than the same protein with just the secretion signal sequence (SEQ ID#1) fused at its C-terminus The present invention also has the potential for increasing availability or accessibility of a transduced cargo inside a recipient cell. Compared to use of conventional transduction domains (e.g., HIV-1 TAT, poly Arg/Lys) which mediate cargo delivery primarily through endosomes (with >99% of cargo compounds being getting destroyed in the lysosomal pathway; see: Wadia et al. (2004), Nat. Med., 10, 310; Lee et al. (2008), J. Am. Chem. Soc., 130, 2398), various embodiments of this invention appear to mediate cargo protein delivery through microsomal vesicles, which are continuously cycled and recycled. This allows for gradual release of the cargo to find its way to a destined subcellular location.

We recognized that use of a cleavage inhibition peptide sequence in combination with a secretion signal peptide sequence will halt secretion, leading to production of full length fusion proteins containing the secretion signal sequence. A cleavage inhibition sequence component for use in this invention comprises amino acid residues that are positively charged under physiological condition (pH 6-8) including Arg and Lys. Such components include (but are not limited to) HIV-1 TAT (shown in SEQ ID#3), and sequences with arginine repeats (for example, SEQ ID#5). The sequence may have the formula $(XXX)_1 (YYY)_n$ where each X is Pro, Arg or Lys, each Y is Arg or Lys and $\eta$ is $\geq 1$.

Cleavage inhibition sequence components for use in this invention do not necessarily have sequence homology, yet they inhibit cleavage of a secretion signal peptide sequence and further, may inhibit secretion of the protein, resulting in its accumulation inside the cell expressing the matter. A single residue of lysine or arginine, placed immediately next to a secretion signal sequence, is a cleavage inhibition sequence. Two adjacent residues of lysine and/or arginine in tandem repeat, or two distant residues of lysine and/or arginine with one of the lysine/arginine residues placed immediately next a secretion signal peptide in sequence, is also a cleavage inhibition sequence. A single residue of proline, placed next to a secretion signal sequence and immediately after a signal peptidase cleavage site, can be a cleavage inhibition sequence (for example see, Nilsson and Heijne (1992) FEBS Lett., 299, 243; Barkocy-Gallagher and Bassford (1992) J. Biol. Chem., 267, 1231). However, for the resultant protein to be more efficient in cargo delivery, it is preferable that the cleavage inhibition sequence component comprise a plurality of 4 or more lysine or arginine residues arranged in tandem repeat.

For the production of this invention in bacteria, a single residue of proline placed adjacent to the secretion signal sequence and after the signal peptidase cleavage site, is a cleavage inhibition sequence. Two adjacent residues of proline in tandem repeat, or two distant residues of proline with one proline placed adjacent to the secretion signal peptide, is also a cleavage inhibition sequence. There is no absolute upper limit for the number of proline residues in the cleavage inhibition sequence, and no absolute upper limit for the size of the cleavage inhibition sequence. One of the prolines is preferentially placed immediately after the secretion signal peptide, in sequence. For the transfection agent to be particularly efficient in cargo protein delivery, the cleavage inhibition sequence component should contain at least two proline residues and preferably, an additional 4 or more adjacent lysine and/or arginine residues in tandem repeat, placed after proline or proline cluster (preferably immediately after the proline/proline cluster).

For the production of the invention in mammalian cells, a single residue of lysine or arginine, placed adjacent to the secretion signal sequence, is a cleavage inhibition sequence. Two adjacent residues of lysine and/or arginine in tandem repeat, or two distant residues of lysine and/or arginine with one of the lysine/arginine placed adjacent to the secretion signal peptide in sequence, is also a cleavage inhibition sequence. For the transfection agent to be particularly efficient in cargo protein delivery, the cleavage inhibition sequence component should contain a plurality of 4 or more adjacent lysine and/or arginine residues in tandem repeat, placed adjacent the secretion signal peptide. There is no absolute upper limit for the number of lysine and/or arginine residues in such a cleavage inhibition sequence and no absolute upper limit for the size of the cleavage inhibition sequence. Preferably one of the lysine and/or arginine residues is placed immediately next to the secretion signal peptide, in sequence. Examples of lysine and/or arginine clusters useful as cleavage inhibition sequences in this invention include the basic domain of HIV-1 TAT, poly arginine, poly lysine, and the cation-rich domains of nuclear localization sequences.

Linker Sequence

An optional linker (preferably of no more than about 7 amino acid residues) may be employed between the secretion signal peptide and the secretion inhibition peptide sequences. We found that extending the number of amino acids between the secretion signal peptide sequence and the cleavage inhibition sequence gradually attenuates the function of the cleavage inhibition sequence, leading to increased proportion of secretion signal peptide being cleaved and the secretion of fusion protein to culture media. While it may be preferable for any spacer to be omitted between the secretion signal and the cleavage inhibition sequence, a linker that contains amino acid residues that enhances inhibition effect of the cleavage inhibition sequence component and/or enhances signal peptide recognition or function can be advantageously employed.

Synthesis

A transduction domain of this invention may be prepared synthetically and joined or linked to a cargo molecule using any suitable methodology. However, this invention also prefers recombinant production of a transduction agent containing a peptide based cargo compound.

Overall Design and the Cargo Protein Structural Gene

To produce a recombinant fusion protein, a cargo sequence is fused with the transduction domain sequence and expressed as a polypeptide chain. A cargo polypeptide may be heterologous to either or both of the SP and CIS. The transduction domain sequence can be engineered by inserting a CIS into an SP-containing protein sequence (e.g., of naturally secreted protein) through gene manipulation (e.g., DNA cloning) whereby the secretion signal is homologous to the cargo polypeptide and the CIS is heterologous.

The combination of a secretion signal peptide and a cleavage inhibition sequence is preferentially located at a terminal end (N- or C-terminus) of any protein construct of this invention. However, protein delivery efficiency is dependent on the relative orientation and disposition of the secretion signal sequence and the secretion inhibition sequence components. When these components are placed at the N-terminus of a protein, the secretion signal peptide sequence should precede a linker sequence (if used), and be immediately followed by the cleavage inhibition sequence (for example, see SEQ ID#7, 33, 37, and 43). When these components are placed at the C-terminus of a protein, the secretion signal peptide sequence preferably precedes the linker sequence (if used), and is immediately followed by the cleavage inhibition sequence. When the relative disposition of secretion signal sequence and cleavage inhibition sequences are reversed (such as shown in SEQ ID#35), delivery efficiency can decrease to a level equivalent to that of conventional transduction methodologies (as shown in the following examples). Such preference in relative disposition and orientation of the sequence components indicates that our invention is enabled by a specific recognition process involved in the intracellular transduction event rather than biochemical based interaction and cellular entry mediated by the amphipathic nature of having CIS and SP together. This is in contrast to the conventional methods that are independent of direction and relative orientation of hydrophobic and hydrophilic sequence components.

The cleavage site and the active site of a signal peptidase complex must be in sufficient proximity (and be properly aligned on the membrane surface) for efficient cleavage of a signal peptide (see, Jain et al. (1994) J. Biol. Chem., 269, 16305). Lengthening the carboxy-terminal region of a signal peptide between the cleavage site and the hydrophobic core region (Jain et al. (1994) J. Biol. Chem., 269, 16305) appears to make the cleavage site inaccessible to a signal peptidase. Without being bound to a theory, it appears that an alteration in structure and conformation at the carboxy-terminal region of a signal peptide by presence of the cleavage inhibition peptide according to this invention also makes the cleavage site inaccessible to a signal peptidase complex. Further, the positively charged cleavage inhibition sequence may provide greater affinity for negatively charged phospholipids on a membrane surface which could also contribute to enhanced cargo delivery. Thus, cellular aspects that may be affected by presence of a cleavage inhibition sequence in this invention are the membrane, the signal peptide complex and other associated molecular machineries in the signal peptide processing pathway.

Affinity Purification Tags and Protease Cleavage Sequences for Removal of a Tag

Affinity tags may be appended to or be part of a cargo peptide, polypeptide or protein employed in this invention so that the resulting product can be purified from a crude biological source using affinity purification methods. In the examples shown below, the Fc region of an IgG antibody was utilized as an affinity purification tag for Protein A chromatography purification of a Fc-containing fusion protein. Other protein affinity tags that can be used will be known to those of skill in the art. Addition of a protease recognition sequence as a linker between an affinity tag and a cargo component will allow for the affinity tag to be cleaved by digestion with an endo-peptidase and removed by affinity chromatography. An example is the use of SUMO1 protein which is cleaved at its C-terminus by the SENP1 protease found in the nucleus of mammalian cells.

Plasmid Construction

Standard recombinant nucleic acid methods can be used to express a genetically engineered recombinant protein. In one embodiment, a nucleic acid sequence encoding a protein of this invention is cloned into a nucleic acid expression vector with appropriate regulatory control sequences for transcription and translation.

In order to obtain high level of expression of a cloned gene or nucleic acid (such as a cDNA encoding the fusion protein) the coding sequence may be subcloned into an expression vector that contains a strong promoter for directing transcription, a transcription/translation terminator, and, in the case of a nucleic acid encoding a protein, a ribosome binding site for translational initiation. Inducible promoters can be used, including metal-responsive promoters. Suitable promoters are well known in the art and are described, e.g., in Sambrook & Russell, Molecular Cloning: A Laboratory Manual, 3rd Edition, Cold Spring Harbor Laboratory, N.Y. (2001), and Ausubel et al., Current protocols in Molecular Biology, Greene Publishing Associates and Wiley Interscience, N.Y. (1989). The construct can be introduced into an appropriate host cell, e.g., a bacterial cell, yeast cell, insect cell, mammalian cell, or tissue culture cells. A nucleotide sequence encoding a protein of this invention may be prepared (synthesized/amplified/purified) in a replicative vector (e.g., plasmid or virus) for transfection or transformation into expression cell hosts. Eukaryotic expression systems for mammalian cells, yeast, and insect cells are well known in the art and are also commercially available. The construct can also be introduced into embryonic stem cells to generate a transgenic organism as a model subject. Kits for expression systems are commercially available.

The cargo peptide may including any polypeptide or protein that functions as an enzyme, transcription factor, or cell growth regulator that may be included as a therapeutic agent to treat a genetic disease or cancer. An example is the tumor suppressor protein, P53 (see, Levine (1997) Cell, 88:323; Phelan et al. (1998) Nat. Biotechnol., 16:440), which may be fused to a protein transduction domain of the present invention, to induce programmed cell death in a target cell.

Expression and Purification of Recombinant Fusion Proteins

Host cells suitable for producing recombinant proteins include bacterial cells and eukaryotic cells (e.g., fungal, insect, plant, and mammalian cells). Host cells can be disrupted by any conventional method, including freeze-thaw cycling, sonication, mechanical disruption, or the use of cell lysing agents. The reference: "Guide to Protein Purification", 2nd Edition, Methods in Enzymology, Volume 463, Academic Press (2009), describes a number of general methods for purifying recombinant (and non-recombinant) proteins. The methods can include, e.g., ion exchange chromatography, size-exclusion chromatography, affinity chromatography, selective precipitation, dialysis, and hydrophobic interaction chromatography. These methods can be adapted to devise a purification strategy for the cell permeable recombinant protein. If a recombinant protein includes a purification handle, such as an epitope tag or a metal chelating sequence, affinity chromatography can be used to purify the protein efficiently.

Stabilization of Fusion Proteins in Aqueous Solution

The combination of a secretion signal sequence and a cleavage inhibition sequence allows for expression of a fusion protein containing a cargo polypeptide and an intact secretion signal peptide. This product is trapped inside the cell and is found membrane-associated when differential centrifugation of a lysate of the cell is carried out. Because of the membrane-spanning ability of the secretion signal sequence component, the recombinant protein appears to become a monotopic membrane protein anchored onto membrane lipids through the intact secretion signal peptide sequence. Those of skill in the art are familiar with protein purification that facilitate the extraction and stabilization of membrane proteins from different cell types.

Development of appropriate purification methods to isolate a particular protein of this invention in soluble and stable form begins with identification of stabilizers capable of extracting the fusion protein from the membrane lipid into solution, and maintaining its solubility in aqueous solution. The stabilizer can be a single or combination of chemical compounds (e.g., salts, ionic strength, pH, buffers, sugar, excipient, cryo-protectant, preservatives as additives) that increase solubility of hydrophobic and insoluble proteins. As shown in the examples below, amphiphiles (e.g., compound possessing both hydrophobic and hydrophilic groups) such as, but not limited to, detergents may be utilized in purification of the fusion protein. Detergents that may be utilized to best advantage include the gentle/mild nonionic detergents (e.g., Triton X100™, Tween-20™, NP-40, Octylglucoside, Decyl-maltoside, and Dodecyl-maltoside) and zwitterionic detergents (e.g., LDAO™, CHAPS™, Zwittergent 3-10™, Zwittergent 3-12™, and Zwittergent 3-14™)

While all detergents employed in the examples herein were successful in membrane extraction and purification of a fusion protein, advantageous membrane extraction of a fusion protein was carried out with Zwittergent 3-12™, and then CHAPS™, on Protein A chromatography. However, other combination of detergents are also possible without affecting intracellular delivery efficiency of the fusion protein.

The amount of recombinant fusion protein produced can be evaluated by detecting the cargo or an affinity tag directly (e.g., using Western analysis) or indirectly (e.g., by assaying an activity associated with the fusion protein). Protein can be detected prior to purification, during any stage of purification, or after purification. Protein purity can be determined (for example) by SDS-PAGE.

Particular embodiments of the present invention can be made using pCDNA-3.1 (Invitrogen, Calif.) as an expression vector which comprises a polynucleotide encoding a recombinant protein including an enhanced green fluorescent protein (eGFP) as a reporter and an antibody fragment crystallizable region (Fc) as a specific affinity purification tag. Insertion of a polynucleotide encoding a transduction domain according to the present invention into the vector, 5' and/or 3' to the eGFP-Fc gene of the vector enables expression of a recombinant fusion protein incorporating the eGFP-Fc. The recombinant fusion protein is membrane-associated in the expression host HEK293. Cell membrane containing the fusion protein may be isolated using sedimentation fractionation from cell lysate, extraction with Zwittergent 3-12™, and purification on Protein A chromatography in which the zwittergent 3-12™ is replaced with CHAPS, prior to elution.

Use of Transduction Domains and Transduction Agents

Target cells and tissues may be selected according to their ability to recognize a transduction domain of this invention. Alternatively, the transduction domain may be designed or chosen according to recognition of the signal peptide sequence by a desired target cell. This may be readily determined by methodologies disclosed herein.

The examples below demonstrate that a 120 kD protein (e.g., the SP1-TAT-GFP-Fc homodimer linked by a cysteine disulfide bond) can be efficiently delivered into mammalian host cells. In addition to proteins, short polypeptides and peptides can also be delivered. Virtually any compound that can be covalently linked to a transduction domain of this invention can be contemplated as a cargo including proteins, peptides, antibodies, oligonucleic acids, nucleic acids, inorganic molecules, organic molecules, and derivatives of these. Also, a fusion protein of this invention can also function as a carrier for a secondary cargo which can be any such composition that can be covalently linked to the protein. The fusion protein may be used to deliver a covalently linked secondary cargo compound into cells, and then release the secondary cargo through endogenous peptidase activity inside the recipient cell host.

A secondary cargo may consist of, at least in part, a dye (e.g., fluorescin), an antibody, a reporter molecules (e.g., GFP), or a molecule that enhances, inhibits, and/or supplements the activity or inactivity of a cellular or viral polypeptide within a cell. In addition, a cargo can include an antisense molecule and have antisense function.

A compound of interest may be packaged and intracellularly addressed to a specific site depending on the nature of the specific fusion protein components and/or the nature of a delivery cargo linked thereto. Functional assays can be used to monitor effects of compounds delivered into cells.

Solubility of a protein of this invention or such a protein linked to another cargo component may be optimized to avoid aggregation and precipitation. Buffers and solutions of pH 6 to 8 (e.g., close to physiological pH) are preferred. Ionic strength comparable to physiological conditions (e.g., approximately 150 mM NaCl or similar) is preferred. Addition of lipid analogs or amphiphiles (such as detergents) which stabilize a fusion protein in solution may also be employed. To avoid aggregation and precipitation of fusion protein-linked active compounds, stock solutions may be prepared/tested and adjusted to lower or higher level accordingly. For application of the present technology for intracellular delivery, a fusion protein linked active compound may be used at approximately 250 nM.

It is not necessary, although often convenient, to derivatize a protein of this invention prior to delivery, (e.g., where visualizing agents such as dyes are employed). Proteins of this invention can be derivatized (e.g., to other molecular species such as dyes) and still retain a comparable level of intracellular delivery efficiency.

Development of derivatization reactions can be carried out to optimize chemical modification or enzymatic derivatization of fusion protein using routine procedures known to those of skill in the art. For example, those of skill are familiar with protein biochemistry and chemistry that facilitate the chemical and enzymatic reactions and purification of the desired reaction products in solutions.

Methods of analysis can involve any one or combination of a number of assays including, but not limited to, gel retardation assays, affinity binding assays, quasielectric light scattering, circular dichroism, NMR, fluorescence quenching, FTIR spectroscopy, efficiency of intracellular delivery into a target cell, specific subcellular localization of a fusion protein linked active compound (e.g., effectiveness of a nuclear localization signal) within a cell, toxicity to a target cell, ability of transport compounds of different size and charge, and ability to adopt a functional and structured conformational state.

Intracellular delivery on to cells of linked active compounds (such as nucleic acid molecules, drugs, peptides, and proteins), can be for research, diagnostic, therapeutic, and/or cosmetic purposes. Introduction of labeled compounds, proteins, and peptides can permit investigation of many cellular processes, of normal and disease-state cells alike, without the introduction of artifacts due to permeabilization of cells and lengthy staining procedures. Linked active compounds can be drugs, nucleic acids, peptides, or proteins that can alter one or more cellular or viral or physiological functions and behaviors. Intracellular delivery of linked active compounds can be experimental, for example, to elucidate cellular processes or to investigate the properties or activities of the compound that is introduced into the cells. Applications in therapeutic and diagnostic applications are also contemplated, where intracellular delivery of a linked structural protein, enzyme, transcription factor, co-factor, inhibitor, activator, and the like, into target cells can be efficiently achieved. For example, the present invention can have therapeutic value for conditions such as, but not limited to, metabolic disorders, genetic diseases or disorders, cancer, inflammation, auto-immune disorders, degenerative disorders (including neurodegenerative disorders), behavioural or psychiatric disorders, and infectious and parasitic diseases, including bacterial and viral infections. The present invention can be used to deliver peptides, proteins, and drugs into cells that, by virtue of their sequence composition or other features (such as, but not limited to the three-dimensional structure, conformation, or glycosylation pattern, or affinity for a receptor, transporter, or certain moiety on an organelle, or specific subcellular structure within a cell), are localized to specific sites within a cell. This can have benefits for experimental studies as well as therapeutic and diagnostic applications.

Drug Discovery

Mixtures of the proteins of this invention linked to active compounds (e.g., from libraries of heterologous compounds, peptides, proteins, or nucleic acids) may be combined and inserted into cells according to this invention and functional assays employed to identify drug candidates having a therapeutic function of interest.

Methods used to assess the therapeutic effect/efficiency of a potential drug candidate (including chemical compounds, nucleic acids, peptides, and proteins, etc.) can be any cellular or biochemical assay. Such assays are well known to those of skill in the art, and include (but not limited to) methods that measure cell growth, cell death; methods that measure secretion of specific molecules; methods that measure endocytosis, phagocytosis; methods that measure bacterial infection, viral infection, and fungal infection; methods that measure activation of intracellular signaling pathways, transcription of specific protein structural gene, translation of specific protein, activity of specific membrane channel protein, cellular metabolism, respiratory activity, photosynthetic activity, and methods that measure cellular response to hormones or cytokines, etc. To facilitate detection of a drug candidate having a desirable effect of interest, this invention may employ optionally incorporated reporter genes or optional genes that express, for example regulators, co-regulators or cofactors. It is also possible to use fusion protein linked drug candidates directly on tissues or whole organisms to screen for desirable therapeutic effects and/or restoration/regaining of health. The results of desirable therapeutic effects can involve morphological, physiological, and psychological changes, and that includes wound healing, reduced tumor size, reduced inflammation, changes in body weight, alteration of behavior, changes in mood, etc.

Nucleic Acid Molecules, Peptides, and Proteins

The present invention includes nucleic acid molecules that contain sequences that encode transduction domains and proteins of this invention. Nucleic acid sequences can be DNA or RNA, and can be single-stranded or double-stranded. Nucleic acid molecules can also comprise additional sequences, including origins of replication, restriction enzyme sites, protein structural gene sequences of interest, peptide gene sequence of interest etc., and can optionally comprise detectable labels (such as, but not limited to, fluorescent proteins or radioactive labels) or specific binding members (such as, but not limited to, biotin, protein affinity tag). Nucleic acid molecules that encode transduction domains of this invention can be useful for generating fusions between peptides or proteins of interest, and as such can be useful in many applications. Nucleic acid molecules that comprise sequences that encode transduction domains can be used as primers. In this aspect, the primers preferably comprise sequences that encode a transduction domain of the present invention adjacent to at least a portion of a sequence of interest. One or more such primers can be used to amplify a nucleic acid sequence of interest, such as with a polymerase, such as, but not limited to thermal stable polymerases typically used in polymerase chain reaction (PCR), such that the amplification product comprises a nucleic acid sequence of interest fused to a sequence encoding the transduction domain. Furthermore, at least one primer used in the amplification reactions can comprise a promoter, a binding site for RNA polymerase and associating complexes, such that the amplification product (e.g., mRNA) can be used for subsequent translation of the sequence of interest fused to the transduction domain.

An expression construct may contain a nucleic acid sequence that encodes the transduction domain and also one or more recognition sites for restriction endo-nucleases or other sequences that can allow insertion or addition of a nucleic acid encoding a sequence (e.g. a cargo polypeptide) of interest. The construct may be designed such that a desired protein/peptide structural gene sequence can be joined to the nucleic acid sequence of the transduction domain, such that expression results in an in-frame fusion between the protein sequence of interest and transduction domain. The construct may also include expression sequences, such as, but not limited to, promoters, enhancers, splice sites, translation initiation or enhancing sequences (such as, but not limited to, Shine-Delgarno sites, Kozak sequences, and IRES sequences), and transcriptional and translational termination sites. The construct may be a DNA construct that is transcribed, and the resulting RNA translated to produce a fusion protein of this invention. The construct can be designed for in vivo or in vitro expression, and can be optimized for prokaryotic or eukaryotic expression systems. Expression systems that produce a fusion protein of this invention and/or a fusion protein of the present invention can be used in any of the applications provided herein, including research and therapeutic applications.

Libraries

In this document, the term "library" refers to a collection of two or more fusion proteins of this invention linked to or which comprise molecules that are known or unknown, such as purified peptides/proteins or those obtained directly from crude preparations. Libraries can also comprise synthetic compounds, optionally made by combinatorial synthesis methods. In this manner, libraries from any source can be used to test on cell cultures and cell types for identifying the leading drug candidates with desirable therapeutic effects.

Libraries used in the methods of the present invention can be the transduction domain linked nucleic acid libraries, and also antisense nucleic acid libraries. Nucleic acid (e.g., DNA, and RNA) can be generated by chemical synthesis or by cloning methods using methods known to those of skill in the art. Proteins of this invention can be covalently linked to a nucleic acid following derivatization reaction and/or crosslinking reaction methods, known to those of skill in the art. Such linked antisense libraries can be used to screen for a desirable effect in silencing one or more regions of genes. In this manner, the antisense libraries can facilitate disruption of a gene leading to the identification of a drug that can alleviate specific pathological phenotype.

Libraries used in the methods of the present invention can also be transduction domain linked peptide libraries, using chemically synthesized peptides or peptides synthesized by in vivo or in vitro translation. One may generate peptide libraries by, optionally, transcription, and translation or nucleic acid libraries. In this manner, after identifying a drug candidate by insertion of active peptides from the library into cells, a specific peptide of interest can be isolated from the peptide library. Furthermore, identification of the specific peptide also allows for generation of a transduction domain linked nucleic acid, from which the therapeutic peptide is derived. In addition, the linked peptide libraries can also be prepared by linking the fusion proteins of this invention to peptide fragments generated by protease digestion of a preparation of one or more proteins that can be known or unknown.

Nucleic acids, peptides, and proteins for use in generating the linked compound libraries of this invention can be derived from systematically and/or totally randomized sequences. Methods of generating randomized nucleotide sequences includes fragmentation of large nucleic acid molecule (e.g., genomic or chromosomal DNA) using direct shearing (e.g., sonication) or enzymatic digestion (e.g., restriction endonucleases). In addition, randomized nucleotide library can be produced by chemical synthesis with and/or without statistical weight to the probability of adding subsequent nucleotide base at any position in the sequence. Similarly, a peptide library can be produced by fragmentation of purified proteins or crude extracts from any cell types. Libraries of short peptides can be produced by chemical synthesis with and/or without statistical weight to the probability of adding subsequent amino acid residue at any position in the sequence. Naturally occurring proteins can be extracted from specific cell types of any given organism, which then can be linked to fusion proteins or transduction domains of this invention followed by screening for desirable therapeutic effects. Proteins of randomized amino acid sequences can also be produced from in vitro or in vivo transcription and translation of a chemically synthesized nucleotide. Examples of such can be found in U.S. 2011/0130346 A1; U.S. 2012/0010124; Cho et al, (2000), J. Mol. Biol. 297:309; Keefe and Szostak, (2001), Nature 410:715; Doi et al, (2005), Protein Eng. Des. Sel. 18:279; and Tanaka et al, (2010), Protein Sci. 19:786. In addition, libraries of protein variants can be generated from specific mutations (e.g, site-directed mutagenesis) and/or random mutations (e.g., directed evolution) of protein structural gene. It may be advantageous to design multiple libraries composed of fewer samples so that once a therapeutic candidate is identified, a library can be further divided into sublibraries until a particular active ingredient is enriched.

Complex Mixtures

Complex mixtures, such as herbal/plant extracts, insect extracts, animal organ extracts, animal body fluid extracts, secretion materials, serum extracts, soil extracts, etc., can also be used as sources of partners for fusion proteins of this invention and the linked materials can be used as libraries to screen for medicinal ingredients from crude extracts. Complex mixture containing nucleic acid, peptide, proteins, lipid, carbohydrate, and chemical compounds can be linked to fusion proteins for insertion into cells for identifying the desirable therapeutic effect of interest. Following identification of drug candidates, libraries can be divided into fractions or sub-libraries or concentrated in further extraction and/or purification procedures/methods to isolate an active compound of interest.

PHARMACEUTICAL COMPOSITIONS

A transduction domain of this invention linked to a therapeutic protein in the form of a single polypeptide chain, can be administered to a subject per se, and/or be present in a pharmacological composition mixed with suitable carrier(s) or excipient(s). Techniques for formulation and administration of drugs may be found in Remington, 2005, "Remington: The Science and Practice of Pharmacy, 21st Edition," Lippincott Williams, the University of the Sciences in Philadelphia.

A wide range of molecules that can have pharmaceutical or therapeutic effects can also be delivered into cells using compositions and methods of the present invention. The molecules can be organic or inorganic. Organic molecules can be peptide, proteins, carbohydrates, lipid, sterols, nucleic acids (including peptide nucleic acids), or any combination thereof. A formulation for delivery into cells can comprise more than one type of molecule, for example, two different DNA sequences, or a protein and a steroid, etc. While recognizing that a protein of the present invention can deliver a wide range of compounds into cells, it is particularly noteworthy that peptide and proteins, including large proteins, can be delivered.

Local delivery of a protein of the present invention complexed with one or more compounds of interest could improve efficiency of delivery to a target cell, while minimizing side effects mediated by nontarget tissues. The compositions of the present invention, being taken up rapidly by cells, have the potential to allow high dosages of therapeutics to be delivered to the site of pathology, while minimizing systemic effects. Such compounds of interest can include, but are not limited to, growth factors, cytokines, enzymes, enzyme inhibitors, or anti-inflammatory peptides such as those that inhibit the effect of, for example, rheumatoid arthritis or other aspects and embodiments described above.

For example, a respiratory pathology, such as asthma, can be treated using compositions of the present invention. Both manual and mechanized inhalation devices known in respiratory therapy, could be used to deliver aerosols comprising therapeutic compounds complexed with fusion proteins of the present invention. Candidate molecules that can be delivered for the treatment of asthma include, but are not limited to inhibitors of phosphodiesterase, tyrosine kinase, and NF-kappaB.

Routes of Administration

Suitable routes of administration may, for example, include oral, rectal, vaginal, transmucosal, or intestinal administration; parenteral delivery, including intramuscular, subcutaneous, intramedullary injections, as well as intratheecal, direct intraventricular, intravenous, intraperitoneal, intranasal, or intraocular injections.

Alternatively, one may administer a pharmaceutical composition of the present invention in a local rather than systemic manner, for example, via injection of the pharmaceutical composition directly into a solid tumor and/or in a depot or sustained release formulation. Local delivery can be performed in various ways, depending on the tissue to be targeted. For example, aerosols containing compositions of the present invention may be inhaled (for nasal, tracheal, or bronchial delivery); compositions of the present invention may be injected into the site of injury, disease manifestation, or pain, for example; compositions can be provided in lozenges for oral, tracheal, or esophogal application; may be supplied in liquid, tablet or capsule form for administration to the stomach or intestines, may be supplied in suppository form for rectal or vaginal application; or may even be delivered to the eye by use of creams, drops, or even injection. Formulations containing compositions of the present invention complexed with therapeutic molecules can even be surgically administered, for example, in association with a polymer or other structure or substance that can allow the compositions to diffuse from the site of implantation to surrounding cells. Alternatively, they can be applied surgically without the use of polymers or supports.

Formulations that promote penetration of the epidermis for topical delivery are known in pharmacology. Compositions of the present invention can also be used to advantage, for example for the delivery of peptides, proteins, and other molecules that curtail pain, itching, or inflammation or that have antiviral, antibacterial, or antifungal effects to the skin.

Composition/Formulation

Pharmacological compositions of the compounds and the physiologically acceptable salts and prodrugs thereof are embodiments of this invention. Pharmacological compositions of the present invention may be manufactured by processes well known in the art; e.g., by means of conventional mixing, dissolving, granulating, dragee-making, levigating, emulsifying, encapsulating, entrapping or lyophilizing processes.

Pharmacological compositions for use in accordance with the present invention may be formulated in conventional manners using one or more physiologically acceptable carriers comprising excipients and auxiliaries which facilitate processing of the active compounds into preparations which can be used pharmaceutically. Generally, the choice of formulation is dependent upon a chosen route of administration.

For injection, compounds of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

Formulation that promote penetration of the epidermis are known in pharmacology, and can find use in the treatment of many skin conditions, such as, but not limited to, psoriasis and fungal infections. Formulations that promote penetration of the epidermis and underlying layers of skin are also known, and can be used to apply compositions of the present invention to, for example, underlying muscle or joints. In some preferred therapeutic embodiments, formulation comprising compositions of the present invention that deliver compounds for alleviating rheumatoid or osteo-arthritis can be administered by applying a cream, ointment or gel to the skin overlying the affected joint.

For oral and parenteral administration of the linked compound of this invention, the drug may be formulated using pharmaceutically acceptable carriers known in the art in production of (for example) tablets, pills, dragees, capsules, liquids, gels, syrups, slurries, suspensions and the like. Pharmacological preparations for oral use can be made with the use of a solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbital; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores may be used with suitable coatings. For this purposes, concentrated sugar solutions may be used, which may optionally contain gum Arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or characterize different combinations of active compound doses.

Pharmacological compositions which can be used orally include push-fit capsules made of gelatin, as well as soft, sealed capsules made of gelatin and a plasticizer, such as glycerol or sorbitol. The push-fit capsules can contain the active ingredients in a mixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may be taken in the form of tablets or lozenges formulated in conventional manner. For the small peptides and complexes of the invention, this may prove useful.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichloro-tetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflators may be formulated containing a powder mix of the compound and a suitable powder base such as lactose or starch.

The compositions may be formulated for parenteral administration by injection, e.g., by bolus injection or continuous infusion. In this way it is also possible to target a particular organ, tissue, tumor site, site of inflammation, etc. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmacological compositions for parenteral administration include aqueous solutions of the compositions in water soluble form. Additionally, suspensions of the compositions may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compositions to allow for the preparation of highly concentrated solutions.

Alternatively, one or more components of the composition may be in powder form for constitution with a suitable vehicle, e.g., sterile pyrogen-free water, before use.

The compositions may also be formulated in rectal compositions such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil), or as part of a solid or semi-solid implant that may or may not be auto-degrading in the body, or ion exchange resins, or one or more components of the composition can be formulated as sparingly soluble derivatives, for example, as a sparingly soluble salt.

The pharmacological compositions herein also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Dosage

Pharmacological compositions of the present invention include compositions wherein the active ingredients are contained in an amount effective to achieve its intended purpose. More specifically, a therapeutically effective amount means an amount of compound effective to prevent, alleviate or ameliorate symptoms of disease or prolong the survival of the subject being treated.

Determination of a therapeutically effective amount is within the capability of those skilled in the art, especially in light of the detailed disclosure provided herein. For any compound used in the methods of the invention, the therapeutically effective amount or dose can be estimated initially from cell culture assays. For example, a dose can be formulated in animal models to achieve a circulating concentration range that includes the IC50 as determined in cell culture (where inhibitor molecules are concerned). Such information can be used to more accurately determine useful doses in humans.

Toxicity and therapeutic efficacy of a composition of the present invention can be determined by standard pharmaceutical procedures in cell cultures or experimental animals, e.g., for determining the LD50 (the dose lethal to 50% of the population) and ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from those cell culture assays and animal studies can be used in formulating a range of dosage for use in human. The dosage may vary within this range depending upon the dosage form employed and the route of administration utilized. The exact formulation, route of administration and dosage can be chosen by the individual physician in view of the patient's condition. (See e.g., Remington, 2005, "Remington: The Science and Practice of Pharmacy, 21st Edition," Lippincott Williams, the University of the Sciences in Philadelphia.).

The amount of composition administered will, of course, be dependent on the subject being treated, on the subject's weight, the severity of the affliction, the manner of administration and the judgment of the prescribing physician.

Packaging

A pharmaceutical composition of the present invention can be supplied such that one or more transduction domain linked active compounds are in the same or different containers, and may be in solution, in suspension, or in powder form. Various packaging options are possible, depending at least in part on whether one or more compounds of this invention and optionally, one or more delivery, solubilizing, flavoring, or suspending agents are to be provided together or separately, and upon the route and mechanism of administration. For example, where active compounds are supplied separately, the compositions may, if desired, be presented in a pack having more than one chamber, and in which a barrier can be ruptured, ripped, or melted to provide mixing of the linked active compounds. Alternatively, two separately provided linked active compounds can be mixed in a single, separate container, optionally with the addition of one or more other carriers, solutions, etc. One or more unit dosage forms containing the active ingredient can be provided in a pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label could include treatment of a tumor, inhibition of angiogenesis, treatment of fibrosis, diabetes, retrovirus-mediate ailments, and the like. Furthermore, the invention is ideally suited to gene therapy, either to deliver (indirectly via gene insertion) a desired protein of interest, or else to supply an antisense molecule to control the expression of a gene of interest.

Dermatological and Cosmetic Compositions

One or more linked drugs or therapeutic agents of this invention can be administered for cosmetic purposes. A linked compound can be mixed with suitable carriers or excipients. A wide range of molecules that can be used for cosmetic purposes can be delivered into cells using compositions and methods of the present invention. The molecules can be organic or inorganic. Organic molecules can be peptides, proteins, carbohydrates, lipids, sterols, nucleic acids (including peptide nucleic acids), or any combination thereof. A formulation for delivery into cells can comprise more than one type of molecule, for example, two different DNA sequences, or a protein and a steroid, etc.

In most cases, dermatological or cosmetic formulations comprising compositions of the present invention can be applied topically. Formulations that promote penetration of the epidermis (the dead outer layer of the skin) are known in pharmacology. In some cases, penetration of the outer layer of the skin can be enhanced by chemical or laser "stripping" or "peeling" or microabrasion, techniques that are currently used to remove the outer layer of skin and promote rejuvenation. It is also possible to inject a dermatological or cosmetic formulation of the present invention into, or just below, the skin. This can be appropriate when the formulation is to be targeted to a specific site, or efficient penetration below the dermis is desirable.

The technology of the present invention can be used to advantage the delivery of peptide, proteins, and other molecules to live skin cells to promote cosmetic effects. For example, healing of wounds, abrasions, or scars can be promoted by the introduction of cell division promoting agents (for example, cell cycle regulators, transcription factors, or small molecules such as retinoids) to cells at the site of the lesion.

Other cosmetic aspects are also considered, such as the introduction into skin cells, or cells immediately underlying the skin, of compounds of interest that can reduce or increase oil secretion, or increase the production of collagen or other extracellular matrix molecules to reduce wrinkling or "sagging" of skin, etc.

Cosmetic formulations of the present invention can optionally include penetration agents, can include substances that allow the formulation to be applied evenly to the skin, such as oils, lipids, or polymers that allow for dispersal or "smoothing" of the formulation, can include pigments, can include botanical extracts, can include "moisturizers", sunscreen compounds, acids (such as, but not limited to, alpha-hydroxy or beta-hydroxy acids), chelators, etc.

A dermatological or cosmetic formulation of the present invention can be packaged in any appropriate manner. For example, it can be provided in a package that comprises more than one container, such that one or more linked compounds can optionally be provided separately, and can optionally be mixed with enhancing compounds (e.g., carriers) before application. The packaging can optionally facilitate mixing, for example, by allowing the formulations to mix by puncturing, tearing, or melting a barrier between the formulations, or removing a barrier between the formulations by unscrewing, pulling a tab, etc. In addition, additional formulations can be provided separately from the iPTD-linked active compounds, including one or more other liquids, powders, lotions that can comprise, for example, sunscreens, penetration agents, salves, or other cosmetics that are to be applied before, after, or at approximately the same time as the transduction domain linked compounds. Instructions for administration can be included in the package, or with one or more of the containers.

The following examples will serve to further illustrate the present invention without, at the same time, however, constituting any limitation thereof. On the contrary, it is to be clearly understood that resort may be had to various other embodiments, modifications, and equivalent thereof which, after reading the description herein, may suggest themselves to those skilled in the art without departing from the spirit and/or scope of this invention.

Example 1

While there are many methodologies for bringing proteins from the extracellular environment across the membrane lipid bilayer into cells, the efficiencies and specificity associated with those methodologies have been unsatisfactory. The cationic cluster of HIV-1 TAT domain and variants constitute a well known family of protein transduction domains (PTD). However, their use in protein drug development has found very little success primarily due to the lack of transduction efficiency especially for large proteins.

Cell penetrating peptides based on secretion signal sequence are another family of peptide delivery vectors, but their application is hindered by dissociation and re-association with unspecific cargo molecules. The intracellular delivery of proteins fused to a secretion signal sequence as a recombinant single polypeptide chain has not been exploited, and this is because during the biosynthesis and maturation of protein, the secretion signal sequence is cleaved and removed by post-translational modification processes in cells.

In this example, we show that both cleavage and secretion of a protein containing a secretion signal sequence can be stopped by including a cleavage inhibition sequence in the design of fusion protein's structural gene. Such an approach has been unrecognized in the art (for example, see: Shaw et al. (2008), Biochemistry, 47, 1157; Flinterman et al. (2009), Mol. Ther., 17, 334; Koutsokeras and Kabouridis (2009), Biochim. Biophys. Acta., 1790, 147; and Shen et al. (2011), Mol. Ther., 19, 903). This discovery makes possible generation (e.g., expression, purification, and production) of full length fusion proteins containing uncleaved secretion signal sequences.

In this example, green fluorescent protein (GFP) fused to a C-terminal IgG1 Fc affinity tag (as shown in FIG. 1) was used as a reporter cargo protein for the ease of detection and efficiency quantitation (e.g., kinetic measurement with fluorescence-coupled flow cytometry, FACS, confocal microscope imagining of the host cells), and purification. All the GFP-Fc constructs carried a secretion signal peptide sequence derived from the human placental alkaline phosphatase signal peptide (SP; SEQ ID#1) at the N-terminus of a GFP-Fc structural gene (as shown in FIG. 1). It was hoped that recombinant fusion proteins would be secreted and could then be used to compare intracellular protein delivery efficiency of HIV-1 TAT (SEQ ID#3) fused to the N- and C-termini of the GFP-Fc structural gene. The constructs were transfected into mammalian expression host cells HEK293. During expression, the protein products of the SP1-GFP-Fc and SP1-GFP-Fc-TAT constructs (GFP-Fc and GFP-Fc-TAT fusion proteins, respectively) were found outside in the cell culture media indicating secretion occurred. The secreted GFP-Fc and GFP-Fc-TAT were purified to homogeneity on Protein A affinity chromatography column. The expression product of the SP1-TAT-GFP-Fc construct was found predominantly inside the cell and very little amount could be detected in the cell culture media by Western Blot analysis. The same observation was previously reported by others (see, e.g., Shaw et al. (2008), Biochemistry, 47, 1157; Flinterman et al. (2009), Mol. Ther., 17, 334; Koutsokeras and Kabouridis (2009), Biochim. Biophys. Acta., 1790, 147; and Shen et al. (2011), Mol. Ther., 19, 903). However, we then developed a purification protocol to isolate the protein to homogeneity, and identify its structure.

Adherent HEK293 cells expressing intracellular SP1-TAT-GFP-Fc were collected and washed with PBS (phosphate buffer saline). Following cell lysis using ultrasonication, the cell lysate was separated by sedimentation fractionation. The expressed protein product of the SP1-TAT-GFP-Fc construct was found in the membrane particulate fraction, indicating membrane association. Initially, detergent solubilization of the fusion protein from SP1-TAT-GFP-Fc construct was carried out using Triton X100™ followed by purification on Protein A chromatography. However, the extraction efficiency of Triton X100™ and its ability to maintain SP1-TAT-GFP-Fc in solution was weak, resulting in some aggregation and precipitation. Alternative purification methods including utilization of other detergents were tested to provide a method suitable for the purification and stabilization of SP1-TAT-GFP-Fc.

Figure 2:
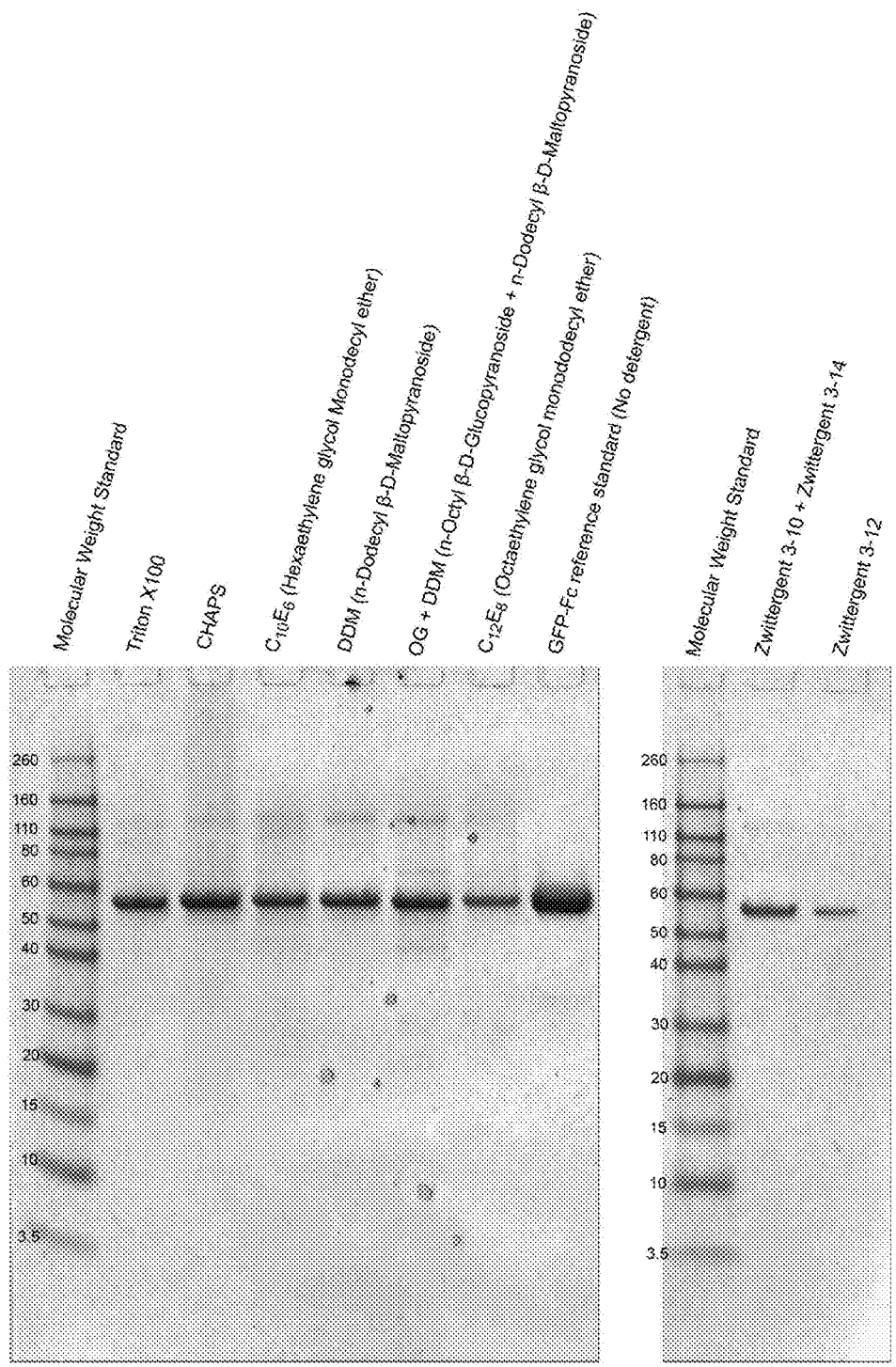
FIG. 2 is a photographic representation of a SDS-PAGE gel (stained with Coomassie Blue). Purity of the SP1-TAT-GFP-Fc fusion protein is shown with the single polypeptide chain of ~60 kD molecular weight on SDS-PAGE under reducing condition. SP1-TAT-GFP-Fc was expressed in cells and purified from the membrane fraction with different detergents (as indicated and labeled in each lane) on Protein A chromatography.

Amphiphiles such as detergents have the ability to disrupt cellular membrane that are held together by hydrophobic interactions. However, amphiphiles that disrupt membrane bilayers can also disrupt hydrophobic interactions that contribute to the stability of globular proteins, leading to denaturation and inactivation of desired protein products. In the present example, mild/gentle detergents commonly used in purification of proteins were employed and these included nonionic detergents (Triton X100, NP-40, Tween-20, n-Octyl-β-D-glucopyranoside, n-Decyl-β-D-maltopyranoside, n-Dodecyl-β-D-maltopyranoside, C8E4, C10E9, C10E6, C12E8) and zwitterionic detergents (zwittergent 3-8, zwittergen 3-10, zwittergen 3-12, zwittergen 3-14, CHAPS). To facilitate screening of different detergents used in the purification of the SP1-TAT-GFP-Fc protein product, equal amount of membrane particulate was used in detergent solubilization and followed by Protein A chromatography purification. FIG. 2 shows Commassie-stained SDS-PAGE for the SP1-TAT-GFP-Fc protein product purified in the presence of different detergents. The functionality of the purified fusion protein (the green fluorescence of GFP) was assessed in fluorescence spectrophotometer to quantify the emission intensity of green fluorescence and to determine the specific activity of the purified fusion protein. The results in Table 1 show that Zwittergent 3-12, Zwittergent 3-10 and CHAPS are among the best amphiphiles for purifying the SP1-TAT-GFP-Fc protein product, giving high specific activity, indicating that Zwitterionic detergent can efficiently extract the membrane bound SP1-TAT-GFP-Fc without inactivating the GFP and Fc functions (e.g, in green fluorescence emission and in purification, respectively). N-terminal protein sequencing using Edman Degradation method on the SP1-TAT-GFP-Fc protein product confirmed that the purified fusion protein has an intact secretion signal peptide sequence on the N-terminus.

TABLE 1

| Detergent | GFP Green Fluorescence Intensity (AU) | Total Protein Present (µg) | Specific Activity (AU/µg) |
| --- | --- | --- | --- |
| GFP-Fc Standard (no detergent) | 470 | 8.5 | 55 |
| Zwittergent 3-10 + Zwittergent 3-14 | 892.5 | 18 | 49.6 |
| Zwittergent 3-12 | 612 | 25.6 | 23.8 |
| CHAPS | 1560 | 140 | 11.1 |
| C12E8 | 1260 | 127.8 | 9.9 |
| C10E6 | 990.5 | 94 | 10.5 |
| Dodecyl Maltoside (DDM) | 634 | 127.3 | 5 |
| Decyl Maltoside (DM) | 841 | 134.4 | 6.26 |
| Octyl Glucoside (OG) + Dodecyl Maltoside (DDM) | 976 | 141.5 | 6.9 |
| Triton X100 | 656 | 100 | 6.56 |

Verification of the purified recombinant fusion protein with an intact secretion signal peptide sequence produced in cell represented the first ever demonstration of the use of HIV-1 TAT as an inhibitor to block cleavage of a secretion signal peptide and halt secretion of a fusion protein produced in cells. Purification and identification of the full length SP1-TAT-GFP-Fc not only showed the intracellular localization of fusion proteins produced from gene constructs that have a secretion signal peptide followed by a HIV-1 TAT protein transduction domain, but also provided the recognition that the functionality of a secretion signal peptide sequence can be inhibited in the post-translational modification process of a cell. In addition, utilization of amphiphiles such as detergents, in solubilization of proteins with exposed hydrophobic sequences, allows various signal peptides (which otherwise share little sequence identity) to be utilized as protein transduction domains. In the prior art, peptide vectors were confined to peptide sequence combinations soluble in aqueous solution, limiting the utilization to the sequences. As a result, an additional feature that is presented by embodiments of this invention is that as a secretion signal peptide sequence with strong hydrophobic characteristics (which would become increasingly difficult to synthesize due to solubility) can be generated as part of a single polypeptide chain in cells and is an answer to some technical challenges encountered in peptide synthesis.

Experimental Procedures

All PCRs (polymerase chain reaction) for amplification of nucleotide gene sequence are carried out using the high-fidelity PFU Ultra II DNA polymerase from Stragagene. Amplified PCR products were purified on Agarose gel (1% w/v) electrophoresis, and extracted using Qiagen's QIAquick gel extraction kit. The structural gene of GFP (SEQ ID#50) and Fc (SEQ ID#52) were optimized for mammalian expression and synthesized at MrGene™ in the vector pMA. Cloning of SP1-GFP-Fc, SP1-TAT-GFP-Fc, and GFP-Fc-TAT:

The structural gene sequence of SP1-GFP-Fc was assembled from three individual DNA fragments, produced by PCR. A human placental alkaline phosphatase signal peptide (SEQ ID#2) sequence was PCR amplified by using synthesized oligonucleotide DNA as a template (SEQ ID#2) and the forward and reverse oligonucleotide as primers (SEQ ID#67 and 68, respectively). The N-terminus of the signal peptide sequence was engineered to include a Not I restriction site followed by Kozak sequence, and the C-terminus of the SP sequence is engineered to have a Sac I restriction site for the convenience of down-stream subcloning. The modified signal peptide was named SP1. The GFP gene fragment was PCR amplified by using the synthesized GFP gene sequence as a template (SEQ ID#50), and the forward and reverse oligonucleotide DNA as primers (SEQ ID#69 and 70, respectively). The PCR primers for the GFP gene fragment were engineered to include a Sac I and EcoRI at the 5' and 3' end of GFP structural gene sequence, respectively. The Fc structural gene (SEQ ID#52) was engineered to have a EcoR1 restriction site at the 5' end, and an Xho1 restriction site, which was added immediately after three translational stop codons, at the 3' end, and the Fc gene fragment is prepared by subcloning (restriction digestion with EcoR1 and Xho I) from the Fc gene-containing plasmid, synthesized at MrGene™. The PCR products were digested with respective restriction enzymes: SP1 DNA fragment was digested by Not I and Sac I, GFP DNA by Sac I and Eco RI, Fc DNA by Eco RI and Xho I. Through a series of subcloning work, SP1-GFP-Fc was finally inserted in expression vector pcDNA3.1(+). The sequence was confirmed by restriction mapping and sequencing analysis. This construct was expressed to produce the secreted GFP-Fc that served as a negative control in the protein transduction assay.

The structural gene sequence of SP1-TAT-GFP-Fc was assembled from four individual DNA fragments. First, the SP1 gene was engineered to have the Not I site at the 5' end and the Xma I at the 3' end using the synthesized SP1 gene (SEQ ID#2) as a template and the designed PCR forward and reverse oligonucleotide DNA as primers (SEQ ID#71 and 72, respectively). The HIV-1 TAT basic domain sequence fragment was produced by PCR amplification method annealing two synthesized oligonucleotides primers (forward and reverse, SEQ ID#73 and SEQ ID#74, respectively). The resulting PCR product of HIV-1 TAT basic domain had an Xma I restriction site at the 5' end, and a Sac I site at the 3' end. The GFP gene fragment was PCR amplified by using the synthesized GFP gene sequence as a template (SEQ ID#50), and the forward and reverse oligonucleotide DNA as primers (SEQ ID#75 and 76, respectively). The PCR primers for GFP gene fragment were engineered to include a Sac I and EcoRI at the 5' and 3' end of GFP structural gene sequence, respectively. The Fc structural gene (SEQ ID#52) was engineered to have a EcoRI restriction site at the 5' end, and an Xho1 restriction site, which was added immediately after three translational stop codons, at the 3' end. The Fc gene fragment was prepared by subcloning (restriction digestion with EcoRI and Xho I) from the Fc gene-containing plasmid, synthesized at MrGene'. The PCR products were digested with respective restriction enzymes: SP1 DNA fragment was digested by Not I and Xma1, TAT DNA fragment was digested by Xma I and Sad, GFP DNA by Sac I and Eco RI, Fc DNA by Eco RI and Xho I. Through a series of subcloning work, SP1-TAT-GFP-Fc was finally inserted in expression vector pcDNA3.1(+). The sequence was confirmed by restriction mapping and sequencing analysis. The GFP-Fc-TAT structural gene was constructed by subcloning and replacing (restriction and ligation) the corresponding Fc* fragment in the SP1-GFP-Fc structural gene with the DNA fragment containing the Fc*-TAT sequence (SEQ ID#58) released (restriction digestion) from pMA vector. The synthesized Fc* sequence fragment was produced by subcloning the C-terminal Fc fragment from the Xma1 restriction site that is located within the full length Fc sequence. The Fc*-TAT gene (SEQ ID#58) in pMA was synthesized at MrGene™, and was engineered to have the Xma1 and Xho1 at the 5' and 3' ends, respectively. The Fc*-TAT gene fragment then replaced the corresponding fragment in the SP1-GFP-Fc structural gene, and the resultant gene sequence of SP1-GFP-Fc-TAT was finally cloned into a vector termed "pCMV-Neo". The sequence was verified by restriction mapping and DNA sequencing analysis. The arrangement of the TAT transduction domain, signal peptide sequence, and eGFP-Fc fusion protein domains are shown in FIG. 1 for the GFP-Fc, SP1-TAT-GFP-Fc, and GFP-Fc-TAT fusion protein constructions. All three fusion proteins carrying an N-terminal signal peptide sequence were intended to be processed and secreted into the extracellular environment.

Expression of GFP-Fc, SP1-TAT-GFP-Fc, GFP-Fc-TAT Fusion Proteins:

The three recombinant expression plasmids pcDNA3.1 (+)/SP1-GFP-Fc, pcDNA3.1(+)/SP1-TAT-GFP-Fc, pcDNA3.1(+)/TAT-GFP-Fc and pCMV-Neo/SP1-GFP-Fc-TAT were prepared by using Qiaprep spin mini-columns. The plasmid concentration was 0.5-0.9 ug/ul, ratio of 260 nm/280 nm absorbance>1.80. HEK293 cells were routinely cultured in DMEM containing 10% Heat-inactivated FBS, 2 mM Glutamine, penicillin/streptomycin. Twenty-four hours before transfection, HEK293 cells were sub-cultured into a 6-well plate in antibiotics-free complete DMEM. When transfection was conducted, the cell confluence was about 70-80%. Pure plasmid DNA of 2 micrograms for each construct was transfected into a well of a 6-well plate using Roche's FugenHD of 6 microliters. 16 hours after transfection, the transfected cells were sub-cultured in diluted concentration×200, ×400, ×800 and grew in complete DMEM containing 1 mg/ml G418. Stable cell clones with strong green color under fluorescent microscope were picked up around 2 weeks after adding antibiotics G418.

The constructed plasmids, which were confirmed by restriction mapping and DNA sequencing, were transfected into HEK293 cells for selection (Roche FuGene Transfection Kit). Cells were grown at 37° C. incubator supplemented with 5% carbon dioxide (v/v). Single cell expressing high levels of fusion protein, characterized by the appearance of intense green fluorescence upon UV radiation, were selectively isolated for growth propagation in nutrient rich tissue culture DMEM supplemented with fetal bovine serum, glutamine, and penicillin and streptomycin.

All three fusion proteins GFP-Fc, SP1-TAT-GFP-Fc, and GFP-Fc-TAT were constitutively expressed. The adherent HEK293 host cells expressing the fusion proteins were grown on tissue culture dishes in DMEM media supplemented with fetal bovine serum, glutamine, and penicillin and streptomycin.

For convenience of protein purification, the adherent HEK293 cells at 80% confluence level were washed with prewarmed (37° C.) phosphate buffer saline (Fisher), and replaced with fresh C-SFM-II cell/serum free media (Invitrogen), to which the expressed and processed GFP fusion proteins accumulate.

For secreted proteins (which included GFP-Fc and GFP-FC-TAT) equal amount of cells were incubated in serum-free medium SFM-II for 72 hours. The supernatant was collected and subjected to protein A chromatography purification of the fusion protein. For non-secreted proteins (which included SP1-TAT-GFP-Fc and TAT-GFP-FC) equal amount of cells were incubated in complete DMEM for 72 hours. The cell lysate was collected and analyzed by SDS-PAGE and Western Blot. The protein samples were loaded for 15 ul per lane for secreted proteins and 10 ug total proteins per lane for non-secreted proteins. All the samples were treated in both reducing and non-reducing conditions. The protein bands were then blotted onto PVDF membrane. Primary antibody rabbit-anti GFP IgG in 5000 dilution was used to probe expressed proteins, secondary antibody goat-anti rabbit IgG conjugated with HRP in 5000 dilution was used to probe primary antibody. ECL method was used to detect the signals exposed to X-ray films.

Purification of GFP-Fc and GFP-Fc-TAT Fusion Proteins:

Serum free media containing expressed GFP-Fc and GFP-Fc-TAT fusion proteins was harvested, and centrifuged to produce a clarified aqueous supernatant. The clear supernatant was filtered through 0.22 micron membrane to remove small size debris before loading onto the Protein A chromatography resins (Genscript, Piscataway, N.J.). Fusion proteins carrying the Fc domain were specifically adsorbed to Protein A in the chromatography resin, and purified from the cell culture media. The fusion proteins, eluted with 100 mM citrate (pH 3.0), are immediately neutralized with Tris buffer. The purified protein fractions were subsequently buffer exchanged to PBS (pH 8.0), and concentrated in a 30 kD molecular weight cut-off Centricon (Millipore, Billerica, Mass.). The protein purity was at least 95% as judged from SDS-PAGE with Coomassie Blue staining. High purity GFP-Fc and GFP-Fc-TAT was obtained using this method.

Purification of SP1-TAT-GFP-Fc Fusion Proteins:

Surprisingly, the expressed SP1-TAT-GFP-Fc (as shown in FIG. 1) wasn't secreted into the growth media, despite carrying an N-terminal signal peptide (which was directly followed by the TAT sequence). Subcellular fractionation of the HEK293 host cells carrying the expressed fusion protein revealed that SP1-TAT-GFP-Fc was localized in the membrane fraction. Amphipathic detergents effective in disrupting phospholipid bilayer structures and increasing the solubility of membrane proteins were used in the purification of SP1-TAT-GFP-Fc and SP1-TAT-linked fusion proteins.

7 grams of wet HEK293 cell pellet were re-suspended in 40 mL (final volume) of Cell Lysis Buffer [150 mM NaCl, 20 mM K/Na/HP042-(pH 8.0), 2 mM EDTA (pH 8.0)]. Prior to lysis, sonicator probe was cooled with ice/cold water. The cells were lysed using the cooled sonicator (Branson Sonifier 250; sonication parameter: 50% duty cycle per pulse, do the 30-seconds sonication pulse for 10 times with cooling of the sonicator probe on ice between pulses). Insoluble material was spun in 50 ml-size conical tubes (1000 rpm/10 minutes/10° C.). When the low speed centrifugation was done, a pipette was carefully used to transfer the cloudy supernatant to a 25-mL size Ultracentrifuge tube. The ultracentrifuge tubes were balanced to 2 decimal places, and spun at 100,000×g (70Ti rotor, use 45,000 rpm/60 minutes/10° C.) [Beckman Optima XL100k]. When Ultracentrifugation was done, the supernatant was removed and the ultracentrifuge tube rinsed without disturbing the membrane jelly. A spatula was used to carefully scrape out the membrane jelly into a 1.5 ml-size Eppendorf tube which was stored at −80° C. The procedures described below apply to 0.70 grams of membrane jelly as starting material in the purification. For this amount of membrane jelly, approximately 200 mL of Membrane Extraction Buffer was used. A Potter homogenizer cooled on ice was used to homogenize the 0.70 grams of membrane jelly in 10-15 mL of Membrane Extraction buffer (0.5% (w/v) Zwittergent 3-12, 500 mM NaCl, 50 mM Glycine (pH 10.0)), using 100 strokes. The well-dispersed homogenate was combined with the remaining extraction buffer (total volume will be 200 mL), and mixed for another 30 minutes followed by ultracentrifugation to pellet down the residual membrane (Balanced to 2 decimal places and spun at 100,000×g; 45Ti rotor; use 40,000 rpm/60 minutes/10° C.). The supernatant was poured into a beaker, and 20 mL phosphate neutralization solution [500 mM of NaH2PO4, 750 mM of NaH2PO4/K2HPO4 (pH 8.0)](1/10th of the Extraction Volume) added, mixed and loaded onto a Protein-A column (1CV.550 microliter). A low-pressure peristaltic pump (e.g., Pharmacia P-1, Multiplier at 10, Speed setting points at or between 3-4) was used to deliver the sample onto a Protein A column. After all the sample had passed through, 20 mL of Wash Buffer No. 1 (0.5% (w/v) Zwittergent 3-12, 500 mM NaCl, 20 mM TrisHCl (pH 7.5)) was passed through. After this was done, 20 mL of Wash Buffer No. 2 [0.5% (w/v) CHAPS, 150 mM NaCl, 20 mM TrisHCl (pH 7.5)] was passed through.

Five 1.5 mL size Eppendorf tubes, each with 400 microliters of Neutralization buffer [0.5% (w/v) CHAPS, 150 mM NaCl, 1M TrisHCl (pH 9.0)] were prepared. 1 mL of Elution buffer [0.5% (w/v) CHAPS, 150 mM NaCl, 100 mM Citrate (pH 3.0)] was applied onto the resin surface using just the right amount of pressure to force elution to occur. After 1 mL had passed through, mixing ensured good neutralization followed by the second fraction, and another 1 mL of Elution buffer. This process was repeated until five fractions were collected. Usually, all the protein was in the first fraction (1.4 mL total). A 4-mL size 30 kD MWCO Millipore Centricon was used with the first fraction (1.4 mL), and topped-up with Exchange Buffer [0.5% (w/v) CHAPS in PBS—Phosphate Buffer Saline (pH 8.0)]. Total volume in the concentrator was around 5 mL. It was spun at 3500 rpm/5 minutes/8° C. After 5 minutes, the content of the concentrator was mixed to prevent precipitation at the bottom of the concentrator. This was repeated until only −250 microliters remained. The concentrator was topped-up with Exchange Buffer [0.5% (w/v) CHAPS in PBS buffer (pH 8.0)] and spun at 3500 rpm/5 minutes/8° C. After 5 minutes, mixing and spinning was repeated until only −150 microliters was left in the concentrator. The SP1-TAT-GFP-Fc was purified to at least 90% purity as judged based on SDS-PAGE stained with Coomassie Blue.

Protein Sequencing of SP1-TAT-GFP-Fc:

The identity of the purified fusion protein was confirmed by Western Blot analysis with anti-GFP antibody. Purity of the fusion proteins was analyzed on SDS-PAGE with Coomassie Blue dye staining. N-terminal protein sequencing of the purified SP1-TAT-GFP-Fc (carried out at IOWA State University—Protein Facility) revealed that the signal peptide at the N-terminus of TAT sequence domain was intact, and the full signal sequence still remains covalently linked to SP1-TAT-GFP-Fc. The sequenced amino acid residue sequence from SP1-TAT-GFP-Fc corresponded to the N-terminal amino acid residues in the signal peptide.

Example 2

Here, we show that the transduction domain described in Example 1 is particularly useful for intracellular delivery of a large protein. A number of well known protein transduction domains were fused to GFP-Fc as recombinant fusion proteins, produced and purified for comparison in transduction assays. We determined the structure-activity relationship with a set of fusion protein variants in which sequences of secretion signal peptide and secretion inhibition components were truncated, mutated, rearranged and/or re-oriented in creating different combinations of transduction domain fused to the N- or C-terminus of GFP-Fc. Here, we show that the present technology can provide effective/efficient delivery of large proteins into cells, and be used for developing protein therapeutics.

Figure 3C:
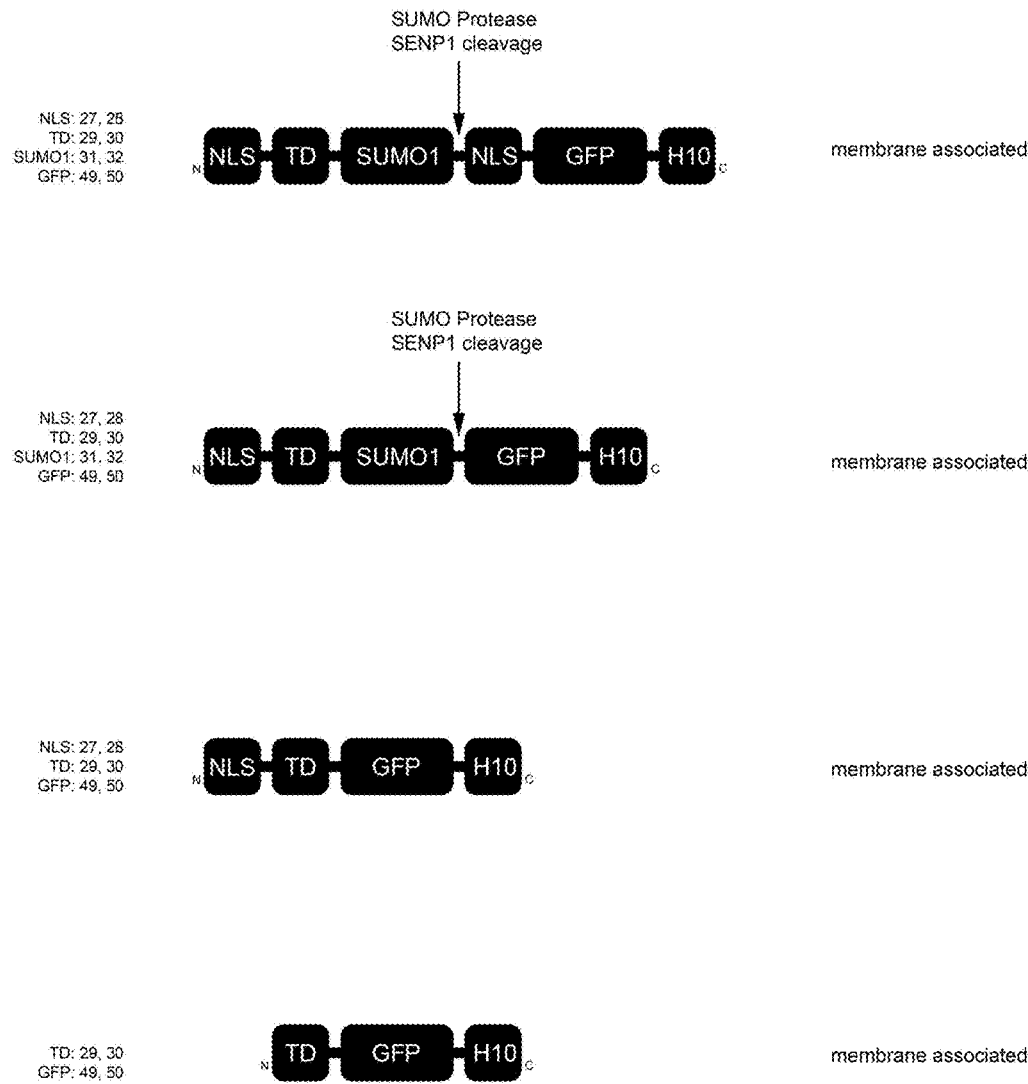
Figure 6A:
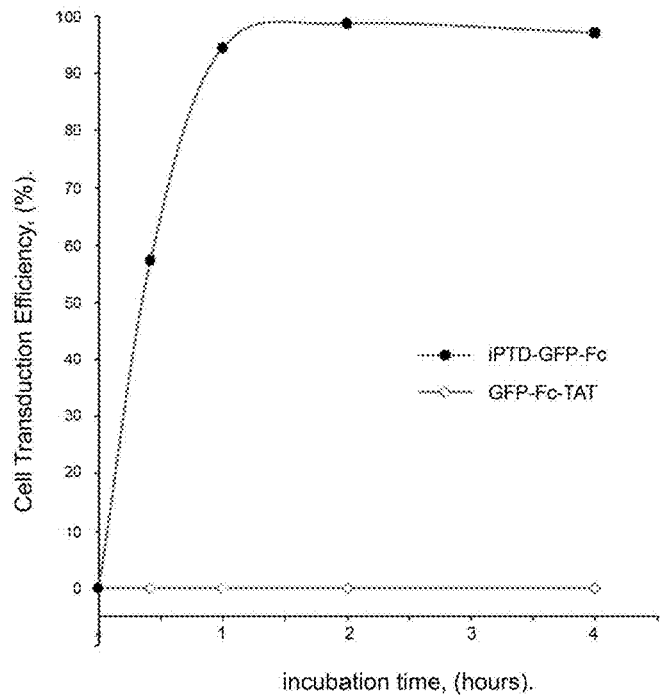
FIGS. 6A-D are graphs comparing kinetics of fusion protein delivery [SP1-TAT-GFP-Fc (termed "iPTD-GFP-Fc") and GFP-Fc-TAT] into cells.
Figure 6B:
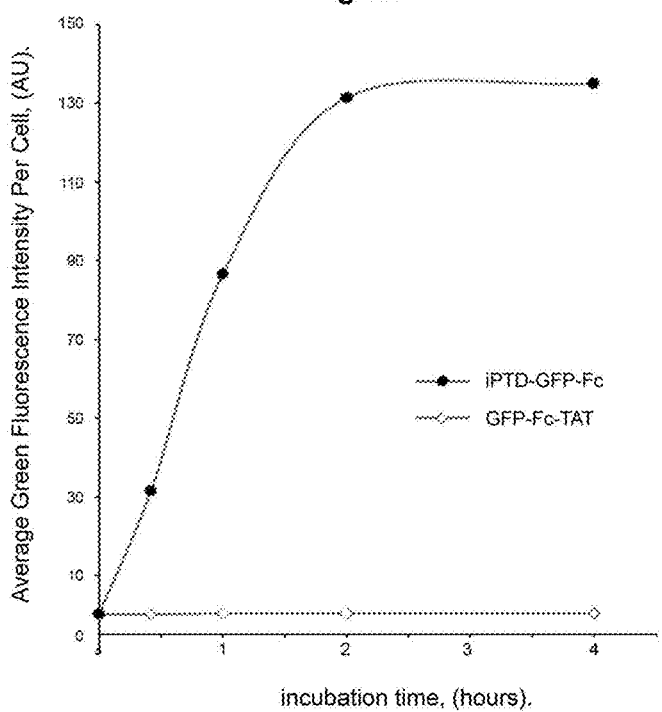
Figure 6C:
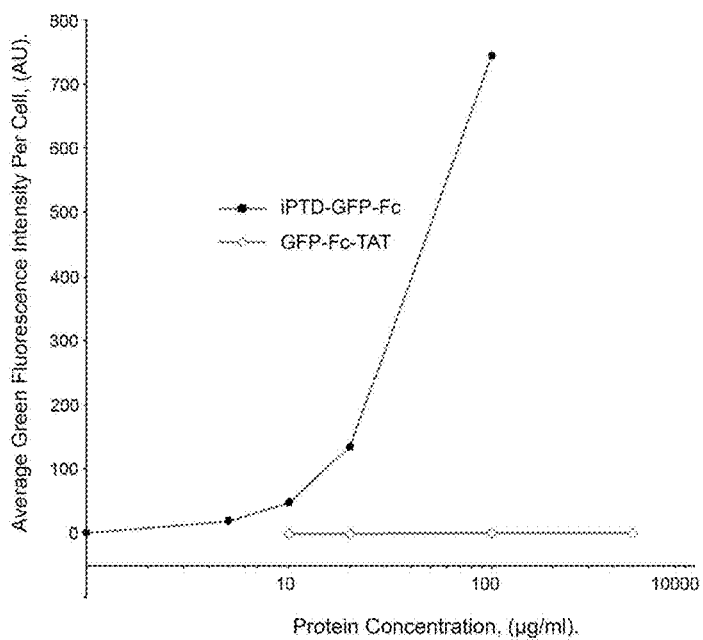
Figure 6D:
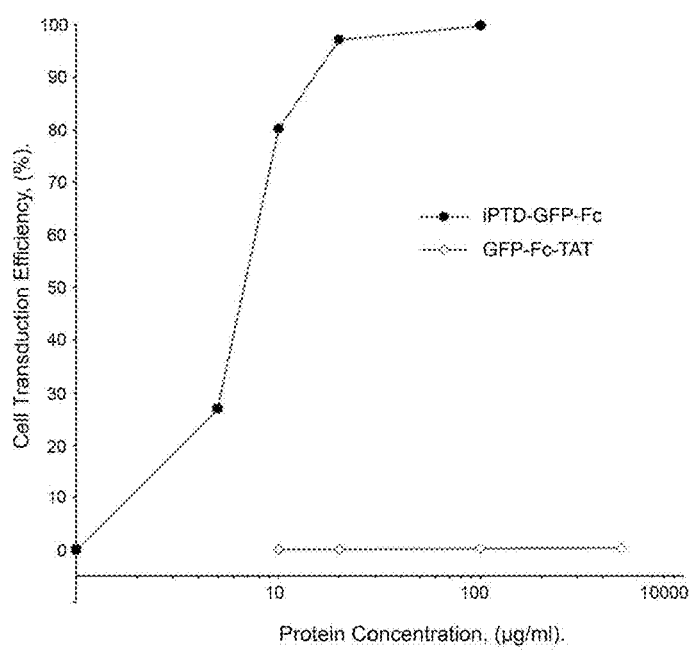

Comparison to Other Protein Transduction Domains (Pics, FACS, Kinetics):

Transduction domain sequences used in this comparison (shown in FIGS. 3A-C) included the signal peptide of human fibroblast growth factor 4 splice isoform (PTM-1; SEQ ID#10; see, U.S. Pat. No. 6,043,339); the hydrophobic core of signal peptides (PTM-4, 5, and 6; SEQ#15, 16, and 17, respectively; see, U.S. 2010/0197598); HIV-1 TAT (SEQ ID#03; see, U.S. Pat. No. 5,804,604); amphipathic peptide (PTM-2 and 3; SEQ ID#11 and 13, respectively; see, U.S. Pat. No. 6,841,535 B2, and U.S. Pat. No. 6,780,846 B1, respectively), and the third helix of the Antennapedia homeodomain (PTM-7; SEQ ID#21; see, Derossi et al., (1996) J. Biol. Chem., 271, 18188-18193]. Transduction efficiency of the GFP-Fc cargo protein was measured by presence (visual comparison on fluorescence microscope) and level of GFP green fluorescence taken up by the cells. Recipient HELA cells were incubated with the fusion proteins for 2 to 3 hours and followed by trypsinization of cell surface-attached fusion proteins. The cells preferentially took up the SP1-TAT-GFP-Fc fusion protein as compared to the conventional transduction domains, as directly visualized on fluorescence microscopy (FIG. 5). Under the same parameters/conditions, an intracellular protein transduction assay (10-30 µm/ml of fusion proteins incubated with confluent adherent HELA cells in vitro) was also carried out. Efficiency of intracellular delivery of the fusion protein of the present invention as determined by FACS was 1000-fold better than those of fusion proteins carrying the HIV-1 TAT domain. Kinetic characterization of SP1-TAT-GFP-Fc (20 µg/ml) using FACS showed that the fusion protein was efficiently taken up by cells in vitro. After 1 hour of incubation and followed by trypsinization of the cell surface removing attached GFP-Fc fusion protein, nearly every single cell had taken up SP1-TAT-GFP-Fc as revealed by FACS analysis (FIG. 6A). After 2 hours of incubation followed by trypsinization, green fluorescence intensity in every single cell had reached the maximum level, indicating that the transduction of fusion protein of the present invention (20 µg/ml) into cells had reached an equilibrium (FIG. 6B) and the HELA cells had stopped taking in anymore. In addition, the level of saturation of fusion protein of the present invention in the HELA recipient cells was dependent on the fusion protein concentration, showing that a higher level of the fusion protein in the culture media correlated with increased depositing of delivered fusion protein in cells (FIGS. 6C and 6D). Under the same conditions, conventional PTDs were not efficient at all at delivering GFP-Fc fusion protein into cells and showed no detectable green fluorescence from inside the cell.

An amphipathic lipid vector (see, U.S. Pat. No. 6,726,894) was successful in bringing about the intracellular delivery of GFP-Fc reporter proteins (FIG. 5). However, the invasive membrane penetration mode of transfection involving the use of excess amount of synthetic lipid to permeablize the cellular membrane was also harmful to the recipient cell hosts. Toxicity associated with the latter technique was shown by an unhealthy cell morphology observed under light microscopy. We also showed that in the presence of serum, the lipid amphiphile vectors failed to deliver GFP-Fc into cells (FIG. 5), suggesting that the lipid amphiphiles are quenched or deactivated in typical cell culture media and unsuitable for therapeutic administration in patients.

In contrast to FACS (which selects single cells for individual fluorescence measurements), fluorescence microscopy provides a sample visualization of the adherent cell cluster as a whole. While FACS revealed that the present invention provided at least 24-fold higher intracellular delivery efficiency than TATS alone, fluorescence visualization of an adherent cell cluster treated with 40-fold more TAT-GFP-Fc for transduction followed by trypsinization still shows a lack of intracellular transduction of green fluorescence fusion protein with TAT (as represented in FIG. 5). This observation implies that when cells are clustered (as they are in vivo) the present invention can be more efficient in passing through a crowded cell mass, accounting for the dramatic difference visualized with fluorescence microscope. This indicates that the present invention not only can provide stronger bioactivity, but also better bioavailablity.

Delivery into Different Cell Types:

In addition to HELA cells, different cell types were tested for intra cellular delivery of fusion protein in vitro. Delivery efficiency of fusion proteins of the present invention into those cells (B cell lymphoma, Lung Cancer Calu 6, Bronchial Cancer HBE, Skin Cancer MMAN, and Prostate Cancer PC3) was dependent on cell types. Nevertheless, SP1-TAT-GFP-Fc entered a variety of cell types, and this is shown by directly visualizing the green fluorescence of SP1-TAT-GFP-Fc inside the cells in vitro after trypsinization of the cell surface-bound fusion proteins (FIG. 7).

Confocal LASER Scanning Microscopy:

To investigate subcellular localization in HELA cells following transduction of fusion proteins and trypsinization of the cell surface, internalized SP1-TAT-GFP-Fc was detected by green fluorescence and visualized under confoal LASER scanning microscopy. As shown in FIG. 8, SP1-TAT-GFP-Fc was internalized in microsomal aggregates.

Variants of Transduction Domains:

A transduction domain of the present invention (as described in Example 1) is composed of a secretion signal sequence and secretion inhibition sequence. In this example, we show that neither a secretion signal peptide nor HIV-1 TAT sequence alone is as efficient, whether attached at the N- or C-terminus of GFP-Fc fusion protein. These domains failed to deliver enough fusion protein for visualization under fluorescence microscope. However, a combination of the secretion signal sequence and HIV-1 TAT not only allowed us to produce a full length fusion protein with an intact secretion signal peptide (as demonstrated in example 1) but also forms a highly potent transduction domain capable of delivering large proteins into cells.

Figure 9A:
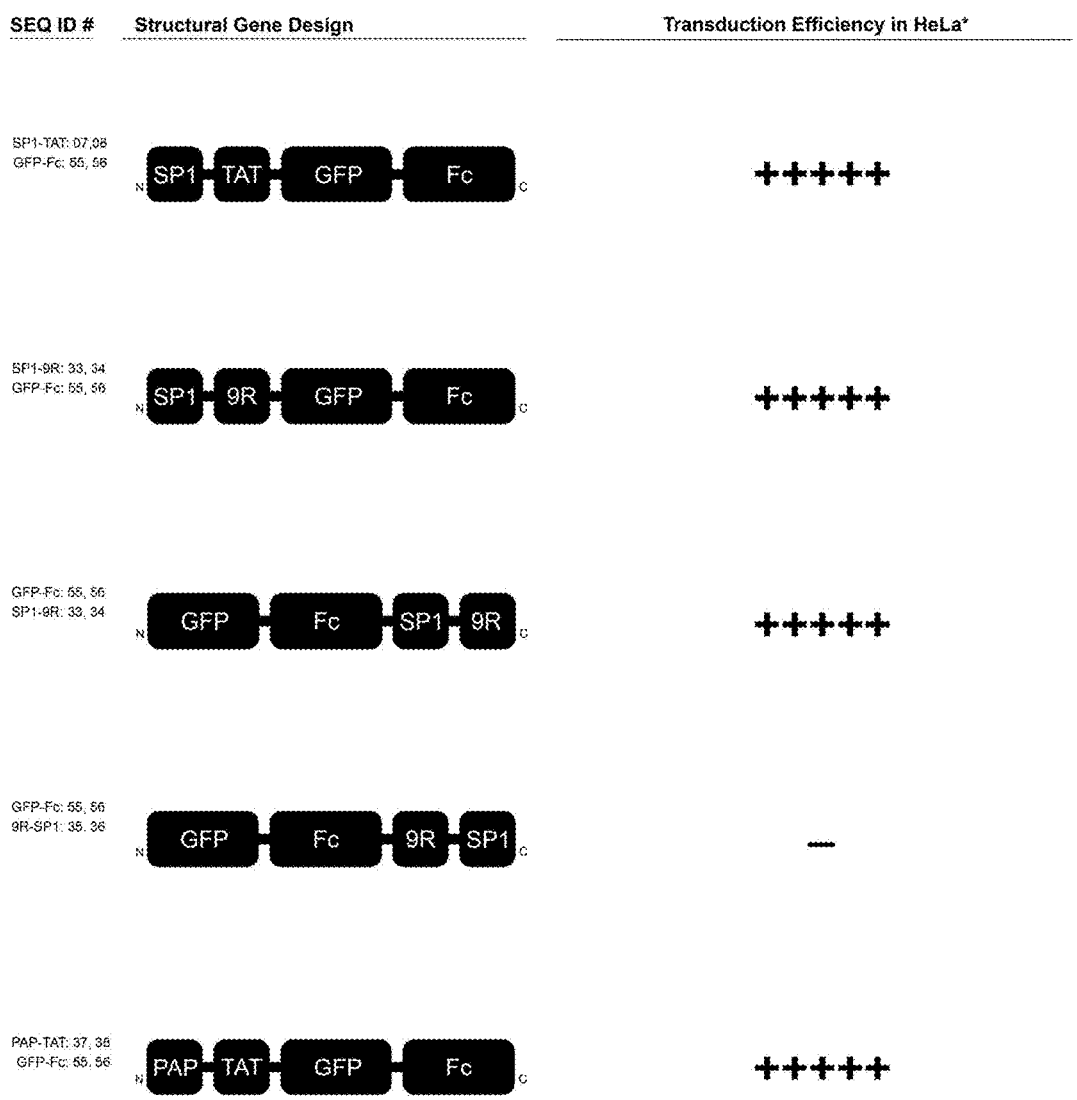
FIGS. 9A and B contain charts showing design of variants of iPTD-GFP-Fc. These fusion proteins were expressed and purified for comparing intracellular transduction efficiency. Relative transduction efficiency was estimated by directly visualizing the amount of intracellular green fluorescence in HELA recipient cells, under fluorescence microscopy.
Figure 10:
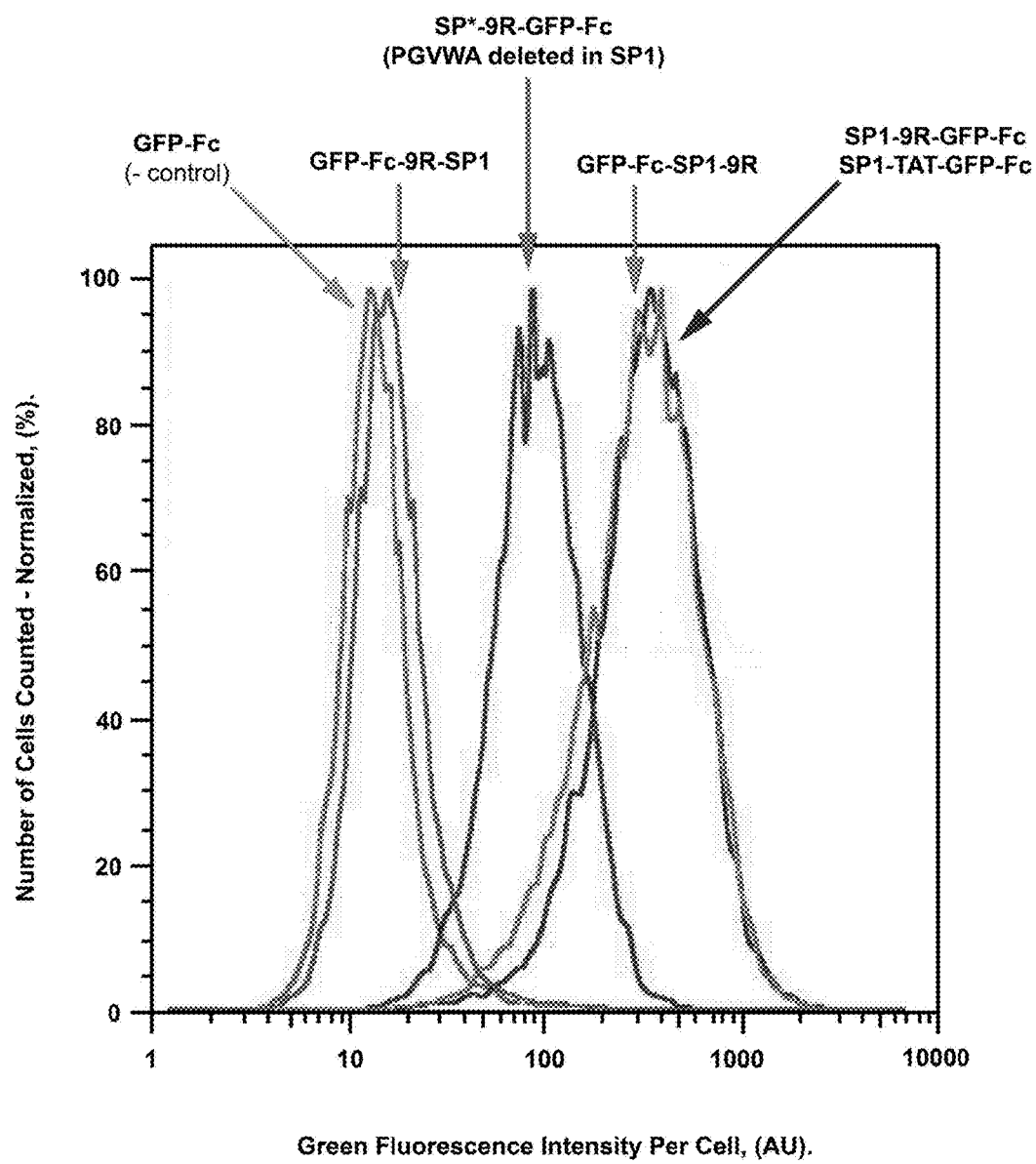
FIG. 10 is a graph showing transduction efficiencies of variants shown in FIGS. 9A and B in HELA cells, analyzed by FACS.

In order to understand the mechanism behind this surprising improvement, and realize its advantages of this finding, variants of transduction domain sequences were made to reveal design considerations. The variants of transduction domains of the present invention shown in FIGS. 9A and 9B were fused to GFP-Fc, and produced/purified as recombinant fusion proteins for comparing intracellular delivery efficiency associated with these sequences in protein transduction domain (FIG. 10). Replacing SP1 with another secretion signal peptide sequence (PAP) in the fusion construct PAP-TAT-GFP-Fc (SEQ ID#37) resulted in strong transduction efficiency like SP1-TAT-GFP-Fc or SP1-9R-GFP-Fc. The transduction domain can also be engineered to the C-terminus of GFP-Fc, and the resulting protein has the same intracellular delivery efficiency as the SP1-TAT-GFP-Fc. However, when the arrangement of secretion signal sequence and cleavage inhibition sequence is reversed as in GFP-Fc-9R-SP1, efficiency of cellular entry decreased to a level comparable to that of the signal peptide sequence alone as transduction domains. In addition, when the secretion signal peptide sequence component is truncated by deletion of the signal peptide cleavage site (as in the fusion constructs SP*-9R-GFP-Fc, PGVWA-GFP-Fc, and SP3R-GFP-Fc), intracellular delivery efficiency decreased, indicating that a full length or a functional secretion signal peptide sequence is preferential.

Experimental Procedures

Cloning, Expression, and Purification of TAT-GFP-Fc:

Because of the uncleaved signal sequence, which remains attached in the purified SP1-TAT-GFP-Fc, a positive control for the protein transduction tests containing the TAT sequence at the N-terminus of GFP-Fc, was constructed. A TAT-GFP gene fragment was PCR amplified from the structural gene sequence of SP1-TAT-GFP-Fc using the following DNA oligonucleotides as primers. The forward primer (SEQ ID#93): CTCTGCGGCCGCCACC ATGAGGAAGAAGAGGAGGCAG, and a reverse primer (SEQ ID#94): CTCTGAATTCCTTGTACAGCTCGTC-CATGCC. These primers were designed to include an Not I restriction site followed by a Kozak sequence and a translation start codon in the 5' end, while the 3' end of the gene is engineered to include an Eco RI restriction site for subcloning.

The purified TAT-GFP PCR product was digested with Not I and Eco RI, and then ligated with Fc fragment prepared by Eco RI and Xho I. The final full length TAT-GFP-Fc was cloned into expression vector pcDNA3.1(+). The DNA sequence was confirmed by both restriction mapping and sequencing analysis.

Single cells of HEK293 expressing high level of TAT-GFP-Fc (evident from the intense green fluorescence upon UV radiation) were selectively isolated and propagated for growth. Western Blot analysis of the whole cell lysate with anti-GFP antibodies confirmed the expression and intracellular localization for the expressed TAT-GFP-Fc. Adherent HEK293 cells expressing TAT-GFP-Fc were grown, and at 100% confluency the HEK293 cells were harvested for purification of TAT-GFP-Fc fusion protein. Subcellular fractionation of the TAT-GFP-Fc revealed that the expressed TAT-GFP-Fc is a soluble protein. However, TAT-GFP-Fc became precipitated on Protein A column chromatography during acid elution (100 mM citrate buffer, pH 3.0).

Purification of SP1-TAT-GFP-Fc was modified by the incorporation of a detergent as in Example 1, which significantly improved solubility of TAT-GFP-Fc and compatibility with the Fc-affinity chromatographic purification method. Approximately 5 grams of wet HEK293 cell pellet was re-suspended in 20 mL (final volume) of Cell Lysis Buffer [150 mM NaCl, 20 mM K/Na/HP042-(pH 8.0), 2 mM EDTA (pH 8.0)]. Prior to lysis, the sonicator probe was cooled with ice/cold water and used to lyse the cells (Branson Sonifier 250; sonication parameter: 50% duty cycle per pulse, 30-seconds sonication pulse for 10 times, cool the sonicator probe on ice between pulses). Insoluble material was spun down in a 50 ml-size conical tube, (1000 rpm/10 minutes/10° C.). After low speed centrifugation, a pipette was used to transfer the cloudy supernatant to a 25-mL size Ultracentrifuge tube, balanced to 2 decimal places, and spun at 100,000×g (70Ti rotor, use 45,000 rpm/60 minutes/10° C.; Beckman Optima XL100k). The clarified supernatant as added to extraction buffer 0.5% (w/v) Zwittergent 3-12, 500 mM NaCl, 50 mM Glycine (pH 10.0) (total volume will be 200 mL), followed immediately by 20 mL of phosphate neutralization solution [500 mM of NaH2PO4, 750 mM of NaH2PO4/K2HPO4 (pH 8.0)](1/10th of the Extraction Volume). After mixing and loading onto a Protein-A column (1CV=550 microliter), a low-pressure peristaltic pump (e.g., Pharmacia P-1, Multiplier at 10, Speed setting points at or between 3-4) was used to deliver the sample onto the column. After all the sample had passed through, 20 mL of Wash Buffer No. 1 (0.5% (w/v) Zwittergent 3-12, 500 mM NaCl, 20 mM TrisHCl (pH 7.5)) was passed, followed by a rinse of the protein-bound column with 20 mL of Wash Buffer No. 2 [0.5% (w/v) CHAPS, 150 mM NaCl, 20 mM TrisHCl (pH 7.5)].

Five 1.5 mL size Eppendorf tubes were prepared, each with 400 microliters of Neutralization buffer [0.5% (w/v) CHAPS, 150 mM NaCl, 1M TrisHCl (pH 9.0)]. 1 mL of Elution buffer [0.5% (w/v) CHAPS, 150 mM NaCl, 100 mM Citrate (pH 3.0)] was applied onto the resin surface. After 1 mL has passed through, they were mixed to ensure good neutralization followed by the second fraction, and application of another 1 mL of Elution buffer. This process was repeated until five fractions were collected. Usually, all the protein was in the first fraction (1.4 mL total). Using a 4-mL size 30 kD MWCO Millipore Centricon, the first fraction (1.4 mL) topped-up with Exchange Buffer [0.5% (w/v) CHAPS in PBS—Phosphate Buffer Saline (pH 8.0)] (to a total volume of around 5 mL) was spun at 3500 rpm/5 minutes/8° C. After 5 minutes, the content of the concentrator was mixed to prevent high concentrations localized at the bottom of the concentrator. This was repeated until only ~250 microliters in the concentrator. The concentrator was then topped-up with Exchange Buffer [0.5% (w/v) CHAPS in PBS buffer (pH 8.0)] and spun at 3500 rpm/5 minutes/8° C. for 5 minutes, followed by mixing and repeating until only ~150 microliters was left in the concentrator. TAT-GFP-Fc was purified to at least 95% purity as judged based on SDS-PAGE stained with Coomassie Blue.

Confirmation and Identification of the Purified Fusion Proteins:

The identity of the purified fusion protein, TAT-GFP-Fc, was confirmed by Western Blot analysis with anti-GFP antibody as shown in FIG. 5. The purity of the purified fusion proteins was analyzed on SDS-PAGE and stained with Coomassie Blue (FIG. 4). In addition, the protein sequence of TAT-GFP-Fc was confirmed at IOWA State University—Protein Facility.

Imaging of the Intracellular SP1-TAT-GFP-Fc with Fluorescence Microscopy:

Intracellular delivery of the GFP-Fc fusion protein was tested for each individual transduction domain (including the GFP-Fc, SP1-TAT-GFP-Fc, GFP-Fc-TAT, and TAT-GFP-Fc). The target recipient cell host was HELA, and success of transduction was directly visualized/analyzed by fluorescence microscopy equipped with a UV radiation module.

Adherent HELA cells grown to approximately 80% confluency in the 24-well plates (Greiner Brand) is used for protein transduction test. 250 ul of SP1-TAT-GFP-Fc, TAT-GFP-Fc, and GFP-Fc were individually prepared in pre-warmed DMEM (37° C.) (Fisher Brand) with 10% Fetal Calf Serum (VWR Brand) at a final concentration of 10 or 20 ug/ml. The growth media for the HELA cells was replaced with 250 ul of fresh media containing the fusion protein proteins at 10 or 20 ug/ml. The cells were incubated for 1 hour at 37° C. (5% carbon dioxide) and the growth media removed. The HELA cells were gently rinsed with 500 ul of PBS (prewarmed to 37° C.). The PBS wash (prewarmed to 37° C.) was repeated two more times to ensure that unbound fusion protein was removed from the extracellular environment. Photos were taken using Nikon D5000 camera and Nikon TE200 microscope using a UV lamp.

A significant difference in brightness and contrast was readily visible to the eye, showing that SP1-TAT-GFP-Fc produced a much stronger intracellular fluorescence than either the TAT-GFP-Fc or GFP-Fc-TAT (as represented in FIG. 5).

Effect of Detergents on Transduction Ability of iPTD on HELA:

The effect of different detergents used during the development of the purification protocols were tested on transduction efficiency. The protein transduction test was performed in the same manner as described above, and a detergent was included in all cellular transductions of fusion proteins including the negative control with GFP-Fc. We found that the amphiphiles employed did not influence the cellular transduction of cargo fusion protein and absence of cytotoxicity was confirmed with the CytoScan LDH Cytotoxicity Assay kit from G Biosciences.

Transduction of Fusion Proteins to Different Cell Types:

The protein transduction test was carried out on different recipient cells (including Calu6, HBE, Hela, MMAN, PC3, and Neuro2A), in the same manner as described above. The results were visualized with fluorescence microscopy equipped with a UV radiation module. The intracellular fluorescence as a result of fusion protein transduction is represented in FIG. 7.

FACS Analysis on Transduction Efficiency of Fusion Proteins:

Efficiency of SP1-TAT-GFP-Fc in transduction was compared to those of TAT-GFP-Fc and GFP-Fc-TAT using FACS. Adherent HELA cells were sub-cultured in 24-well plates, and grown to 80% confluence for protein transduction assay. To start the transduction experiment, the adherent cells were washed with fresh culture media, and then incubated with culture media containing the PTD-GFP-Fc fusion protein. The assay for comparing transduction efficiency utilized bug of PTD-GFP-Fc fusion proteins mixed in 1 ml of freshly prepared culture media containing DMEM, 10% FCS, Penicillin/Streptomycin, glutamine, and 0.5% (w/v) CHAPS. The transduction assay was carried out in a 37° C. incubator, supplemented with 5% carbon dioxide, for 2 to 4 hours. After transduction, the adherent cells were washed with fresh PBS solution to remove unbound PTD-GFP-Fc. The adherent cells were treated with 0.25% (w/v) Tyrpsin (in 0.25 mM EDTA) to digest away any loosely bound or cell surface-attached PTD-GFP-Fc fusion proteins (at 37° C.). After trypsinization of the cell surface, the cells were washed (e.g., centrifuged and resuspended in fresh PBS containing the 10% FCS solution) for FACS analysis. Efficiency of intracellular protein transduction into HELA cells was quantified by measuring the amount of green fluorescence inside the cell.

Cloning of PTM1, 2, 3, 4, 5, 6, 7:

The protein transduction domains PTM1-7 (shown in FIG. 6A), were designed to be fused at the N-terminus of GFP-Fc. The PTM-GFP-Fc fusion proteins were engineered to be expressed and secreted using the mammalian expression system.

For PTM1-7, the nucleotide sequence encoding the protein transduction domains were synthesized as double stranded DNA fragment, which were annealed from forward (sense) and reverse (antisense) DNA oligonucleotide primers, (listed in FIG. 4). The short DNA fragments were processed by restriction digestion at the Nar1 and Sac1 sites, engineered at the 5' and 3' ends, respectively. The GFP-Fc structural gene fragment (SEQ ID#57) was prepared by restriction digestion at the Sac1 and Xho1 restriction sites, which was engineered at the 5' and 3' ends of GFP-Fc DNA sequence, respectively, and cloned in pBlueScript II KS+ vector. The DNA fragment encoding the protein transduction domain (PTM) and the GFP-Fc structural gene were ligated at the Sac1 restriction site, forming the PTM-GFP-Fc ligation product with the open sticky ends (Nar1 and Xho1 at 5' and 3' ends) ready for ligation. The CD33 secretion signal sequence was synthesized as a double stranded DNA fragment which was annealed from forward (SEQ ID#77) and reverse (SEQ ID#78) DNA oligonucleotide primers, listed in FIG. 4. The DNA fragment encoding the CD33 secretion signal peptide was digested with Kpn1 and Xho1 at the 5' and 3' ends, respectively, and ligated to the Kpn1 and Xho1 cloning site in the pBlueScript II KS plasmid. The CD33 secretion signal peptide sequence also contained a Nar1 restriction site near the 3' end, just upstream of the Xho1 site, for ligation with PTM-GFP-Fc. Following double digestion with Nar1 and Xho1, the PTM-GFP-Fc was ligated to CD33 secretion signal peptide sequence in pBlueScript II KS vector, forming the CD33SP-PTM-GFP-Fc fusion protein structural gene. The DNA sequence was verified by restriction mapping, followed by DNA sequencing. The structural gene fragment of CD33SP-PTM-GFP-Fc was prepared (and digested out from the pBlueScript II KS vector) and ligated to the Kpn1 and Xho1 cloning site in the protein expression vector, pCEP4.

Cloning of GFP-Fc-SP and GFP-Fc-PS:

The double-stranded Fc*-SP1 (SEQ ID#59) and Fc*-1PS (SEQ ID#60) sequences were synthesized and cloned in the vector pMA from MrGene™, so that Fc* was immediately followed by the secretion signal peptide sequence (SP1 from human placental alkaline phosphatase, SEQ ID#23), and the corresponding sequence in reverse orientation (1PS, SEQ ID#25). The synthesized Fc* sequence was designed by subcloning the C-terminal Fc gene fragment from the Xma1 restriction site that is located within the full length Fc sequence. A restriction site (Xho1) was presented immediately after three translational stop codons in the 3' end of the structural gene sequences of SP1-GFP-Fc-SP1 and SP1-GFP-Fc-1PS for the expression and purification of protein products, GFP-Fc-SP1 and GFP-Fc-1PS, respectively. The synthesized Fc*-SP1 and Fc*-1PS DNA fragment was released from pMA vector by restriction enzyme Xma1 and Xho1. The Fc*-SP1 and Fc*-1PS fragment than replaced the corresponding Xma1-Xho1 fragment in the construct SP1-GFP-Fc. The resultant gene sequences of SP1-GFP-Fc-SP1 and SP1-GFP-Fc-1PS were cloned into the protein expression vector pCMV-Neo. The sequence was confirmed by restriction mapping followed by DNA sequencing.

Expression of PTM1, 2, 3, 4, 5, 6, 7, and GFP-Fc-PS and GFP-Fc-SP:

The recombinant expression plasmids pCMV-Neo/SP1-GFP-Fc-SP1 and pCMV-Neo/SP1-GFP-Fc-1PS were prepared by using Qiaprep spin mini-columns. The plasmid concentration was 0.5-0.9 ug/ul, UV260/280 ratio>1.80. HEK293 cells were routinely cultured in DMEM containing 10% Heat-inactivated FBS, 2 mM Glutamine, penicillin/streptomycin. Twenty-four hours before transfection, HEK293 cells were sub-cultured into a 6-well plate in antibiotics-free DMEM complete media. When transfection was conducted, the cell confluence was about 70-80%. 2 ug of pure plasmid DNA combined with 6 ul of Roche Fugen HD was transfected into each well. 16 hours after transfection, the transfected cells were sub-cultured in diluted concentration×200, ×400, ×800 and grew in complete DMEM containing 1 mg/mlG418. In the presence of G418 selection marker, the stable clones with strong green color under fluorescene microscope were picked up after 2 weeks.

The constructed plasmids, which were confirmed by restriction mapping and DNA sequencing, were transfected into HEK293 cells for selection (Roche FuGene Transfection Kit). Cells were grown at 37° C. incubator supplemented with 5% carbon dioxide (v/v). Single cell expressing high levels of fusion protein, characterized by the appearance of intense green fluorescence upon UV radiation, were selectively isolated for growth propagation in DMEM media supplemented with fetal bovine serum, glutamine, and penicillin and streptomycin. GFP-Fc-SP1 and GFP-Fc-1PS were constitutively expressed. The adherent HEK293 host cells expressing the fusion proteins were grown in DMEM media supplemented with fetal bovine serum, glutamine, and penicillin and streptomycin. The adherent HEK293 cells at 80% confluence level were washed with prewarmed (37° C.) phosphate buffer saline (Fisher), and replaced with fresh C-SFM-II cell/serum free media (Invitrogen), to which the expressed and processed GFP fusion proteins accumulate.

Western blot analysis of the HEK293 expression cell host and the serum free media using anti-GFP IgG antibody indicated that both GFP-Fc-SP1 and GFP-Fc-1PS were intracellular (not secreted).

Similarly, recombinant expression plasmids, pCEP4/CD33SP-PTM(1-7)-GFP-Fc, were prepared by using Qiaprep spin mini-columns, and transfected into HEK293F cells for selection. Single cells expressing high levels of fusion protein, characterized by the appearance of intense green fluorescence upon UV radiation, were selectively isolated, cryo-protected with 15% (v/v) DMSO, and stored frozen in liquid nitrogen.

For large scale production of PTM(1-7)-GFP-Fc fusion proteins in HEK293F, the cryo-preserved monoclonal cell line was quickly thawed, and gently diluted in a Thawing Medium, which contains 50% (v/v) Conditioned Medium, 25% (v/v) CD-293 Complete Medium from Invitrogen, and 25% (v/v) ExCell-293 Complete Medium from Sigma. The cryo-protectant (DMSO) was removed by washing (e.g., centrifuging and resuspending) the cell pellet in fresh thawing medium. The cells were cultured in thawing medium in a stationary T-25 culture container at 37° C. for 2-3 days until viable cell density (VCD) reached $5 \times 10^5$ cells/ml, before scale-up. Fresh CD-293 Selective Medium, which is CD-293 Complete Medium plus 25 ug/ml Hygromycin, was then added at 3:2 (v/v) ratio to the thawing medium containing cell culture, and culturing continued until high cell density. The high density cells were transferred to shaking flasks, and 25% (v/v) of CD-293 Complete Medium without any Hygromycin added. The flask was shaken on rotary platform shaker (~100 rpm) inside the incubator, for protein expression. Once the cell culture density reached $1 \times 10^6$ cells/ml, the cultures were split in half-one half for harvesting the expressed protein, and the other half as a seed for continuing the subculture.

The serum free media containing the secreted proteins and the expression cell hosts were separately stored for identification and purification of the PTM-GFP-Fc fusion proteins.

Purification of PTM1, 2, 3, 4, 5, 6, 7:

Serum free media containing the expressed PTM-GFP-Fc fusion proteins was harvested, and centrifuged to produce a clarified aqueous supernatant. The clear supernatant was filtered through 0.22 micron membrane to remove small size debris before loading onto the Protein A chromatography resins (Genscript). Fusion proteins carrying the Fc domain were specifically adsorbed to Protein A chromatography resin, and purified from the cell culture media. The fusion proteins, eluted with 100 mM citrate (pH 3.0), were immediately neutralized with Tris buffer. The purified protein fractions were subsequently buffer exchanged to PBS (pH 8.0), and concentrated in a 30 kD molecular weight cut-off Centricon (Millipore). High purity PTM-GFP-Fc was obtained using this method. The protein purity was at least 95% as judged from SDS-PAGE with Coomassie Blue staining.

Purification of GFP-Fc-SP1 and GFP-Fc-1PS:

The purification methods of GFP-Fc-SP1 and GFP-Fc-1PS were identical to that of SP1-TAT-GFP-Fc described in Example 1. GFP-Fc-SP1 and GFP-Fc-1PS were purified to at least 95% purity as judged based on SDS-PAGE stained with Coomassie Blue.

Cloning of iPTD Variants:

For SP1-9R (SEQ ID#33 and 34), the SP1-9R-GFP-Fc structural gene was constructed by subcloning and ligating the DNA fragment containing the SP1-9R (SEQ ID#34) released (restriction digest) from pUC57 vector, and the GFP-Fc gene fragment (SEQ ID#56) released from pBlueScript II KS vector. The SP1-9R gene (SEQ ID #34) in pUC57 was made using gene synthesis at GenScript, and was engineered to have Not1 and Sac1 restriction site at the 5' and 3' ends, respectively. The GFP-Fc gene fragment (SEQ ID#56) was engineered to have the Sac1 and Xho1 at the 5' and 3' end, respectively. Following restriction digestion and ligation, the structural gene of SP1-9R-GFP-Fc was inserted into the Not1 and Xho1 cloning sites in pCDNA3.1 (+) vector, and subsequently transferred (restriction and ligation at Not1 and Xho1 sites) to an expression vector. The structural gene sequence was verified by restriction mapping and DNA sequencing.

The GFP-Fc-SP1-9R structural gene was constructed by subcloning and replacing (restriction and ligation) the corresponding Fc* fragment in the GFP-Fc structural gene with the DNA fragment containing the Fc*-SP1-9R sequence (SEQ ID#65) released (restriction digest) from pUC57 vector. The synthesized Fc* sequence was designed by subcloning the Fc C-terminal fragment from the Xma1 restriction site that is located within the full length Fc sequence. The Fc*-SP1-9R gene (SEQ ID#65) in pUC57 was synthesized at GenScript, and was engineered to have the Xma1 and Xho1 at the 5' and the 3' ends, respectively. The Fc*-SP1-9R fragment then replaced the corresponding fragment in the GFP-Fc structural gene, which was released (subcloned and digested with Hind111 and Xma1) from pBlueScript II KS vector, to obtain the GFP-Fc-SP1-9R structural gene fragment. The GFP-Fc-SP1-9R was cloned into the Hind111 and Xho1 cloning site in pCDNA 3.1(+), and then subcloned in pCMV vector for protein expression.

The GFP-Fc-9R-SP1 structural gene was constructed using a similar approach. The Fc*-9R-SP1 sequence (SEQ ID #66) was synthesized in pUC57 by GenScript, and was engineered to be released by Xma1 and Xho1 restriction enzymes at 5' and 3' ends, respectively. Through subcloning, the corresponding fragment in GFP-Fc structural gene was replaced (restriction digested and ligated) with Fc*-9R-SP1 (SEQ ID#66) at the Xma1 and Xho1 sites to produce the GFP-Fc-9R-SP1 structural gene. The GFP-Fc-9R-SP1 gene fragment was inserted (restriction digested and ligated) into the pCDNA 3.1(+), and then subcloned in pCMV vector for protein expression.

For PAP-TAT (SEQ ID#37 and 38) the PAP-TAT-GFP-Fc structural gene was constructed by subcloning the DNA fragment containing the PAP-TAT sequence (SEQ ID#96) and the GFP-Fc gene fragment (SEQ ID#56). The PAP-TAT DNA fragment in pUC57, synthesized at GenScript, was engineered to have the Not1 and Sac1 restriction sites at the 5' and 3' ends, respectively. The GFP-Fc gene fragment was prepared from restriction digestion of the SP1-9R-GFP-Fc structural gene (in pBlueScript II K5 plasmid) with Sac1 and Xho1 at the 5' and 3' ends, respectively. The PAT-TAT and GFP-Fc fragments were ligated to form the PAP-TAT-GFP-Fc structural gene in pBlueScript II KS plasmid. Following restriction mapping and DNA sequencing, the PAP-TAT-GFP-Fc structural gene was inserted (restriction digestion and ligation) into the Not1 and Xho1 cloning sites in an expression vector for protein expression. The PAP-Pro4G (SEQ ID#39 and 40) sequence in the PAP-Pro4G-GFP-Fc structural gene was produced by PCR, using the PAP-TAT-GFP-Fc structural gene (in pBlueScript II KS plasmid) as a PCR template and the following DNA oligonucleotide sequences as PCR primers. The PAP secretion signal peptide sequence fragment was engineered to have the BamH1 and Xma1 restriction sites at the 5' and 3' ends, respectively, and was produced by using the forward primer (SEQ ID#97) 5'→3': CTCTGGATCCACCCATGGCGATG, and the reverse primer (SEQ ID#98) 5'→3': CTCT CCCGGGGGCCAGGCTCAGCTGGAG. In addition to BamH1 site, the forward primer (SEQ ID#97) for the PAP secretion signal peptide sequence also had a Nco1 restriction site downstream of BamH1, which was engineered for the convenience of downstream subcloning and restriction digestion mapping. The TAT-GFP sequence fragment was engineered to have the Xma1 and EcoR1 restriction sites at the 5' and 3' ends, respectively, and was produced by using the forward primer (SEQ ID#99) 5'→3': CTCT CCCGGGGGAGGTGGCAGCAAGGGCGAGGAGCTGT TC, and the reverse primer (SEQ ID#100) 5'→3'; CTCTG- CACGGTGGGCATGTGTGAGT. The PCR products of PAP and TAT-GFP were digested with respective restriction enzymes, and ligated to form the PAP-TAT-GFP structural gene sequence in the BamH1 and EcoR1 cloning sites in a vector plasmid.

The gene sequence of PAP-TAT-GFP was confirmed by restriction mapping and DNA sequencing. The Fc gene sequence fragment (SEQ ID#52) was prepared (restriction digestion with the EcoR1 and Xho1) from the GFP-Fc structural gene (SEQ ID#56) in pBlueScript II KS plasmid. The PAP-TAT-GFP and the Fc gene sequence fragments were ligated into the Not1 and Xho1 cloning site in pCDNA 3.1(+) vector for expression of the PAP-TAT-GFP-Fc.

The SP1-3P (SEQ ID #41 and 42) sequence in the SP1-3P-GFP-Fc structural gene was produced by PCR, using the synthesized SP1-9R gene (SEQ ID#34) (in pUC57 plasmid by GenScript) as a PCR template and the following DNA oligonucleotide sequence as PCR primers. Forward primer (SEQ ID#101) 5'→3': TCAGGATGAGGTCCT- GTCAG, and the reverse primer (SEQ ID#102) 5'→3': CTCTGAGCTCAGGTGGCGGGGCCCAGACGCCAGG CAG. The SP1-3P PCR fragment was engineered to have the Sac1 site at the 3' end, and Hind111 and Not1 sites downstream of the 5' end for cloning. Following PCR and restriction digestion with Not1 and Sac1, the SP1-3P DNA fragment was ligated with the GFP-Fc structural gene fragment (SEQ ID#56), which was prepared from the restriction digestion (Sac1 and Xho1) of GFP-Fc in pBlueScript II KS plasmid. The SP1-3P-GFP-Fc structural gene fragment was then ligated to the Not1 and Xho1 cloning sites in pCDNA 3.1(+) for expression of the SP1-3P-GFP-Fc. The SP*-9R- GFP-Fc structural gene was made in the same way. The SP*-9R (SEQ ID#43 and 44) sequence in SP*-9R-GFP-Fc structural gene was produced by PCR, using the synthesized SP1-9R gene (SEQ ID#34) (in pUC57 plasmid by Gen- Script) as a PCR template and the following DNA oligonucleotide sequence as PCR primers: forward primer (SEQ ID#103) 5'→3'; TCAGGATGAGGTCCTGTCAG, and reverse primer (SEQ ID#104) 5'→3': CTCTGAGCTCTCT- GCGCCTTCTCCTGCGCCTTCTCCTCAGCCTCAGGC- CCAGCAG. The 5P*-9R PCR fragment was engineered to have the Sac1 site at the 3' end, and Hind111 and Not1 sites downstream of the 5' end for cloning. Following PCR and restriction digestion with Not1 and Sac!, the SP*-9R DNA fragment was ligated with the GFP-Fc structural gene fragment (SEQ ID#56), which was prepared from restriction digestion (Sac1 and Xho1) of GFP-Fc in pBlueScript II KS plasmid. The SP*-9R-GFP-Fc structural gene fragment was then ligated to the Not1 and Xho1 cloning sites in pCDNA 3.1(+) for expression of the SP*-9R-GFP-Fc. For PGVWA- 9R-GFP-Fc structural gene preparation, the sequence for PGVWA-9R (SEQ ID#45 and 46) was embedded in the PCR forward primer (SEQ ID#105) 5'→3': CTCT GCGGCCGC CACC ATG CCT GGC GTC TGG GCC AGG. The reverse PCR primer was SEQ ID#106; 5'→3': CTCT GAATTC CTT GTA CAG CTC GTC CAT GC. The PCR template used in DNA amplification was the structural gene of SP1-9R-GFP- Fc in pBlueScript II KS. The PCR amplification product, PGVWA-9R-GFP, was digested with Not1 and EcoR1 restriction enzymes for ligation with the Fc structural gene fragment (SEQ ID#52), which was prepared from restriction digestion (EcoR1 and Xho1) of GFP-Fc in pBlueScript II KS plasmid. The PGVWA-9R-GFP-Fc structural gene fragment was then ligated to the Not1 and Xho1 cloning sites in pCDNA 3.1(+) for expression of the PGVWA-9R-GFP-Fc.

For SP3R (SEQ ID#47 and 48) the SP3R-GFP-Fc structural gene was assembled from ligation of the following DNA fragments. First, the DNA sequence of the secretion signal peptide sequence of human placental alkaline phosphatase that is embedded in the SP1-GFP-Fc structural gene in pCDNA3.1 (+) was released by restriction digestion with Mlu1 and Xma1. Secondly, the 3R-GFP gene fragment was produced using a PCR method with the SP1-TAT-GFP-Fc structural gene in pCDNA 3.1(+) as a template and the following DNA oligonucleotide sequences as primers. PCR forward primer (SEQ ID#107) 5'→3': CTCT CCCGGGAGGAGGAGGGAGCTCAGCAAGGGCGAG.

The reverse PCR primer (SEQ ID#108) 5'→3': CTCT GAATTCCTTGTACAGCTCGTCCATGCC. The PCR amplification product, 3R-GFP, was digested with Xma1 and EcoR1 restriction enzymes for ligation. Thirdly, the Fc structural gene fragment (SEQ ID#52) was prepared from restriction digestion (EcoR1 and Xho1) of GFP-Fc in pBlue-Script II KS plasmid. The three DNA fragments were ligated into the Mlu1 and Xho1 restriction sites in pCDNA 3.1 (+) for expression of the SP3R-GFP-Fc.

Expression of Fusion Protein Variants:

The constructed plasmids, which were confirmed by restriction mapping and DNA sequencing, were transfected into HEK293 cells for selection (Roche FuGene Transfection Kit). Cells were grown at 37° C. incubator supplemented with 5% carbon dioxide (v/v). Single cells expressing high levels of fusion protein, characterized by the appearance of intense green fluorescence upon UV radiation, were selectively isolated for growth propagation in nutrient rich tissue culture DMEM supplemented with fetal bovine serum, glutamine, and penicillin and streptomycin.

The following variants: GFP-Fc-SP1-9R, GFP-Fc-9R-SP1, PAP-Pro4G-GFP-Fc, SP1-3P-GFP-Fc, SP*-9R-GFP-Fc, PGVWA-9R-GFP-Fc, and SP3R-GFP-Fc in pCDNA 3.1 (+) were constitutively expressed, while the SP1-9R-GFP-Fc and PAP-TAT-GFP-Fc structural genes in the expression vector were expressed by induction with 120 micromolar of metal ion (zinc sulfate). The adherent HEK293 host cells expressing the fusion proteins were grown on tissue culture dishes in DMEM media supplemented with fetal bovine serum, glutamine, and penicillin and streptomycin. The adherent HEK293 cells at 80% confluence level were washed with prewarmed (37° C.) phosphate buffer saline (Fisher), and replaced with fresh C-SFM-II cell/serum free media (Invitrogen), to which the expressed and processed GFP fusion proteins accumulate. Western blot analysis of the HEK293 expression cell host and the serum free media using anti-GFP IgG antibody indicated that all of GFP-Fc-SP1-9R, GFP-Fc-9R-SP1, PAP-Pro4G-GFP-Fc, SP1-3P-GFP-Fc, SP*-9R-GFP-Fc, PGVWA-9R-GFP-Fc, SP3R-GFP-Fc, SP1-9R-GFP-Fc, and PAP-TAT-GFP-Fc are intracellular and were not secreted into the culture media.

Purification of Fusion Protein Variants:

The purification method for the variants GFP-Fc-SP1-9R, GFP-Fc-9R-SP1, PAP-Pro4G-GFP-Fc, SP1-3P-GFP-Fc, SP*-9R-GFP-Fc, PGVWA-9R-GFP-Fc, SP3R-GFP-Fc, SP1-9R-GFP-Fc, and PAP-TAT-GFP-Fc was identical to that of SP1-TAT-GFP-Fc described in Example 1. After buffer exchange, the purified proteins were suitable for testing in cell culture.

Kinetics of the Fusion Protein Transduction into Cells Using FACS (Comparison of Transduction Efficiency, Time Course, and Dose Dependent):

The efficiency of SP1-TAT-GFP-Fc in intracellular transduction was quantitatively analyzed and compared to those of conventional protein transduction domains using FACS. Adherent HELA cells were sub-cultured in 24-well plates, and grown to 80% confluence for protein transduction assay. To start the transduction experiment, the adherent cells were washed with fresh culture media, and then incubated with culture media containing the PTD-GFP-Fc fusion protein. The assay for comparing the transduction efficiency of different protein transduction domains was as described above.

For analyzing the kinetics of protein transduction into cells (e.g., time course event and rate of intracellular protein delivery), adherent HELA cell grown to 80% confluence level was used. 10-30 ug of PTD-GFP-Fc fusion protein in 1 ml of culture media containing DMEM, 10% FCS, Penicillin/Streptomycin, glutamine, and 0.5% (w/v) CHAPS was incubated with the adherent HELA cells for variable time period (25 mins, 60 mins, 2 hours, and 4 hours). After incubation for defined time interval, the cells were washed and treated with trypsin in PBS at 37° C. to remove the cell surface-bound PTD-GFP-Fc. After trypsinization, the cells were immediately washed and stabilized in PBS containing 10% FCS solution for FACS analysis. The resulting transduction efficiency was graphed as a function of time interval of incubation for transduction.

For analyzing concentration dependency in intracellular protein transduction (e.g., minimum threshold level of protein required for transduction, and saturation level of protein in transduction), adherent HELA cell grown to 80% confluence level were used. Various amounts of PTD-GFP-Fc fusion protein (5 ug, 10 ug, 20 ug, 100 ug, and 500 ug) in 1 ml of culture media containing DMEM, 10% FCS, Penicillin/Streptomycin, glutamine, and 0.5% (w/v) CHAPS was incubated with the adherent HELA cells for 24 hours. After incubation for a defined time period, the cells were washed and treated with trypsin in PBS at 37° C. to remove cell surface-bound PTD-GFP-Fc. After trypsinization, the cells were immediately washed and stabilized in PBS containing 10% FCS solution for FACS analysis. The resulting transduction efficiency was graphed as a function of fusion protein concentration in transduction.

Confocal 3D LASER Scanning Microscopy:

Sub-cellular localization of SP1-TAT-GFP-Fc in HELA cell was verified by confocal laser-scanning microscopy with an Olympus FLUOVIEW FV10i microscope at The University of British Columbia, Bioimaging Facility. For sample preparation, adherent HELA cells were sub-cultured in 24-well plates (embedded with the microscope glass cover slides in the wells), and grown to 80% confluence for protein transduction assay. The adherent cells were washed with fresh culture media, and then incubated with culture media containing the SP1-TAT-GFP-Fc fusion protein. The assay for comparing transduction efficiency of the different protein transduction domains was as described above. After trypsinization of the cell surfaces, the cells were stabilized in fresh culture media at 37° C. for 1-2 hours for reattachment to the embedded microscope glass cover slides before confocal microscopy. Live adherent cells were stained with DAPI (i.e., 4',6-diamidino-2-phenylindole), which binds preferentially to AT rich regions in DNA in nucleus, for identification/labeling of nucleus. The cells were also incubated with dialkylcarbocyanine probes (Biotium DiD labeling solution) for staining the cell membrane and the incorporated intracellular lipid vesicles. Sub-cellular localization of incorporated SP1-TAT-GFP-Fc fusion protein was identified by detection of the GFP green fluorescence in cells. The differentially stained/labeled organelles and GFP fluorescence were simultaneously imaged with respective excitation wavelengths from the same cell, as shown in FIG. 8.

Example 3

The efficiency of intracellular protein transduction with a transduction domain of this invention over conventional transduction domains implies that the mechanism of action of the present invention for intracellular delivery is fundamentally different to the invasive membrane penetration/association modes known for some conventional transduction technologies. Rearrangement of the secretion signal peptide and the cleavage inhibition sequences resulted in a significant decrease in protein delivery function, indicating that recognition of a specific structural arrangement during the transduction process is involved. Here, we present evidence showing that a protease sensitive cell-surface protein or receptor is involved in recognition of a transduction domain of the present invention. This recognition mechanism further provides for the use of other secretion signal peptide sequences in assembling specific domains of this invention targeted to specific cell types and/or subcellular locations within.

Figure 11A:
FIG. 11A is a chart showing the effect of a polyanionic molecule (heparin) on intracellular protein transduction in HELA cells. SP1-TAT-GFP-Fc fusion protein delivery is not affected by heparin. Mere TAT-mediated protein transduction mechanism using GFP-Fc-TAT was inhibited and reversed by heparin.

Membrane-Bound Protein/Receptor Mediates the Intracellular Delivery of iPTD:

It has been reported that transduction of cation-rich HIV1 TAT-fusion proteins can be removed and/or reversed by incubating a cell with the negatively charged molecule heparin (see, e.g., Lundberg et al. (2003) Mol. Ther., 8, 143-150). A cleavage inhibition sequence used in the present invention includes cation-rich cluster. Transduction into cells is not affected by competition with heparin (see FIG. 11A), indicating that an alternative route of entry (different mechanism) into cells is utilized by this invention. Secondly, the mechanism underlying the entry into cells of a protein of this invention is different from the direct membrane association and/or penetration modes established by the polycationic, hydrophobic and amphipathic peptide vector in the prior art (see, e.g., Vives et al. (1997) J. Biol. Chem., 272, 16010-16017; Derossi et al. (1996) J. Biol. Chem., 271, 18188-18193; Chaloin et al. (1998), Biochem. Biophys. Res. Commun., 243, 601-608; Chaloin et al. (1998), Biochim. Biophys. Acta., 1375, 52-60).

Figure 11B:
FIG. 11B is a chart showing that trypsinization of recipient HELA cells rendered the cell surface permeable and fragile. Removal of the cell surface proteins by trypsin inhibited delivery of the iPTD-GFP-Fc fusion protein of this invention into cells.
Figure 12A:
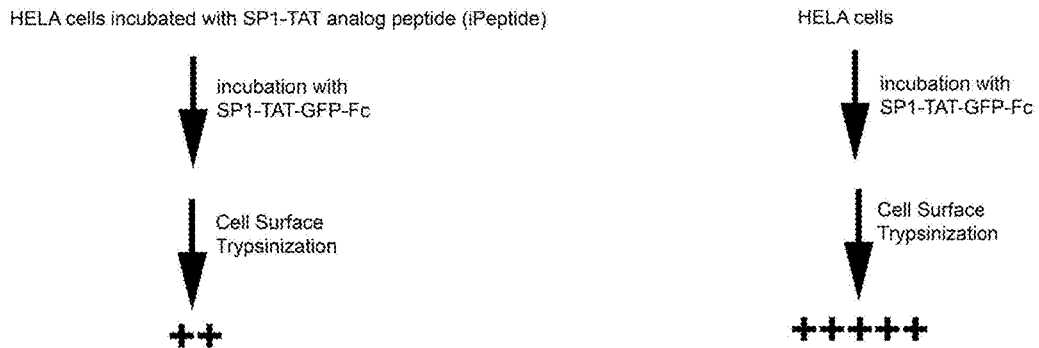
FIG. 12A is a chart showing competitive inhibition of iPTD-GFP-Fc delivery into cells by a peptide analog (termed "iPEPTIDE"). Addition of the peptide analog effectively inhibited intracellular delivery efficiency suggesting competition for a specific protein/receptor on the cell surface.
Figure 12B:
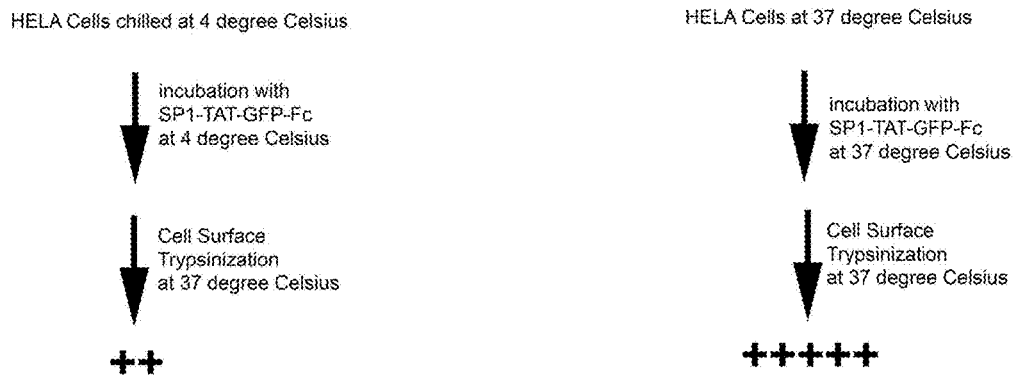
FIG. 12B is a chart showing that delivery of a fusion protein of this invention into cell is an energy dependent process. Lowering the incubation temperature to 4° C. inhibited transduction of the cargo protein.

Trypsinizing a target cell host prior to the addition of SP1-TAT-GFP-Fc resulted in inhibition of protein delivery into the cells. The residual efficiency (as represented in FIG. 11B) may be the result of a surface receptor protein that was regenerated by the living cells during the stabilization process. The marked decrease in transduction efficiency was surprising because the trypsinized cell that is void of the surface proteins and collagen structures has a fragile membrane structure (shown by the detached and round-shaped cells), and should be easily accessible to foreign materials by membrane penetration. Surprisingly, the present invention's mode of delivery was inhibited by cell surface trypsinization, suggesting that a cell surface protein receptor is involved in the transduction mechanism. The dramatically decreased efficiency of SP1-TAT-GFP-Fc entry into the permeabilized cell indicates a specific mechanism mediated by a cell surface-bound proteins/receptors that would have been destroyed by trypsinization. This is also supported by an analog peptide termed "iPeptide" herein in (SEQ ID#109) inhibiting entry of SP1-TAT-GFP-Fc into cells as shown in FIG. 12A. Furthermore, although SP1-TAT-GFP-Fc enters a variety of mammalian cells (as demonstrated in Example 2), other cell hosts (such as insect cells and bacteria) can be resistant to SP1-TAT-GFP-Fc, suggesting that the specific protein/receptor is absent in some organisms. In addition, cell entry is temperature-dependent and is inhibited at low temperature, as shown in FIG. 12B. Efficiency decreased when the incubation temperature was lowered from 37 to 4° C., suggesting that energy is involved in delivery. It is possible that protein delivery was completely inhibited at low temperature and residual transduction activity might have been the result of energy recovery due to subsequent incubation at 37° C. (for trypsinization of the host cell surface for FACS analysis). Although recognition of the fusion protein could be specifically mediated by cell surface proteins/receptors, delivery following the specific recognition is likely through endocytosis. This is evident from the punctuate distribution of SP1-TAT-GFP-Fc, indicative of endosomal vesicles in the cytoplasm (as shown in FIG. 8). The kinetics of fusion protein transduction into recipient cells in Example 2 (FIGS. 9A-9B) is compatible with that of the endocytotic mechanism (see, e.g., Richard et al. (2003), J. Biol. Chem., 278, 585-590).

Receptors that recognize transduction domain sequences of the present invention are likely part of a native molecular machinery involved in the signal sequence recognition and processing in cells. These results lead us to conclude that the secretion signal peptide component of the present invention is a variable parameter, which can be selected or designed according to a desired target cell. The efficiency and specificity of the present technology in intracellular delivery of large proteins can facilitate the development of next generation protein therapeutics targeted to the inside of particular target cells and tissues.

While the signal recognition particle (SRP)-dependent recognition and processing mechanism is highly conserved from prokaryote to mammals, the protein subunits in association with the signal recognition particle and the downstream signal peptide processing mechanisms are uniquely different from species to species. The recognition of a transduction domain of the present invention by a signal recognition particle is not surprising as SRP serves a multitude of function. SRP can correctly identify a wide variety of signal sequences found at the N-terminus of a nascent peptide chain. SRP binding to a signal peptide-bearing protein in a ribosome can cause a pause in translation until the SRP-nascent protein-ribosome complex binds to a specific SRP receptor (SR) on a target membrane. Then, SRP may facilitate complex formation between the ribosome and a translocating transmembrane pore, followed by the release of signal sequence and re-initiation of translation and translocation of the SP-bearing nascent protein chain (see, Stroud RM and Walter P, (1999), Curr. Opin. Struct. Biol., 9, 754). Based on the biological function of a signal peptide sequence, and the functional diversity of SRP in delivering and cycling the signal peptide-bearing proteins between the soluble cytosolic and membrane interface environment, it is evident that receptors that recognize a transduction domain of the present invention are involved in recognition of signal sequence and the native SRP-mediated protein targeting system (see, Stroud RM and Walter P, (1999), Curr. Opin. Struct. Biol., 9, 754).

It is shown herein that presence of a signal peptide with a cleavage inhibition sequence results in signal peptidase enzymes and downstream secretions of the recombinant fusion proteins being inhibited. Therefore, the signal peptidase subunits may also be the receptors that may specifically recognize and bind to the signal peptide component of a transduction domain of the present invention. Without being bound to this theory, presence of the cleavage inhibition sequence may enhance transduction by inhibiting signal peptide cleavage at the target cell, thereby allowing the signal peptide to properly fulfill its role in crossing the target cell membrane. Evidence from this example suggests that a receptor on a cell surface functions specifically for intracellular delivery of a fusion protein of his invention. Without being bound to a particular theory, it may be that secretion machinery and/or related mechanisms on a cell surface recognize the signal peptide and captures a fusion protein containing the intact secretion signal peptide sequence, for reprocessing in the post-translational modification pathway.

Experimental Procedures

Heparin Wash Treatment:

Adherent HELA cells were sub-cultured in 24-well plate, and grown to 80% confluence for protein transduction assay. To start the transduction experiment, the adherent cells are washed with fresh culture media, and then incubated with culture media containing the iPTD-GFP-Fc fusion protein described above. GFP-Fc-TAT and SP1-TAT-GFP-Fc were compared for intracellular transduction efficiency. 10 ug of GFP-Fc-TAT and SP1-TAT-GFP-Fc fusion proteins mixed in inn1 of freshly prepared culture media containing DMEM, 10% FCS, Penicillin/Streptomycin, glutamine, and 0.5% (w/v) CHAPS were incubated with adherent HELA cells in a 372C incubator, supplemented with 5% carbon dioxide, for 4 hours. After transduction, the adherent cells were washed with fresh PBS solution to remove unbound green fluorescent fusion proteins. The adherent cells were washed and incubated with heparin at 372 C to dissociate surface bound or cell surface-attached green fluorescent fusion proteins. After heparin treatment, the cells were washed, centrifuged and resuspended in fresh PBS containing the 10% FCS solution for imaging by fluorescence microscopy.

Temperature-Dependent Transduction:

The efficiency of SP1-TAT-GFP-Fc in intracellular transduction at 4° C. was quantitatively analyzed and compared to that performed at 37° C. Two separate plates of adherent HELA cell cultures grown to 80% confluence provided recipient cell hosts. The adherent cells were washed with fresh culture media. One plate of HELA cell was kept warm at 37° C. incubator, and the other chilled at 4° C. Culture media containing the SP1-TAT-GFP-Fc fusion protein was aliquoted and then adjusted to the desired temperature before adding to the respective cell cultures. Intracellular transduction utilized 10-30 ug of PTD-GFP-Fc fusion proteins mixed in 1 ml of freshly prepared culture media containing DMEM, 10% FCS, Penicillin/Streptomycin, glutamine, and 0.5% (w/v) CHAPS. Transduction was carried out at the set temperature for 2-4 hours. After transduction, adherent cells were washed with fresh PBS solution to remove unbound protein. Adherent cells were trypsinized at 372 C with 0.25% (w/v) Tyrpsin (in 0.25 mM EDTA) to digest away loosely bound or the cell surface-attached fusion proteins. After trypsinization, the cells were washed and stabilized by centrifugation and resuspension in fresh PBS containing the 10% FCS solution for FACS analysis. The efficiency of intracellular protein transduction into HELA cells was quantified by measuring the amount of green fluorescence inside the cell.

iPEPTIDE Inhibitors, and Inhibition of the SP1-TAT-GFP-Fc Intracellular Transduction (FACS Analysis):

"iPEPTIDE" (SEQ ID No: 109) is a truncation analog of SP1-TAT, and was designed to be synthesized by peptide synthesis. Efficiency of SP1-TAT-GFP-Fc in intracellular transduction in the presence of iPEPTIDE at different concentration was quantitatively analyzed and compared using FACS. Adherent HELA cells cultured to 80% confluence were washed in fresh culture media, and then treated with iPEPTIDE at various concentrations in culture media (DMEM, 10% FCS, Penicillin/Streptomycin, glutamine) at 37° C. for 2 hours. Following the iPEPTIDE incubation, the cells were washed extensively with PBS to remove residual iPEPTIDE. The adherent cells were washed with fresh culture media, and then incubated with 20 ug of iPTD-GFP-Fc fusion protein in 1 ml of culture media (DMEM, 10% FCS, Penicillin/Streptomycin, glutamine, and 0.5% (w/v) CHAPS). The transduction assay was carried out at 37° C. incubator (supplemented with 5% carbon dioxide) for 3 hours. After transduction, adherent cells were washed with fresh PBS solution to remove the unbound SP1-TAT-GFP-Fc, and then treated with 0.25% (w/v) Tyrpsin to digest away loosely bound or the cell surface-attached fusion proteins and iPEPTIDE (at 37° C.). After trypsinization, the cells were washed, centrifuged and resuspended in fresh PBS containing the 10% FCS solution for FACS analysis. Efficiency of intracellular protein transduction into HELA cells was quantified by measuring the amount of green fluorescence inside the cell.

Trypsinization of the HELA Cells Prior to iPTD Transduction (FACS Analysis):

Using FACS, efficiency of SP1-TAT-GFP-Fc in intracellular transduction of normal healthy cells was compared to a case in which the recipient cell host was trypsinized prior to protein transduction. Adherent HELA cells grown to 80% confluence were washed in PBS and treated with trypsin (0.25% w/v in 0.25 mM EDTA) for 5 minutes to remove the surface-bound proteins. The cells were then stabilized in fresh culture media (DMEM, 10% FCS, Penicillin/Streptomycin, glutamine) at 37° C. for 1-2 hours for reattachment to a culture plate surface.

Following reattachment of cells, media was removed and replaced with fresh media containing SP1-TAT-GFP-Fc. 10-30 ug of SP1-TAT-GFP-Fc fusion proteins was mixed in 1 ml of freshly prepared culture media containing DMEM, 10% FCS, Penicillin/Streptomycin, glutamine, and 0.5% (w/v) CHAPS. Transduction was carried out in a 37° C. incubator for 2-4 hours. After transduction, the cells were washed with fresh PBS solution to remove unbound SP1-TAT-GFP-Fc, and treated with 0.25% (w/v) Tyrpsin (in 0.25 mM EDTA) to digest away the loosely bound or the cell surface-attached SP1-TAT-GFP-Fc at 37° C. After trypsinization, the cells were washed and stabilized by centrifugation and resuspension in fresh PBS containing the 10% FCS solution for FACS analysis. Efficiency of intracellular protein transduction into HELA cells was quantified by measuring the amount of green fluorescence inside the cell. The specificity of the target cell protein receptors and the superior efficiency of the present technology shows that a transduction domain sequence component of the present invention can be designed and assembled using native secretion signal peptide sequences and secretion inhibition sequences and based on the nature of specific target cells will allow for development of protein therapy for specific intracellular deployment. Also, a secretion signal peptide sequence and/or secretion inhibition sequence with increased solubility and decreased hydrophobicity can also be combined in the present invention to provide highly soluble fusion proteins. Thus, the present invention can be applied to a wide variety of proteins.

Example 4

Transcription Initiation Through Intracellular Protein Delivery:

Here, we demonstrate that a functional protein, such as a transcription activator, can be delivered to mammalian cells using this invention to reverse gene repression and activate protein expression. In this example, a GFP structural gene is placed under the regulatory control of an HIV LTR (human immunodeficiency virus long terminal repeat) promoter that is repressed by the transcription factor complex TF11-I and USF-1 (see, Chen et al. (2005), J. Virol., 79, 4396). TF11-I and USF-I interact through a conserved R4 repeat protein domain that is in TFII-I. It has been demonstrated that overexpression of R4 repeat protein fragment effectively interferes with the interaction between TFII-I and USF-I. Disruption of TFII-1 and USF-1 complex by R4 repeat protein fragment has been shown to inhibit interaction of TFII-1:USF-1 binding the RBEI and RBEIII on the HIV LTR promoter region, leading to induction of HIV LTR-regulated protein expression (see, Malcolm et al. (2008), FEBS Lett., 582, 3903).

Figure 13:
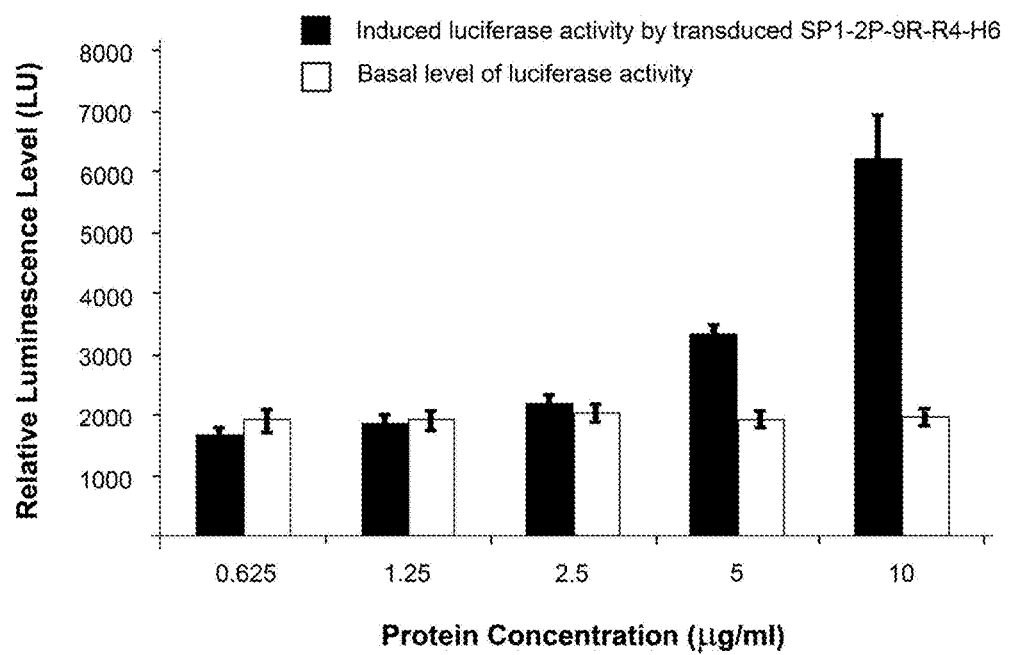
FIG. 13 is a bar graph showing intracellular delivery of SP1-2P-9R-SUMO-R4-H6 to activate gene expression. The cell permeable R4 repeat protein (SP1-2P-9R-SUMO-R4-H6) was added to the culture media at the indicated concentrations of Jurkat cells bearing a latent HIV reporter virus where luciferase was expressed under the control of the 5' long terminal repeat (LTR). Luciferase activity was measured 6 hours post-addition.

In this example, a recombinant protein consisting of R4 repeat protein was fused to SP1-2P-9R peptide sequence. As shown in FIG. 13, the R4 repeat protein was delivered into the intracellular environment of a cell and activated expression of the GFP reporter gene under the control of the HIV-LTR promoter.

Material and Methods

Cloning, Expression and Purification of SP1-2P-9R-SUMO-R4-H6 (SEQ ID:110 & 111):

The structural genes encoding SP1-2P-9R-SUMO and R4-H6 were separately synthesized by GenScript™ (Piscataway, N.J., USA). The gene fragment containing the SP1-2P-9R-SUMO was PCR amplified with forward and reverse primer (SEQ ID: 112 and 113, respectively), and digested with Nco1 and Nde1 restriction enzymes. The gene fragment containing the R4-H6 was PCR amplified with forward and reverse primer (SEQ ID: 114 and 115, respectively), and digested with Nde1 and Xho1 restriction enzymes. The two structural gene fragments were inserted by ligation to the Nco1 and Xho1 sites in pET-28a+ plasmid vector. The plasmid was verified by restriction mapping, followed by DNA sequencing. Expression of SP1-2P-9R-SUMO-R4-H6 was induced by addition of 1 mM IPTG (Isopropyl beta-D-1-thiogalactopyranoside) in E. coli BL21(DE3). Following cell lysis, the recombinant fusion protein of SP1-2P-9R-SUMO-R4-H6 was purified on Ni-chelating Sepharose™ resin.

Transduction Assay:

Human Jurkat T-lymphocytes that contain the integrated firefly luciferase gene (Photinus pyralis) and under the control of HIV-LTR promoter were subcultured and grown in the presence of 50 nM PMA (Phorbol 12-myristate 13-acetate) to a density of 8×10^5 cells/ml in microplate. SP1-2P-9R-SUMO-R4-H6 was added to the cell culture to a final concentration of 10 µg/mL to 0.08 µg/mL, and incubated for 6 hours at 37 degree Celsius. The luciferase substrates, D-Luciferin and ATP (from Promega Bright-Glo™ Luciferase Assay kit) was then added to 100 of the transduced cells and incubate at 37 degree Celsius for 5 minutes. Immediately, the luciferase luminscence was measured by a fluorescence plate reader to quantitate the level of gene expression and hence the activity of the transduced SP1-2P-9R-SUMO-R4-H6.

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the invention. Those of skill in the art will understand that use of various components as described above may cross-apply to combinations of different components not explicitly described but are within the scope and spirit of this invention. All patents, patent applications and other publications referred to herein are hereby incorporated by reference.

| U.S. patent DOCUMENTS | | | |
|---|---|---|---|
| 5,804,604 | Sep. 8, 1998 | Frankel et al. | (BIOGEN, HIV-1 TAT) |

| U.S. patent DOCUMENTS | | | |
|---|---|---|---|
| 5,807,746 | Sep. 15, 1998 | Lin et al. | (VANDERBILT, Signal Peptide) |
| 6,726,894 | Apr. 27, 2004 | Engberts et al. | (SYNVOLUX, Amphipathic lipid) |
| 6,780,846 | Aug. 24, 2004 | O'Mahony et al. | (ELAN, Amphipathic peptide) |
| 6,841,535 | Jan. 11, 2005 | Divita et al. | (ACTIVE MOTIF, Amphipathic peptide) |
| 2010/0197598 | Aug. 5, 2010 | Jo et al. | (PROCELL, Signal Peptide Truncation) |

OTHER PUBLICATIONS

Ausubel et al., (1989), "Current Protocols in Molecular Biology," Greene Publishing Associates and Wiley Interscience, N.Y.

Barkocy-Gallagher and Bassford, (1992), "Synthesis of precursor maltose-binding protein with proline in the +1 position of the cleavage site interferes with the activity of the Escherichia coli signal peptidase I in vivo." J. Biol. Chem., 267, 1231-1238, (PMID: 1730647).

Bohni et al. (1988), "SEC11 is required for signal peptide processing and yeast cell growth." J. Cell. Biol., 106, 1035, (PMID: 3283143).

Chaloin et al. (1998), "Design of Carrier Peptide-Oligonucleotide Conjugates with Rapid Membrane Translocation and Nuclear Localization Properties," Biochem. Biophys. Res. Commun., 243, 601-608, (PubMed: 9480855).

Chaloin et al. (1998), "Ionic channels formed by a primary amphipathic peptide containing a signal peptide and a nuclear localization sequence," Biochim. Biophys. Acta., 1375, 52-60, (PubMed: 9767105).

Chen et al. (2005), "TFII-I Regulates Induction of Chromosomally Integrated Human Immunodeficiency Virus Type 1 Long Terminal Repeat in Cooperation with USF," J. Virol., 79, 4396-4406, (PubMed: 15767439).

Cho et al. (2000), "Constructing High Complexity Synthetic Libraries of Long ORFs Using In Vitro Selection," J. Mol. Biol., 297, 309-319, (PMID: 10715203).

Derossi et al. (1996), "Cell internalization of the third helix of the Antennapedia homeodomain is receptor-independent," J. Biol. Chem., 271, 18188-18193, (PubMed: 8663410).

Doi et al. (2005), "High Solubility of Random-Sequence Proteins Consisting of Five Kinds of Primitive Amino Acids," Protein Eng. Des. Sel., 18, 279-284 (PMID: 15928003).

Evans et al. (1986), "Purification of microsomal signal peptidase as a complex." Proc. Natl. Acad. Sci. U.S.A., 83, 581, (PMID: 3511473).

Flinterman et al. (2009), "Delivery of Therapeutic Proteins as Secretable TAT Fusion Products," Mol. Ther., 17, 334-342, (PubMed: 19050698).

Jain et al. (1994), "Signal Peptide Cleavage Regions," 269, 16305-16310, (PubMed: 8206936)

Keefe and Szostak (2001), "Functional Proteins from A Random-Sequence Library," Nature, 410, 715-718, (PMID:11287961).

Koutsokeras and Kabouridis (2009), "Secretion and Uptake of TAT-fusion Proteins Produced by Engineered Mammalian Cells," Biochim. Biophys. Acta., 1790, 147-153, (PubMed: 19100310).

Lee et al. (2008), "Real-time fluorescence detection of protein transduction into live cells." J. Am. Chem. Soc., 130, 2398-2399, (PMID: 18251482).

Levine (1997), "P53, the Cellular Gatekeeper for Growth and Division," Cell, 88, 323-331 (PMID: 9039259).

Lin et al. (1995), "Inhibition of Nuclear Translocation of Transcription Factor NF-kB by a Synthetic Peptide Containing a Cell Membrane-permeable Motif and Nuclear Localization Sequence," J. Biol. Chem., 270, 14255-14258, (PubMed: 7782278).

Lundberg et al. (2003), "Cell Surface Adherence and Endocytosis of Protein Transduction Domains," Mol. Ther., 8, 143-150, (PubMed: 12842437).

Malcolm et al. (2008), "Specific interaction of TFII-1 with an upstream element on the HIV-1 LTR regulates induction of latent provirus," FEBS Lett., 582, 3903-3908, (PubMed: 18976654).

Matoba S and Ogrydziak DM, (1998), "Another factor besides hydrophobicity can affect signal peptide interaction with signal recognition particle." J. Biol. Chem., 273, 18841, (PMID: 9668059).

Meyer HA and Hartmann E, (1997), "The yeast SPC22/23 homolog Spc3P is essential for signal peptidase activity." J. Biol. Chem., 272, 13159, (PMID: 9148931).

Morris et al. (2001), "A peptide carrier for the delivery of biologically active protein into mammalian cells," Nat. Biotechnol., 19, 1173-1176 (PMID: 11731788).

Nilsson and Heijne, (1992), "A signal peptide with a proline next to the cleavage site inhibits leader peptidase when present in a sec-independent protein." FEBS Lett., 299, 243-246, (PMID: 1544500).

Paetzel et al. (2002), "Signal peptidases." Chem. Rev., 102, 4549, (PMID: 12475201).

Phelan et al. (1998), "Intracellular Delivery of Functional P53 by the Herpes virus Protein VP22," Nat. Biotechnol., 16, 440-443 (PMID: 9592391).

Remington (2005), "Remington: The Science and Practice of Pharmacy, 21st Edition," Lippincott Williams & Wilkins, the University of the Sciences in Philadelphia, P.A.

Richard et al. (2003), "Cell-penetrating peptides. A reevaluation of the mechanism of cellular uptake," J. Biol. Chem., 278, 585-590, (PubMed: 12411431).

Rothe C and Lehle L, (1998), "Sorting of invertase signal peptide mutants in yeast dependent and independent on the signal-recognition particle." Eur. J. Biochem., 252, 16, (PMID: 9523707).

Sambrook and Russell (2001), "Molecular Cloning: A Laboratory Manual, 3rd Edition," Cold Spring Harbor Laboratory, N.Y.

Shaw et al. (2008), "Comparison of Protein Transduction Domains in Mediating Cell Delivery of a Secreted CRE Protein," Biochemistry, 47, 1157-1166, (PubMed: 18179254).

Shen and Ryser (1978), "Conjugation of poly-L-lysine to albumin and horseradish peroxidase: a novel method of enhancing the cellular uptake of proteins," Proc. Natl. Acad. Sci. USA, 75, 1872-1876 (PMID: 273916).

Shen et al. (2011), "Expressed Cell-penetrating Peptides Can Induce a Bystander Effect, but Passage Through the Secretory Pathway Reduces Protein Transduction Activity," Mol. Ther., 19, 903-912, (PubMed: 21179011).

Stroud RM and Walter P, (1999), "Signal sequence recognition and protein targeting." Curr. Opin. Struct. Biol, 9, 754, (PMID: 10607673).

Tanaka et al. (2010), "Comparative Characterization of Random-Sequence Proteins Consisting of 5, 12, and 20 Kinds of Amino Acids," Protein Sci., 19, 786-795 (PMID: 20162614).

Valent et al. (1995), "Early events in preprotin recognition in E. coli: interaction of SRP and trigger factor with nascent polypeptides," EMBO J., 14, 5494, (PMID: 8521806).

Vives et al. (1997), "A truncated HIV-1 Tat protein basic domain rapidly translocates through the plasma membrane and accumulates in the cell nucleus," J. Biol. Chem., 272, 16010-16017, (PubMed: 9188504).

Von Heijne G and Abrahmsen L, (1989), "Species-specific variation in signal peptide design. Implications for protein secretion in foreign hosts," FEBS Lett., 244, 439, (PMID: 2646153).

Von Heijne G (1985), "Ribosome-SRP-signal sequence interactions. The relay helix hypothesis." FEBS Lett., 190, 1, (PMID: 3899724).

Wadia et al. (2004), "Transducible TAT-HA fusogenic peptide enhances escape of TAT-fusion proteins after lipid raft macropinocytosis." Nat. Med., 10, 310-315, (PMID: 14770178).

Wender et al., (2000), "The design, synthesis, and evaluation of molecules that enable or enhance cellular uptake: peptoid molecular transporters," Proc. Natl. Acad. Sci. USA, 97, 13003-13008 (PMID: 11087855).

YaDeau et al. (1991), "Yeast signal peptidase contains a glycoprotein and the Sec11 gene product." Proc. Natl. Acad. Sci. U.S.A., 88, 517, (PMID: 1846444).

Zheng N and Gierasch LM, (1996), "Signal sequences: the same yet different." Cell, 86, 849, (PMID: 8808619).

The invention claimed is:

1. A nucleic acid encoding a peptide, polypeptide or protein which comprises, in a N to a C-terminus direction, a secretion signal peptide fused directly to a cleavage inhibition peptide;
wherein the secretion signal peptide is capable of forming a complex with a signal recognition particle, wherein the secretion signal peptide is from 13 to 36 amino acids in length and comprises: (a) an amino terminal domain comprising one or more hydrophobic residues and optionally one or more basic residues; (b) a central hydrophobic domain comprising 6 to 15 residues; and (c) a carboxy terminal domain comprising a signal peptidase processing determinant comprising one or more polar uncharged residues, a peptidase cleavage site at the carboxy-terminus of the secretion signal peptide, and Ser, Ala, Gly or Val independently at each of −3 and −1 positions relative to the peptidase cleavage site; and
wherein the cleavage inhibition peptide prevents cleavage of the secretion signal peptide and is of formula $(XXX)_1(YYY)_n$, wherein each X is independently Pro, Arg or Lys, each Y is independently Arg or Lys and n is 1 or more.

2. The nucleic acid of claim 1, wherein the cleavage inhibition peptide comprises at least one proline.

3. The nucleic acid of claim 1, wherein the cleavage inhibition peptide comprises from four to ten lysine and/or arginine residues, arranged in tandem repeat.

4. The nucleic acid of claim 1, wherein the cleavage inhibition peptide comprises in the N to C-terminus direction, at least two proline residues followed by four or more adjacent lysine and/or arginine residues.

5. The nucleic acid of claim 1, wherein the cleavage inhibition peptide comprises in the N to C-terminus direction, two proline residues followed by about nine arginine residues.

6. The nucleic acid of claim 1, wherein the cleavage inhibition peptide is a HIV-1 TAT peptide.

7. The nucleic acid of claim 1, wherein the secretion signal peptide is a human placental alkaline phosphatase signal peptide.

8. A nucleic acid encoding a fusion protein cell, the fusion protein comprising a cargo portion intended for delivery into a cell and further comprising (a) in a direction towards the fusion protein N-terminus from the cargo portion: a cleavage inhibition peptide fused directly to a secretion signal peptide; or (b) in a direction towards the fusion protein C-terminus from said cargo portion: the secretion signal peptide fused directly to the cleavage inhibition peptide;
wherein the cargo portion is a peptide, polypeptide or protein which comprises an enzyme, a transcription factor, a cell growth regulator, an antibody, a reporter or a carrier that covalently attaches to or forms a complex with a secondary cargo, and wherein the cargo portion is in a functional and structured conformational state;
wherein the secretion signal peptide is capable of forming a complex with a signal recognition particle, wherein the secretion signal peptide is from 13 to 36 amino acids in length and comprises: (a) an amino terminal domain comprising one or more hydrophobic residues and optionally one or more basic residues; (b) a central hydrophobic domain comprising 6 to 15 residues; and (c) a carboxy-terminal domain comprising a signal peptidase processing determinant comprising one or more polar uncharged residues, a peptidase cleavage site at the carboxy-terminus of the secretion signal peptide, and Ser, Ala, Gly or Val independently at each of −3 and −1 positions relative to the peptidase cleavage site; and
wherein the cleavage inhibition peptide prevents cleavage of the secretion signal peptide and is of formula $(XXX)_1(YYY)_n$, wherein each X is independently Pro, Arg or Lys, each Y is independently Arg or Lys and n is 1 or more.

9. The nucleic acid of claim 8, wherein the cleavage inhibition peptide comprises at least one proline.

10. The nucleic acid of claim 8, wherein the cleavage inhibition peptide comprises from four to ten lysine and/or arginine residues, arranged in tandem repeat.

11. The nucleic acid of claim 8, wherein the cleavage inhibition peptide comprises in an N to C-terminal direction, at least two proline residues followed by four or more adjacent lysine and/or arginine residues.

12. The nucleic acid of claim 8, wherein the cleavage inhibition peptide comprises in an N to C-terminus direction, two proline residues followed by about nine arginine residues.

13. The nucleic acid of claim 8, wherein the cleavage inhibition peptide is a HIV-1 TAT peptide.

14. The nucleic acid of claim 8, wherein the secretion signal peptide is a human placental alkaline phosphatase signal peptide.

15. The nucleic acid of claim 8, wherein the fusion protein comprises, in the direction towards the fusion protein N-terminus from the cargo portion: the cleavage inhibition peptide fused directly to the secretion signal peptide.

16. The nucleic acid of claim 8, wherein the fusion protein comprises, in the direction towards the fusion protein C-terminus from said cargo portion: the secretion signal peptide fused directly to the cleavage inhibition peptide.

* * * * *

SEQUENCE LISTING

<160> NUMBER OF SEQ ID NOS: 115

<210> SEQ ID NO 1
<211> LENGTH: 22
<212> TYPE: PRT
<213> ORGANISM: Homo sapiens

<400> SEQUENCE: 1

Met Leu Gly Pro Cys Met Leu Leu Leu Leu Leu Leu Gly Leu Arg
1               5                   10                  15

Leu Pro Gly Val Trp Ala
            20

```
<210> SEQ ID NO 2
<211> LENGTH: 66
<212> TYPE: DNA
<213> ORGANISM: Homo sapiens

<400> SEQUENCE: 2
atgctggggc cctgcatgct gctgctgctg ctgctgctgg gcctgaggct gcccggggtg    60
tgggct                                                                66

<210> SEQ ID NO 3
<211> LENGTH: 9
<212> TYPE: PRT
<213> ORGANISM: Human immunodeficiency virus type 1

<400> SEQUENCE: 3

Arg Lys Lys Arg Arg Gln Arg Arg Arg
1               5

<210> SEQ ID NO 4
<211> LENGTH: 27
<212> TYPE: DNA
<213> ORGANISM: Human immunodeficiency virus type 1

<400> SEQUENCE: 4
aggaagaaga ggaggcagag gagaagg                                         27

<210> SEQ ID NO 5
<211> LENGTH: 9
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 5

Arg Arg Arg Arg Arg Arg Arg Arg Arg
1               5

<210> SEQ ID NO 6
<211> LENGTH: 27
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 6
aggagaaggc gcaggagaag gcgcaga                                         27

<210> SEQ ID NO 7
<211> LENGTH: 31
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 7

Met Leu Gly Pro Cys Met Leu Leu Leu Leu Leu Leu Leu Gly Leu Arg
1               5                   10                  15

Leu Pro Gly Val Trp Ala Arg Lys Lys Arg Gln Arg Arg Arg
            20                  25                  30

<210> SEQ ID NO 8
<211> LENGTH: 93
<212> TYPE: DNA
<213> ORGANISM: Artificial Sequence
```

```
<220> FEATURE:
<223> OTHER INFORMATION: Custom Designed by IPROGEN BIOTECH INC.

<400> SEQUENCE: 8
atgctggggc cctgcatgct gctgctgctg ctgctgctgg gcctgaggct gcccggggtg      60
tgggctagga agaagaggag gcagaggaga agg                                  93

<210> SEQ ID NO 9
<211> LENGTH: 16
<212> TYPE: PRT
<213> ORGANISM: Homo sapiens

<400> SEQUENCE: 9

Ala Ala Val Ala Leu Leu Pro Ala Val Leu Leu Ala Leu Leu Ala Pro
1               5                   10                  15

<210> SEQ ID NO 10
<211> LENGTH: 48
<212> TYPE: DNA
<213> ORGANISM: Homo sapiens

<400> SEQUENCE: 10
gccgccgtgg ccctgctgcc cgccgtgctg ctggccctgc tggccccc                  48

<210> SEQ ID NO 11
<211> LENGTH: 21
<212> TYPE: PRT
<213> ORGANISM: Homo sapiens

<400> SEQUENCE: 11

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 12
<211> LENGTH: 63
<212> TYPE: DNA
<213> ORGANISM: Homo sapiens

<400> SEQUENCE: 12
aaggagacct ggtgggagac ctggtggacc gagtggagcc agcccaagaa gaagcggaag      60
gtg                                                                   63

<210> SEQ ID NO 13
<211> LENGTH: 15
<212> TYPE: PRT
<213> ORGANISM: Artificial Sequence
<220> FEATURE:
<223> OTHER INFORMATION: ZELAN094 in U.S. Patent No. 6,780,846B1

<400> SEQUENCE: 13

Lys Lys Ala Ala Ala Val Leu Leu Pro Val Leu Leu Ala Ala Pro
1               5                   10                  15

<210> SEQ ID NO 14
<211> LENGTH: 45
<212> TYPE: DNA
<213> ORGANISM: Artificial Sequence
<220> FEATURE:
<223> OTHER INFORMATION: ZELAN094 in U.S. Patent No. 6,780,846B1

<400> SEQUENCE: 14
```
aagaaggccg ccgccgtgct gctgcccgtg ctgctggccg cccc    45

<210> SEQ ID NO 15
<211> LENGTH: 7
<212> TYPE: PRT
<213> ORGANISM: Artificial Sequence
<220> FEATURE:
<223> OTHER INFORMATION: JO-78 in U.S. Patent No. 2010/0197598

<400> SEQUENCE: 15

Val Leu Leu Ala Val Thr Pro
1               5

<210> SEQ ID NO 16
<211> LENGTH: 21
<212> TYPE: DNA
<213> ORGANISM: Artificial Sequence
<220> FEATURE:
<223> OTHER INFORMATION: JO-78 in U.S. Patent No. 2010/0197598

<400> SEQUENCE: 16
gtgctgctgg ccgtgacccc c    21

<210> SEQ ID NO 17
<211> LENGTH: 8
<212> TYPE: PRT
<213> ORGANISM: Artificial Sequence
<220> FEATURE:
<223> OTHER INFORMATION: JO-118 in U.S. Patent No. 2010/0197598

<400> SEQUENCE: 17

Ala Val Val Val Ala Leu Ala Pro
1               5

<210> SEQ ID NO 18
<211> LENGTH: 24
<212> TYPE: DNA
<213> ORGANISM: Artificial Sequence
<220> FEATURE:
<223> OTHER INFORMATION: JO-118 in U.S. Patent No. 2010/0197598

<400> SEQUENCE: 18
gccgtggtgg tggccctggc cccc    24

<210> SEQ ID NO 19
<211> LENGTH: 10
<212> TYPE: PRT
<213> ORGANISM: Artificial Sequence
<220> FEATURE:
<223> OTHER INFORMATION: JO-178 in U.S. Patent No. 2010/0197598

<400> SEQUENCE: 19

Leu Val Leu Ala Ala Pro Ala Ala Leu Pro
1               5                   10

<210> SEQ ID NO 20
<211> LENGTH: 30
<212> TYPE: DNA
<213> ORGANISM: Artificial Sequence
<220> FEATURE:
<223> OTHER INFORMATION: JO-178 in U.S. Patent No. 2010/0197598

<400> SEQUENCE: 20
ctggtgctgg ccgcccccgc cgccctgccc    30

<210> SEQ ID NO 21

<211> LENGTH: 18
<212> TYPE: PRT
<213> ORGANISM: Homo sapiens

<400> SEQUENCE: 21

Ser Gly Arg Gln Ile Lys Ile Trp Phe Gln Asn Arg Arg Met Lys Trp
1               5                   10                  15

Lys Lys

<210> SEQ ID NO 22
<211> LENGTH: 54
<212> TYPE: DNA
<213> ORGANISM: Homo sapiens

<400> SEQUENCE: 22
agcggccggc agatcaagat ctggttccag aaccggcgga tgaagtggaa gaag         54

<210> SEQ ID NO 23
<211> LENGTH: 21
<212> TYPE: PRT
<213> ORGANISM: Homo sapiens

<400> SEQUENCE: 23

Leu Gly Pro Cys Met Leu Leu Leu Leu Leu Leu Gly Leu Arg Leu
1               5                   10                  15

Pro Gly Val Trp Ala
            20

<210> SEQ ID NO 24
<211> LENGTH: 63
<212> TYPE: DNA
<213> ORGANISM: Homo sapiens

<400> SEQUENCE: 24
ctgggacctt gcatgctgct gctgctgctg ctgctgggcc tgaggctgcc tggcgtgtgg   60
gcc                                                                63

<210> SEQ ID NO 25
<211> LENGTH: 21
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 25

Ala Trp Val Gly Pro Leu Arg Leu Gly Leu Leu Leu Leu Leu Leu
1               5                   10                  15

Met Cys Pro Gly Leu
            20

<210> SEQ ID NO 26
<211> LENGTH: 63
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 26
gcctgggtgg gacctctgag gctgggcctg ctgctgctgc tgctgctgat gtgccctggc   60
ctg                                                                63

<210> SEQ ID NO 27

```
<211> LENGTH: 7
<212> TYPE: PRT
<213> ORGANISM: Simian virus 40

<400> SEQUENCE: 27

Pro Lys Lys Lys Arg Lys Val
1               5

<210> SEQ ID NO 28
<211> LENGTH: 21
<212> TYPE: DNA
<213> ORGANISM: Simian virus 40

<400> SEQUENCE: 28
ccgaaaaaaa aacgtaaagt c                                                   21

<210> SEQ ID NO 29
<211> LENGTH: 26
<212> TYPE: PRT
<213> ORGANISM: Homo sapiens

<400> SEQUENCE: 29

Arg Val Val Arg Ala Ala Leu Pro Leu Gln Leu Leu Leu Leu Leu Leu
1               5                   10                  15

Leu Leu Leu Ala Cys Leu Leu Pro Ser Ser
            20                  25

<210> SEQ ID NO 30
<211> LENGTH: 78
<212> TYPE: DNA
<213> ORGANISM: Homo sapiens

<400> SEQUENCE: 30
cgtgtggtcc gtgccgctct gcctctgcaa ctgctgctgc tgctgctgct gctgctggct         60
tgtctgctgc cttcttcc                                                       78

<210> SEQ ID NO 31
<211> LENGTH: 97
<212> TYPE: PRT
<213> ORGANISM: Homo sapiens

<400> SEQUENCE: 31

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly

<210> SEQ ID NO 32
<211> LENGTH: 291
<212> TYPE: DNA
<213> ORGANISM: Homo sapiens
```

<400> SEQUENCE: 32

```
atgagcgacc aggaggctaa accttctact gaggatctgg gcgataaaaa agagggcgag        60
tatatcaaac tgaaagtgat tggccaagac tctagcgaaa tccattttaa agtgaaaatg       120
accacccacc tgaaaaaact gaaagaatcc tattgtcagc gtcagggtgt accgatgaat       180
agtctgcgct tcctgtttga aggacagcgt attgccgata accataccc taaagaactg       240 ggcatggagg aggaggacgt tattgaggtc tatcaagagc aaaccggtgg a                291
```

<210> SEQ ID NO 33
<211> LENGTH: 31
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 33

```
Met Leu Gly Pro Cys Met Leu Leu Leu Leu Leu Leu Gly Leu Arg
1               5                   10                  15

Leu Pro Gly Val Trp Ala Arg Arg Arg Arg Arg Arg Arg Arg
            20                  25                  30
```

<210> SEQ ID NO 34
<211> LENGTH: 93
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 34

```
atgctgggcc cttgcatgct gctgctgctg ctgctgctgg gcctgaggct gcctggcgtc        60
tgggccagga aaggcgcag agaaggcgc aga                                       93
```

<210> SEQ ID NO 35
<211> LENGTH: 31
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 35

```
Arg Arg Arg Arg Arg Arg Arg Arg Arg Met Leu Gly Pro Cys Met Leu
1               5                   10                  15

Leu Leu Leu Leu Leu Leu Gly Leu Arg Leu Pro Gly Val Trp Ala
            20                  25                  30
```

<210> SEQ ID NO 36
<211> LENGTH: 93
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 36

```
aggagaaggc gcaggagaag gcgcagaatg ctgggccctt gcatgctgct gctgctgctg        60
ctgctgggcc tgaggctgcc tggcgtctgg gcc                                     93
```

<210> SEQ ID NO 37
<211> LENGTH: 31
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 37

Met Leu Gly Pro Cys Met Leu Leu Leu Leu Leu Leu Gly Leu Arg
1               5                   10                  15

Leu Gln Leu Ser Leu Gly Arg Lys Lys Arg Gln Arg Arg
            20                  25                  30

<210> SEQ ID NO 38
<211> LENGTH: 93
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 38
atgctgggcc cctgcatgct gctgctgctg ctgctgctgg gcctgaggct ccagctgagc     60
ctgggcagga agaagaggag gcagaggaga agg                                  93

<210> SEQ ID NO 39
<211> LENGTH: 27
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 39

Met Leu Gly Pro Cys Met Leu Leu Leu Leu Leu Leu Gly Leu Arg
1               5                   10                  15

Leu Gln Leu Ser Leu Ala Pro Gly Gly Gly Gly
            20                  25

<210> SEQ ID NO 40
<211> LENGTH: 81
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 40
atgctgggcc cctgcatgct gctgctgctg ctgctgctgg gcctgaggct ccagctgagc     60 ctggccccccg ggggaggtgg c                                              81

<210> SEQ ID NO 41
<211> LENGTH: 25
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 41

Met Leu Gly Pro Cys Met Leu Leu Leu Leu Leu Leu Gly Leu Arg
1               5                   10                  15

Leu Pro Gly Val Trp Ala Pro Pro Pro
            20                  25

<210> SEQ ID NO 42
<211> LENGTH: 75
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 42

```
atgctgggcc cttgcatgct gctgctgctg ctgctgctgg gcctgaggct gcctggcgtc    60
tgggccccgc cacct                                                     75
```

<210> SEQ ID NO 43
<211> LENGTH: 26
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 43

```
Met Leu Gly Pro Cys Met Leu Leu Leu Leu Leu Leu Gly Leu Arg
1               5                  10                  15

Leu Arg Arg Arg Arg Arg Arg Arg Arg Arg
            20                  25
```

<210> SEQ ID NO 44
<211> LENGTH: 78
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 44

```
atgctgggcc cttgcatgct gctgctgctg ctgctgctgg gcctgaggct gaggagaagg    60
cgcaggagaa ggcgcaga                                                  78
```

<210> SEQ ID NO 45
<211> LENGTH: 15
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 45

```
Met Pro Gly Val Trp Ala Arg Arg Arg Arg Arg Arg Arg Arg Arg
1               5                  10                  15
```

<210> SEQ ID NO 46
<211> LENGTH: 45
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 46

```
atgcctggcg tctgggccag gagaaggcgc aggagaaggc gcaga                    45
```

<210> SEQ ID NO 47
<211> LENGTH: 22
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 47

```
Met Leu Gly Pro Cys Met Leu Leu Leu Leu Leu Leu Gly Leu Arg
1               5                  10                  15

Leu Pro Gly Arg Arg Arg
            20
```

<210> SEQ ID NO 48
<211> LENGTH: 66
<212> TYPE: DNA

<213> ORGANISM: Artificial Sequence
<220> FEATURE:
<223> OTHER INFORMATION: Custom Designed by IPROGEN BIOTECH INC.

<400> SEQUENCE: 48
atgctggggc cctgcatgct gctgctgctg ctgctgctgg gcctgaggct gcccgggagg   60
aggagg   66

<210> SEQ ID NO 49
<211> LENGTH: 239
<212> TYPE: PRT
<213> ORGANISM: Artificial Sequence
<220> FEATURE:
<223> OTHER INFORMATION: enhanced green fluorescent protein

<400> SEQUENCE: 49

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 50
<211> LENGTH: 717
<212> TYPE: DNA
<213> ORGANISM: Artificial Sequence
<220> FEATURE:
<223> OTHER INFORMATION: enhanced Green Fluorescent Protein

<400> SEQUENCE: 50
atggtgagca agggcgagga gctgttcacc ggggtggtgc ccatcctggt cgagctggac   60
ggcgacgtaa acggccacaa gttcagcgtg tccggcgagg gcgagggcga tgccacctac  120

-continued

```
ggcaagctga ccctgaagtt catctgcacc accggcaagc tgcccgtgcc ctggcccacc    180
ctcgtgacca ccctgaccta cggcgtgcag tgcttcagcc gctacccgga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaag       717
```

<210> SEQ ID NO 51
<211> LENGTH: 226
<212> TYPE: PRT
<213> ORGANISM: Homo sapiens

<400> SEQUENCE: 51

```
Lys Thr His Thr Cys Pro Pro Cys Pro Ala Pro Glu Leu Leu Gly Gly
1               5                   10                  15
Pro Ser Val Phe Leu Phe Pro Pro Lys Pro Lys Asp Thr Leu Met Ile
            20                  25                  30
Ser Arg Thr Pro Glu Val Thr Cys Val Val Val Asp Val Ser His Glu
        35                  40                  45
Asp Pro Glu Val Lys Phe Asn Trp Tyr Val Asp Gly Val Glu Val His
    50                  55                  60
Asn Ala Lys Thr Lys Pro Arg Glu Glu Gln Tyr Asn Ser Thr Tyr Arg
65                  70                  75                  80
Val Val Ser Val Leu Thr Val Leu His Gln Asp Trp Leu Asn Gly Lys
                85                  90                  95
Glu Tyr Lys Cys Lys Val Ser Asn Lys Ala Leu Pro Ala Pro Ile Glu
            100                 105                 110
Lys Thr Ile Ser Lys Ala Lys Gly Gln Pro Arg Glu Pro Gln Val Tyr
        115                 120                 125
Thr Leu Pro Pro Ser Arg Asp Glu Leu Thr Lys Asn Gln Val Ser Leu
    130                 135                 140
Thr Cys Leu Val Lys Gly Phe Tyr Pro Ser Asp Ile Ala Val Glu Trp
145                 150                 155                 160
Glu Ser Asn Gly Gln Pro Glu Asn Asn Tyr Lys Thr Thr Pro Pro Val
                165                 170                 175
Leu Asp Ser Asp Gly Ser Phe Phe Leu Tyr Ser Lys Leu Thr Val Asp
            180                 185                 190
Lys Ser Arg Trp Gln Gln Gly Asn Val Phe Ser Cys Ser Val Met His
        195                 200                 205
Glu Ala Leu His Asn His Tyr Thr Gln Lys Ser Leu Ser Leu Ser Pro
    210                 215                 220
Gly Lys
225
```

<210> SEQ ID NO 52
<211> LENGTH: 678
<212> TYPE: PRT
<213> ORGANISM: Homo sapiens -continued

```
<400> SEQUENCE: 52

Ala Ala Ala Ala Cys Thr Cys Ala Cys Ala Cys Ala Thr Gly Cys Cys
1               5                   10                  15

Cys Ala Cys Cys Gly Thr Gly Cys Cys Cys Ala Gly Cys Ala Cys Cys
            20                  25                  30

Thr Gly Ala Ala Cys Thr Cys Cys Thr Gly Gly Gly Gly Gly Gly Ala
        35                  40                  45

Cys Cys Gly Thr Cys Ala Gly Thr Cys Thr Thr Cys Cys Thr Cys Thr
    50                  55                  60

Thr Cys Cys Cys Cys Cys Cys Ala Ala Ala Ala Cys Cys Cys Ala Ala
65                  70                  75                  80

Gly Gly Ala Cys Ala Cys Cys Cys Thr Cys Ala Thr Gly Ala Thr Cys
                85                  90                  95

Thr Cys Cys Cys Gly Gly Ala Cys Cys Cys Cys Thr Gly Ala Gly Gly
            100                 105                 110

Thr Cys Ala Cys Ala Thr Gly Cys Gly Thr Gly Gly Thr Gly Gly Thr
        115                 120                 125

Gly Gly Ala Cys Gly Thr Gly Ala Gly Cys Cys Ala Cys Gly Ala Ala
    130                 135                 140

Gly Ala Cys Cys Cys Thr Gly Ala Gly Gly Thr Cys Ala Ala Gly Thr
145                 150                 155                 160

Thr Cys Ala Ala Cys Thr Gly Gly Thr Ala Cys Gly Thr Gly Gly Ala
                165                 170                 175

Cys Gly Gly Cys Gly Thr Gly Gly Ala Gly Gly Thr Gly Cys Ala Thr
            180                 185                 190

Ala Ala Thr Gly Cys Cys Ala Ala Gly Ala Cys Ala Ala Ala Gly Cys
        195                 200                 205

Cys Gly Cys Gly Gly Gly Ala Gly Gly Ala Gly Cys Ala Gly Thr Ala
    210                 215                 220

Cys Ala Ala Cys Ala Gly Cys Ala Cys Gly Thr Ala Cys Cys Gly Thr
225                 230                 235                 240

Gly Thr Gly Gly Thr Cys Ala Gly Cys Gly Thr Cys Cys Thr Cys Ala
                245                 250                 255

Cys Cys Gly Thr Cys Cys Thr Gly Cys Ala Cys Cys Ala Gly Gly Ala
            260                 265                 270

Cys Thr Gly Gly Cys Thr Gly Ala Ala Thr Gly Gly Cys Ala Ala Gly
        275                 280                 285

Gly Ala Gly Thr Ala Cys Ala Ala Gly Thr Gly Cys Ala Ala Gly Gly
    290                 295                 300

Thr Cys Thr Cys Cys Ala Ala Cys Ala Ala Ala Gly Cys Cys Cys Thr
305                 310                 315                 320

Cys Cys Cys Ala Gly Cys Cys Cys Cys Cys Ala Thr Cys Gly Ala Gly
                325                 330                 335

Ala Ala Ala Ala Cys Cys Ala Thr Cys Thr Cys Cys Ala Ala Ala Gly
            340                 345                 350

Cys Cys Ala Ala Ala Gly Gly Gly Cys Ala Gly Cys Cys Cys Cys Gly
        355                 360                 365

Ala Gly Ala Ala Cys Cys Ala Cys Ala Gly Gly Thr Gly Thr Ala Cys
    370                 375                 380

Ala Cys Cys Cys Thr Gly Cys Cys Cys Cys Cys Ala Thr Cys Cys Cys
385                 390                 395                 400

Gly Gly Gly Ala Thr Gly Ala Gly Cys Thr Gly Ala Cys Cys Ala Ala
                405                 410                 415
```

```
Gly Ala Ala Cys Cys Ala Gly Gly Thr Cys Ala Gly Cys Cys Thr Gly
                420                 425                 430

Ala Cys Cys Thr Gly Cys Thr Gly Gly Thr Cys Ala Ala Gly
            435                 440                 445

Gly Cys Thr Thr Cys Thr Ala Thr Cys Cys Ala Gly Cys Gly Ala
        450                 455                 460

Cys Ala Thr Cys Gly Cys Gly Thr Gly Ala Gly Thr Gly Gly
465                 470                 475                 480

Gly Ala Gly Ala Gly Cys Ala Ala Thr Gly Gly Cys Ala Gly Cys
                485                 490                 495

Cys Gly Gly Ala Gly Ala Ala Cys Ala Ala Cys Thr Ala Cys Ala Ala
            500                 505                 510

Gly Ala Cys Cys Ala Cys Gly Cys Cys Thr Cys Cys Gly Thr Gly
        515                 520                 525

Cys Thr Gly Gly Ala Cys Thr Cys Cys Gly Ala Cys Gly Gly Cys Thr
530                 535                 540

Cys Cys Thr Thr Cys Thr Thr Cys Cys Thr Cys Thr Ala Cys Ala Gly
                545                 550                 555                 560

Cys Ala Ala Gly Cys Thr Cys Ala Cys Cys Gly Thr Gly Gly Ala Cys
            565                 570                 575

Ala Ala Gly Ala Gly Cys Ala Gly Gly Thr Gly Gly Cys Ala Gly Cys
        580                 585                 590

Ala Gly Gly Gly Gly Ala Ala Cys Gly Thr Cys Thr Thr Cys Thr Cys
                595                 600                 605

Ala Thr Gly Cys Thr Cys Cys Gly Thr Gly Ala Thr Gly Cys Ala Thr
        610                 615                 620

Gly Ala Gly Gly Cys Thr Cys Thr Gly Cys Ala Cys Ala Ala Cys Cys
625                 630                 635                 640

Ala Cys Thr Ala Cys Ala Cys Gly Cys Ala Gly Ala Ala Gly Ala Gly
                645                 650                 655

Cys Cys Thr Cys Thr Cys Cys Cys Thr Gly Thr Cys Thr Cys Cys Gly
            660                 665                 670

Gly Gly Thr Ala Ala Ala
        675

<210> SEQ ID NO 53
<211> LENGTH: 6
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 53

Glu Phe Gly Ser Gly Ser
1               5

<210> SEQ ID NO 54
<211> LENGTH: 18
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 54
gaattcggca gcggcagc                                                    18

<210> SEQ ID NO 55
```

-continued

```
<211> LENGTH: 471
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 55

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Glu
225                 230                 235                 240

Phe Gly Ser Gly Ser Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
370                 375                 380
```

```
Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 56
<211> LENGTH: 1413
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 56
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctacccega ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaaggaa     720
ttcggcagcg gcagcaaaac tcacacatgc ccaccgtgcc cagcacctga actcctgggg     780
ggaccgtcag tcttcctctt ccccccaaaa cccaaggaca cctcatgat ctcccggacc     840
cctgaggtca catgcgtggt ggtggacgtg agccacgaag accctgaggt caagttcaac     900
tggtacgtgg acggcgtgga ggtgcataat gccaagacaa agccgcggga ggagcagtac     960
aacagcacgt accgtgtggt cagcgtcctc accgtcctgc accaggactg gctgaatggc    1020
aaggagtaca agtgcaaggt ctccaacaaa gccctcccag cccccatcga gaaaaccatc    1080
tccaaagcca aagggcagcc ccgagaacca caggtgtaca ccctgccccc atcccgggat    1140
gagctgacca agaaccaggt cagcctgacc tgcctggtca aaggcttcta tcccagcgac    1200
atcgccgtgg agtgggagag caatgggcag ccggagaaca actacaagac cacgcctccc    1260
gtgctggact ccgacggctc cttcttcctc tacagcaagc tcaccgtgga caagagcagg    1320
tggcagcagg ggaacgtctt ctcatgctcc gtgatgcatg aggctctgca caaccactac    1380
acgcagaaga gcctctccct gtctccgggt aaa                                 1413

<210> SEQ ID NO 57
```

<211> LENGTH: 1425
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 57

| | | | | | |
|---|---|---|---|---|---|
| gagctcagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagtt | catctgcacc | accggcaagc | tgcccgtgcc | ctggcccacc | 180 |
| ctcgtgacca | ccctgaccta | cggcgtgcag | tgcttcagcc | gctacccgga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacaa | cagccacaac | gtctatatca | tggccgacaa | gcagaagaac | 480 |
| ggcatcaagg | tgaacttcaa | gatccgccac | aacatcgagg | acggcagcgt | gcagctcgcc | 540 |
| gaccactacc | agcagaacac | ccccatcggc | gacggccccg | tgctgctgcc | cgacaaccac | 600 |
| tacctgagca | cccagtccgc | cctgagcaaa | gaccccaacg | agaagcgcga | tcacatggtc | 660 |
| ctgctggagt | tcgtgaccgc | cgccgggatc | actctcggca | tggacgagct | gtacaaggaa | 720 |
| ttcggttctg | gttctaaaac | tcacacatgc | ccaccgtgcc | cagcacctga | actcctgggg | 780 |
| ggaccgtcag | tcttcctctt | ccccccaaaa | cccaaggaca | ccctcatgat | ctcccggacc | 840 |
| cctgaggtca | catgcgtggt | ggtggacgtg | agccacgaag | accctgaggt | caagttcaac | 900 |
| tggtacgtgg | acggcgtgga | ggtgcataat | gccaagacaa | agccgcggga | ggagcagtac | 960 |
| aacagcacgt | accgtgtggt | cagcgtcctc | accgtcctgc | accaggactg | gctgaatggc | 1020 |
| aaggagtaca | agtgcaaggt | ctccaacaaa | gccctcccag | ccccatcga | gaaaaccatc | 1080 |
| tccaaagcca | aagggcagcc | ccgagaacca | caggtgtaca | ccctgccccc | atcccgggat | 1140 |
| gagctgacca | agaaccaggt | cagcctgacc | tgcctggtca | aaggcttcta | tcccagcgac | 1200 |
| atcgccgtgg | agtgggagag | caatgggcag | ccggagaaca | actacaagac | cacgcctccc | 1260 |
| gtgctggact | ccgacggctc | cttcttcctc | tacagcaagc | tcaccgtgga | caagagcagg | 1320 |
| tggcagcagg | ggaacgtctt | ctcatgctcc | gtgatgcatg | aggctctgca | caaccactac | 1380 |
| acgcagaaga | gcctctccct | gtctccgggt | aaatgatgac | tcgag | | 1425 |

<210> SEQ ID NO 58
<211> LENGTH: 324
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 58

| | | | | | |
|---|---|---|---|---|---|
| tcccgggatg | agctgaccaa | gaaccaggtc | agcctgacct | gcctggtcaa | aggcttctat | 60 |
| cccagcgaca | tcgccgtgga | gtgggagagc | aatgggcagc | cggagaacaa | ctacaagacc | 120 |
| acgcctcccg | tgctggactc | cgacggctcc | ttcttcctct | acagcaagct | caccgtggac | 180 |
| aagagcaggt | ggcagcaggg | gaacgtcttc | tcatgctccg | tgatgcatga | ggctctgcac | 240 |
| aaccactaca | cgcagaagag | cctctccctg | tctccgggta | aaggaagaa | gaggaggcag | 300 |
| aggagaaggt | gatgataact | cgag | | | | 324 |

```
<210> SEQ ID NO 59
<211> LENGTH: 360
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 59
tcccgggatg agctgaccaa gaaccaggtc agcctgacct gcctggtcaa aggcttctat      60
cccagcgaca tcgccgtgga gtgggagagc aatgggcagc cggagaacaa ctacaagacc     120
acgcctcccg tgctggactc cgacggctcc ttcttcctct acagcaagct caccgtggac     180
aagagcaggt ggcagcaggg gaacgtcttc tcatgctccg tgatgcatga ggctctgcac     240
aaccactaca cgcagaagag cctctcccTG tctccgggta aactgggacc ttgcatgctg     300
ctgctgctgc tgctgctggg cctgaggctg cctggcgtgt gggcctgata gtaactcgag     360

<210> SEQ ID NO 60
<211> LENGTH: 360
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 60
tcccgggatg agctgaccaa gaaccaggtc agcctgacct gcctggtcaa aggcttctat      60
cccagcgaca tcgccgtgga gtgggagagc aatgggcagc cggagaacaa ctacaagacc     120
acgcctcccg tgctggactc cgacggctcc ttcttcctct acagcaagct caccgtggac     180
aagagcaggt ggcagcaggg gaacgtcttc tcatgctccg tgatgcatga ggctctgcac     240
aaccactaca cgcagaagag cctctcccTG tctccgggta aagcctgggt gggccctctg     300
aggctgggcc tgctgctgct gctgctgctg atgtgccctg actgtgata gtaactcgag      360

<210> SEQ ID NO 61
<211> LENGTH: 546
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 61
ggatccacaa ttcccctcta gaaataattt tgtttaactt taagaaggag atataccatg      60
ccgaaaaaaa aacgtaaagt ccgtgtggtc cgtgccgctc tgcctctgca actgctgctg     120
ctgctgctgc tgctgctggc ttgtctgctg ccttcttccg gtaatgttcc tgaactgcct     180
gatacaactg agcatagccg tactgatctg atgagcgacc aggaggctaa accttctact     240
gaggatctgg gcgataaaaa agagggcgag tatatcaaac tgaaagtgat ggccaagac      300 tctagcgaaa tccattttaa agtgaaaatg accacccacc tgaaaaaact gaagaatcc      360 tattgtcagc gtcagggtgt accgatgaat agtctgcgct tcctgtttga aggacagcgt     420
attgccgata accataccccc taagaactg gcatggagg aggaggacgt tattgaggtc      480
tatcaagagc aaaccggtgg aggcggtaaa aaaaaacgta agtggccat ggtgagcaag      540 aagctt                                                              546

<210> SEQ ID NO 62
<211> LENGTH: 528
<212> TYPE: DNA
<213> ORGANISM: Artificial Sequence
<220> FEATURE:
```

<223> OTHER INFORMATION: Custom Designed by IPROGEN BIOTECH INC.

<400> SEQUENCE: 62

```
ggatccacaa ttcccctcta gaaataattt tgtttaactt taagaaggag ataccatg      60
ccgaaaaaaa aacgtaaagt ccgtgtggtc cgtgccgctc tgcctctgca actgctgctg   120
ctgctgctgc tgctgctggc ttgtctgctg ccttcttccg gtaatgttcc tgaactgcct   180
gatacaactg agcatagccg tactgatctg atgagcgacc aggaggctaa accttctact   240
gaggatctgg gcgataaaaa agagggcgag tatatcaaac tgaaagtgat tggccaagac   300
tctagcgaaa tccattttaa agtgaaaatg accacccacc tgaaaaaact gaaagaatcc   360
tattgtcagc gtcagggtgt accgatgaat agtctgcgct tcctgtttga aggacagcgt   420
attgccgata accatacccc taaagaactg ggcatggagg aggaggacgt tattgaggtc   480
tatcaagagc aaaccggtgg aggcggtgcc atggtgagca agaagctt              528
```

<210> SEQ ID NO 63
<211> LENGTH: 237
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 63

```
ggatccacaa ttcccctcta gaaataattt tgtttaactt taagaaggag ataccatg      60
ccgaaaaaaa aacgtaaagt ccgtgtggtc cgtgccgctc tgcctctgca actgctgctg   120
ctgctgctgc tgctgctggc ttgtctgctg ccttcttccg gtaatgttcc tgaactgcct   180
gatacaactg agcatagccg tactgatctg ggcggtgcca tggtgagcaa gaagctt     237
```

<210> SEQ ID NO 64
<211> LENGTH: 216
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 64

```
ggatccacaa ttcccctcta gaaataattt tgtttaactt taagaaggag ataccatg      60
cgtgtggtcc gtgccgctct gcctctgcaa ctgctgctgc tgctgctgct gctgctggct   120
tgtctgctgc cttcttccgg taatgttcct gaactgcctg atacaactga gcatagccgt   180
actgatctgg gcggtgccat ggtgagcaag aagctt                             216
```

<210> SEQ ID NO 65
<211> LENGTH: 399
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 65

```
ggatcctccc gggatgagct gaccaagaac caggtcagcc tgacctgcct ggtcaaaggc    60
ttctatccca gcgacatcgc cgtggagtgg gagagcaatg ggcagccgga gaacaactac   120
aagaccacgc ctcccgtgct ggactccgac ggctccttct tcctctacag caagctcacc   180
gtggacaaga gcaggtggca gcaggggaac gtcttctcat gctccgtgat gcatgaggct   240
ctgcacaacc actacacgca gaagagcctc tccctgtctc cgggtaaaat gctgggccct   300
tgcatgctgc tgctgctgct gctgctgggc ctgaggctgc ctggcgtctg ggccaggaga   360
```
aggcgcagga gaaggcgcag atgatgactc gagaagctt            399

<210> SEQ ID NO 66
<211> LENGTH: 399
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 66
ggatcctccc gggatgagct gaccaagaac caggtcagcc tgacctgcct ggtcaaaggc      60
ttctatccca gcgacatcgc cgtggagtgg gagagcaatg ggcagccgga gaacaactac     120
aagaccacgc ctcccgtgct ggactccgac ggctccttct tcctctacag caagctcacc     180
gtggacaaga gcaggtggca gcagggggaac gtcttctcat gctccgtgat gcatgaggct    240
ctgcacaacc actacacgca gaagagcctc tccctgtctc cgggtaaaag gagaaggcgc    300
aggagaaggc gcagaatgct ggcccttgc atgctgctgc tgctgctgct gctgggcctg     360
aggctgcctg gcgtctgggc ctgatgactc gagaagctt                            399

<210> SEQ ID NO 67
<211> LENGTH: 25
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 67
tcttgcggcc gccaccatgc tgggg                                            25

<210> SEQ ID NO 68
<211> LENGTH: 28
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 68
ctctgagctc agcccacacc ccgggcag                                         28

<210> SEQ ID NO 69
<211> LENGTH: 31
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 69
ctctgagctc agcaagggcg aggagctgtt c                                     31

<210> SEQ ID NO 70
<211> LENGTH: 31
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 70
ctctgaattc cttgtacagc tcgtccatgc c                                     31

<210> SEQ ID NO 71
<211> LENGTH: 25
<212> TYPE: DNA

```
<213> ORGANISM: Artificial Sequence
<220> FEATURE:
<223> OTHER INFORMATION: Custom Designed by IPROGEN BIOTECH INC.

<400> SEQUENCE: 71
tcttgcggcc gccaccatgc tgggg                                         25

<210> SEQ ID NO 72
<211> LENGTH: 29
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 72
tcttcccggg cagcctcagg cccagcagc                                     29

<210> SEQ ID NO 73
<211> LENGTH: 37
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 73
ctctcccggg gtgtgggcta ggaagaagag gaggcag                            37

<210> SEQ ID NO 74
<211> LENGTH: 37
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 74
ctctgagctc ccttctcctc tgcctcctct tcttcct                            37

<210> SEQ ID NO 75
<211> LENGTH: 31
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 75
ctctgagctc agcaagggcg aggagctgtt c                                  31

<210> SEQ ID NO 76
<211> LENGTH: 31
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 76
ctctgaattc cttgtacagc tcgtccatgc c                                  31

<210> SEQ ID NO 77
<211> LENGTH: 54
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 77
ggtaccatgg tgctgctgct gctgctgccc ctgctgtggg ccggcgccct cgag          54
```

<210> SEQ ID NO 78
<211> LENGTH: 54
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 78
ctcgagggcg ccggcccaca gcaggggcag cagcagcagc agcaccatgg tacc         54

<210> SEQ ID NO 79
<211> LENGTH: 66
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 79
ggcgccctgg ccgccgccgt ggccctgctg cccgccgtgc tgctggccct gctggccccc    60
gagctc                                                              66

<210> SEQ ID NO 80
<211> LENGTH: 66
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 80
gagctcgggg gccagcaggg ccagcagcac ggcgggcagc agggccacgg cggcggccag    60
ggcgcc                                                              66

<210> SEQ ID NO 81
<211> LENGTH: 81
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 81
ggcgccctgg ccaaggagac ctggtgggag acctggtgga ccgagtggag ccagcccaag    60
aagaagcgga aggtggagct c                                             81

<210> SEQ ID NO 82
<211> LENGTH: 81
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 82
gagctccacc ttccgcttct tcttgggctg gctccactcg gtccaccagg tctcccacca    60
ggtctccttg gccagggcgc c                                             81

<210> SEQ ID NO 83
<211> LENGTH: 63
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 83

```
ggcgccctgg ccaagaaggc cgccgccgtg ctgctgcccg tgctgctggc cgcccccgag    60
ctc                                                                  63

<210> SEQ ID NO 84
<211> LENGTH: 63
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 84
gagctcgggg gcggccagca gcacgggcag cagcacggcg gcggccttct tggccagggc    60
gcc                                                                  63

<210> SEQ ID NO 85
<211> LENGTH: 39
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 85
ggcgccctgg ccgtgctgct ggccgtgacc cccgagctc                           39

<210> SEQ ID NO 86
<211> LENGTH: 39
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 86
gagctcgggg gtcacggcca gcagcacggc cagggcgcc                           39

<210> SEQ ID NO 87
<211> LENGTH: 42
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 87
ggcgccctgg ccgccgtggt ggtggcccctg gccccccgagc tc                     42

<210> SEQ ID NO 88
<211> LENGTH: 42
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 88
gagctcgggg gccagggcca ccaccacggc ggccagggcg cc                       42

<210> SEQ ID NO 89
<211> LENGTH: 48
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 89
ggcgccctgg ccctggtgct ggccgccccc gccgccctgc ccgagctc                 48
```

```
<210> SEQ ID NO 90
<211> LENGTH: 48
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 90
gagctcgggc agggcggcgg gggcggccag caccagggcc agggcgcc            48

<210> SEQ ID NO 91
<211> LENGTH: 72
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 91
ggcgccctgg ccagcggccg gcagatcaag atctggttcc agaaccggcg gatgaagtgg    60
aagaaggagc tc                                                       72

<210> SEQ ID NO 92
<211> LENGTH: 72
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 92
gagctccttc ttccacttca tccgccggtt ctggaaccag atcttgatct gccggccgct    60
ggccagggcg cc                                                       72

<210> SEQ ID NO 93
<211> LENGTH: 37
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 93
ctctgcggcc gccaccatga ggaagaagag gaggcag                            37

<210> SEQ ID NO 94
<211> LENGTH: 31
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 94
ctctgaattc cttgtacagc tcgtccatgc c                                  31

<210> SEQ ID NO 95
<211> LENGTH: 120
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 95
cttgcggccg ccaccatgct gggcccttgc atgctgctgc tgctgctgct gctgggcctg    60
aggctgcctg gcgtctgggc caggagaagg cgcaggagaa ggcgcagaga gctcggatcc   120

<210> SEQ ID NO 96
```

```
<211> LENGTH: 111
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 96
gcggccgcca ccatgctggg cccctgcatg ctgctgctgc tgctgctgct gggcctgagg      60
ctccagctga gcctgggcag gaagaagagg aggcagagga gaagggagct c              111

<210> SEQ ID NO 97
<211> LENGTH: 23
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 97
ctctggatcc acccatggcg atg                                              23

<210> SEQ ID NO 98
<211> LENGTH: 28
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 98
ctctcccggg ggccaggctc agctggag                                         28

<210> SEQ ID NO 99
<211> LENGTH: 40
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 99
ctctcccggg ggaggtggca gcaagggcga ggagctgttc                            40

<210> SEQ ID NO 100
<211> LENGTH: 25
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 100
ctctgcacgg tgggcatgtg tgagt                                            25

<210> SEQ ID NO 101
<211> LENGTH: 20
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 101
tcaggatgag gtcctgtcag                                                  20

<210> SEQ ID NO 102
<211> LENGTH: 37
<212> TYPE: DNA
<213> ORGANISM: Artificial Sequence
<220> FEATURE:
<223> OTHER INFORMATION: Custom Designed by IPROGEN BIOTECH INC.
```

<400> SEQUENCE: 102
ctctgagctc aggtggcggg gcccagacgc caggcag                                37

<210> SEQ ID NO 103
<211> LENGTH: 20
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 103
tcaggatgag gtcctgtcag                                                  20

<210> SEQ ID NO 104
<211> LENGTH: 55
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 104
ctctgagctc tctgcgcctt ctcctgcgcc ttctcctcag cctcaggccc agcag           55

<210> SEQ ID NO 105
<211> LENGTH: 37
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 105
ctctgcggcc gccaccatgc ctggcgtctg ggccagg                               37

<210> SEQ ID NO 106
<211> LENGTH: 30
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 106
ctctgaattc cttgtacagc tcgtccatgc                                       30

<210> SEQ ID NO 107
<211> LENGTH: 37
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 107
ctctcccggg aggaggaggg agctcagcaa gggcgag                               37

<210> SEQ ID NO 108
<211> LENGTH: 31
<212> TYPE: DNA
<213> ORGANISM: Artificial Sequence
<220> FEATURE:
<223> OTHER INFORMATION: Custom Designed by IPROGEN BIOTECH INC.

<400> SEQUENCE: 108
ctctgaattc cttgtacagc tcgtccatgc c                                     31

<210> SEQ ID NO 109

```
<211> LENGTH: 24
<212> TYPE: PRT
<213> ORGANISM: Artificial Sequence
<220> FEATURE:
<223> OTHER INFORMATION: Custom Designed by IPROGEN BIOTECH INC.

<400> SEQUENCE: 109

Leu Leu Leu Gly Leu Arg Leu Pro Gly Val Trp Ala Arg Arg Arg Arg
1               5                   10                  15

Arg Arg Arg Arg Arg Lys Lys Lys
            20

<210> SEQ ID NO 110
<211> LENGTH: 235
<212> TYPE: PRT
<213> ORGANISM: Artificial Sequence
<220> FEATURE:
<223> OTHER INFORMATION: Designed by IPROGEN BIOTECH INC.

<400> SEQUENCE: 110

Met Ala Leu Gly Pro Cys Met Leu Leu Leu Leu Leu Leu Leu Gly Leu
1               5                   10                  15

Arg Leu Pro Gly Val Trp Ala Pro Pro Arg Arg Arg Arg Arg Arg Arg
            20                  25                  30

Arg Arg Met Ser Asp Gln Glu Ala Lys Pro Ser Thr Glu Asp Leu Gly
        35                  40                  45

Asp Lys Lys Glu Gly Glu Tyr Ile Lys Leu Lys Val Ile Gly Gln Asp
    50                  55                  60

Ser Ser Glu Ile His Phe Lys Val Lys Met Thr Thr His Leu Lys Lys
65                  70                  75                  80

Leu Lys Glu Ser Tyr Cys Gln Arg Gln Gly Val Pro Met Asn Ser Leu
                85                  90                  95

Arg Phe Leu Phe Glu Gly Gln Arg Ile Ala Asp Asn His Thr Pro Lys
            100                 105                 110

Glu Leu Gly Met Glu Glu Glu Asp Val Ile Glu Val Tyr Gln Glu Gln
        115                 120                 125

Thr Gly Gly His Ser Thr Val His Met Lys Glu Asp Trp Asn Val Arg
    130                 135                 140

Ile Thr Lys Leu Arg Lys Gln Val Glu Glu Ile Phe Asn Leu Lys Phe
145                 150                 155                 160

Ala Gln Ala Leu Gly Leu Thr Glu Ala Val Lys Val Pro Tyr Pro Val
                165                 170                 175

Phe Glu Ser Asn Pro Glu Phe Leu Tyr Val Glu Gly Leu Pro Glu Gly
            180                 185                 190

Ile Pro Phe Arg Ser Pro Thr Trp Phe Gly Ile Pro Arg Leu Glu Arg
        195                 200                 205

Ile Val Arg Gly Ser Asn Lys Ile Lys Phe Val Val Lys Lys Pro Glu
    210                 215                 220

Leu Val Ile Leu Glu His His His His His
225                 230                 235

<210> SEQ ID NO 111
<211> LENGTH: 708
<212> TYPE: DNA
<213> ORGANISM: Artificial Sequence
<220> FEATURE:
<223> OTHER INFORMATION: Designed by IPROGEN BIOTECH INC.
```

<400> SEQUENCE: 111

```
atggccttgg gcccttgcat gttgttgttg ttgttgttgt tgggtttgcg cctgccgggt      60
gtttgggcgc cgccgcgtcg ccgccgccgt cgtcgccgtc gtatgagcga tcaggaagcc     120
aagccgagca ccgaggatct gggcgataag aaagagggcg agtatatcaa actgaaggtc    180
attggtcaag actccagcga aattcacttc aaagtgaaga tgaccaccca tctgaaaaag    240
ctgaaagaga gctactgtca gcgtcagggt gtcccgatga acagcctgcg ttttctgttc    300
gagggtcaac gtatcgcaga caatcacacg ccgaaagaac tgggtatgga agaagaggac    360
gttatcgaag tttaccaaga gcagaccggt ggccactcta cggtgcatat gaaagaagat    420
tggaatgtca gaattaccaa gctacggaag caagtggaag agatttttaa tttgaaattt    480
gctcaagctc ttggactcac cgaggcagta aaagtaccat atcctgtgtt tgaatcaaac    540
ccggagttct tgtatgtgga aggcttgcca gagggattc ccttccgaag ccctacctgg     600
tttggaattc cacgacttga aaggatcgtc cgcgggagta ataaaatcaa gttcgttgtt    660
aaaaaacctg aactagttat tctcgagcac caccaccacc accactga                 708
```

<210> SEQ ID NO 112
<211> LENGTH: 38
<212> TYPE: DNA
<213> ORGANISM: Artificial Sequence
<220> FEATURE:
<223> OTHER INFORMATION: Designed by IPROGEN BIOTECH INC.

<400> SEQUENCE: 112

```
gaggagccat ggccttgggc ccttgcatgt tgttgttg                              38
```

<210> SEQ ID NO 113
<211> LENGTH: 34
<212> TYPE: DNA
<213> ORGANISM: Artificial Sequence
<220> FEATURE:
<223> OTHER INFORMATION: Designed by IPROGEN BIOTECH INC.

<400> SEQUENCE: 113

```
atgatgcata tgcaccgtag agtggccacc ggtc                                  34
```

<210> SEQ ID NO 114
<211> LENGTH: 37
<212> TYPE: DNA
<213> ORGANISM: Artificial Sequence
<220> FEATURE:
<223> OTHER INFORMATION: Designed by IPROGEN BIOTECH INC.

<400> SEQUENCE: 114

```
ggaggcatat gaaagaagat tggaatgtca gaattac                               37
```

<210> SEQ ID NO 115
<211> LENGTH: 39
<212> TYPE: DNA
<213> ORGANISM: Artificial Sequence
<220> FEATURE:
<223> OTHER INFORMATION: Designed by IPROGEN BIOTECH INC.

<400> SEQUENCE: 115

```
cctccctcga gaataactag ttcaggtttt ttaacaacg                             39
```